US012778456B2

(12) United States Patent
Huang et al.

(10) Patent No.: US 12,778,456 B2
(45) Date of Patent: Nov. 3, 2026

(54) DETECTION DEVICE, DETECTION METHOD, AND PROGRAM RECORDING MEDIUM

(71) Applicant: NEC Corporation, Tokyo (JP)

(72) Inventors: Chenhui Huang, Tokyo (JP); Kenichiro Fukushi, Tokyo (JP); Zhenwei Wang, Tokyo (JP)

(73) Assignee: NEC CORPORATION, Tokyo (JP)

( * ) Notice: Subject to any disclaimer, the term of this patent is extended or adjusted under 35 U.S.C. 154(b) by 744 days.

(21) Appl. No.: 18/019,967

(22) PCT Filed: Aug. 18, 2020

(86) PCT No.: PCT/JP2020/031055
§ 371 (c)(1),
(2) Date: Feb. 6, 2023

(87) PCT Pub. No.: WO2022/038663
PCT Pub. Date: Feb. 24, 2022

(65) Prior Publication Data
US 2023/0270354 A1 Aug. 31, 2023

(51) Int. Cl.
*A61B 5/11* (2006.01)
*A61B 5/00* (2006.01)

(52) U.S. Cl.
CPC ............ *A61B 5/112* (2013.01); *A61B 5/1122* (2013.01); *A61B 5/1126* (2013.01); (Continued)

(58) Field of Classification Search
CPC ........ A61B 2503/12; A61B 2562/0219; A61B 5/112; A61B 5/1122; A61B 5/1126; A61B 5/6807
See application file for complete search history.

(56) References Cited

U.S. PATENT DOCUMENTS

2013/0006583 A1* 1/2013 Weast .................. A61B 5/6807 702/189
2016/0100801 A1 4/2016 Clark et al.
(Continued)

FOREIGN PATENT DOCUMENTS

JP 2010-005033 A 1/2010
JP 2015-136584 A 7/2015
(Continued)

OTHER PUBLICATIONS

International Search Report for PCT Application No. PCT/JP2020/031055, mailed on Oct. 20, 2020.
(Continued)

*Primary Examiner* — Benjamin S Melhus
(74) *Attorney, Agent, or Firm* — Sughrue Mion, PLLC

(57) ABSTRACT

In order to detect a detailed walking event in both legs on the basis of a physical quantity that relates to leg motion measured by a sensor mounted on one leg, there is provided a detection device including: an extraction unit for generating time-series data that accompany walking, using sensor data based on a physical quantity that relates to leg motion measured by a sensor installed on one leg part of a walking person, and extracting a walking waveform from the generated time-series data; and a detection unit for detecting a walking event in both legs of the walking person from the walking waveform extracted by the extraction unit.

13 Claims, 43 Drawing Sheets

(52) U.S. Cl.
CPC ........ *A61B 5/6807* (2013.01); *A61B 2503/12* (2013.01); *A61B 2562/0219* (2013.01)

(56) References Cited

U.S. PATENT DOCUMENTS

| | | | | |
|---|---|---|---|---|
| 2017/0042453 | A1* | 2/2017 | Cheung | A61B 5/6823 |
| 2018/0007277 | A1* | 1/2018 | Aibara | H04N 5/2627 |
| 2018/0177436 | A1* | 6/2018 | Chang | A61B 5/1101 |
| 2019/0150793 | A1 | 5/2019 | Barth et al. | |
| 2022/0192581 | A1 | 6/2022 | Maeda | |
| 2022/0287590 | A1* | 9/2022 | Gailey | A61B 5/112 |

FOREIGN PATENT DOCUMENTS

| | | | |
|---|---|---|---|
| JP | 2019-150329 | A | 9/2019 |
| JP | 2019-198532 | A | 11/2019 |
| WO | 2018/164157 | A1 | 9/2018 |

OTHER PUBLICATIONS

English translation of Written opinion for PCT Application No. PCT/JP2020/031055, mailed on Oct. 20, 2020.
US Office Action for U.S. Appl. No. 18/539,365, mailed on Jan. 15, 2026.
US Office Action for U.S. Appl. No. 18/541,194, mailed on Jan. 14, 2026.

* cited by examiner

DETECTION DEVICE, DETECTION METHOD, AND PROGRAM RECORDING MEDIUM

This application is a National Stage Entry of PCT/JP2020/031055 filed on Aug. 18, 2020, the contents of all of which are incorporated herein by reference, in their entirety.

TECHNICAL FIELD

The present disclosure relates to a detection device or the like that detects a gait event.

BACKGROUND ART

With increasing interest in healthcare that performs physical condition management, a service that measures a gait including a walking feature and provides information corresponding to the gait to a user has attracted attention. If a gait event such as an event in which the heel touches the ground or an event in which the toe leaves the ground can be detected from the data related to walking, a service corresponding to the gait can be more accurately provided.

PTL 1 discloses a method for analyzing data of plantar pressure for a predetermined time during walking and standing still acquired by a pressure-sensitive sensor provided in an insole of a shoe. In the method of PTL 1, a plantar pressure parameter, a foot pressure center parameter, and a time parameter during walking, and a plantar pressure parameter and a foot pressure center parameter during standing still are acquired and accumulated.

PTL 2 discloses a device that determines a walking motion of a subject from a change in acceleration of a body part caused by walking. The device of PTL 2 includes a uniaxial acceleration sensor that is attached to the body and detects acceleration in a uniaxial direction other than the left-right axis direction of a body part caused by walking. The device of PTL 2 extracts a feature amount of an acceleration waveform generated from a detection result of the uniaxial acceleration sensor. The device of PTL 2 determines whether the left-right balance of the walking motion is normal using the feature amount of the acceleration waveform in the stance phase related to the motion of the left and right legs in the gait cycle.

PTL 3 discloses a device that applies electrical stimulation to a lower limb of a user. In the device of PTL 3, when the phase of a walking motion is the swing phase, the current is output to a back electrode unit attached to the back portion related to the lower limb dorsal muscle group existing on the back side of the lower limb among the muscles straddling the knee joint. In the device of PTL 3, when the phase of the walking motion is the stance phase, the current is output to a front electrode unit attached to the front portion related to the lower limb ventral muscle group existing on the front side of the lower limb among the muscles straddling the knee joint.

CITATION LIST

Patent Literature

[PTL 1] WO 2018/164157 A
[PTL 2] JP 2010-005033 A
[PTL 3] JP 2015-136584 A

SUMMARY OF INVENTION

Technical Problem

In the method of PTL 1, the stance phase and the idling period can be automatically detected based on the plantar pressure data acquired using the pressure-sensitive sensor. However, in the method of PTL 1, since the gait event is detected based on the data of the plantar pressure, the data in the stance phase can be acquired, but the data in the swing phase cannot be acquired. That is, in the method of PTL 1, even if the data of the plantar pressures of both feet is used, the gait event in the swing phase cannot be detected.

In the method of PTL 2, acceleration in a uniaxial direction is detected by the uniaxial acceleration sensor attached to a body part, such as a waist back, where bilateral symmetry on a midline of a body can be analyzed. In the method of PTL 2, it is possible to determine the left-right balance of the walking motion together with the gait parameters such as the number of steps, the walking distance, the walking speed, and the stride length, but it is not possible to obtain information for subdividing the gait event. That is, in the method of PTL 2, a detailed gait event cannot be detected using a single sensor.

In the method of PTL 3, motions of the thigh, lower thigh, and foot can be detected on the basis of data detected by sensors attached to the thigh, lower thigh, and foot, and the stance phase and the swing phase can be subdivided. However, in the method of PTL 3, it is necessary to use a plurality of sensors separately for the thigh, the lower leg, and the foot. In addition, in the method of PTL 3, since the movement of the foot is detected by the pressure sensors provided under the toe and the heel, in order to subdivide the walking phase in the swing phase, it is necessary to perform interpolation with data detected by the sensors provided in the thigh and the lower thigh. That is, in the method of PTL 3, it is necessary to use a plurality of sensors when detecting a gait event.

An object of the present invention is to provide a detection device and the like capable of detecting a detailed gait event of both feet on the basis of a physical quantity related to movement of a foot measured by a sensor attached to one foot.

Solution to Problem

A detection device according to an aspect of the present disclosure includes: an extraction unit configured to generate time-series data associated with walking using sensor data based on a physical quantity related to movement of a foot measured by a sensor installed in one foot portion of a pedestrian, and extract a gait waveform from the generated time-series data; and a detection unit configured to detect a gait event of both feet of the pedestrian from the gait waveform extracted by the extraction unit.

In a detection method according to an aspect of the present disclosure, a computer executes: generating time-series data associated with walking using sensor data based on a physical quantity related to movement of a foot measured by a sensor installed in one foot portion of a pedestrian; extracting a gait waveform from the generated time-series data; and detecting a gait event of both feet of the pedestrian from the extracted gait waveform.

A program according to one aspect of the present disclosure causes a computer to execute processing of generating time-series data associated with walking using sensor data based on a physical quantity related to a movement of a foot measured by a sensor installed in one foot portion of a pedestrian; processing of extracting a gait waveform from the generated time-series data; and processing of detecting a gait event of both feet of the pedestrian from the extracted gait waveform.

Advantageous Effects of Invention

According to the present disclosure, it is possible to provide a detection device and the like capable of detecting a detailed gait event of both feet on the basis of a physical quantity related to movement of a foot measured by a sensor attached to one foot.

BRIEF DESCRIPTION OF DRAWINGS

FIG. 41 is a conceptual diagram illustrating an example of transmitting information related to a physical condition estimated by the detection device of the detection system according to the second example embodiment to a medical institution or the like.

EXAMPLE EMBODIMENT

Figure 1:
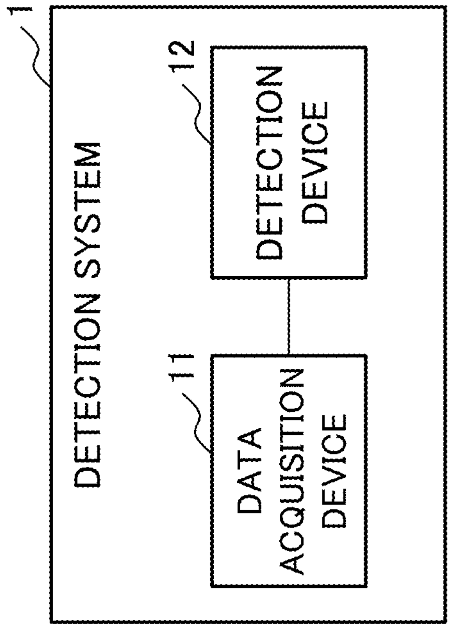
FIG. 1 is a block diagram illustrating an example of a configuration of a detection system according to a first example embodiment.

Hereinafter, example embodiments of the present invention will be described with reference to the drawings. However, the example embodiments described below have technically preferable limitations for carrying out the present invention, but the scope of the invention is not limited to the following. In all the drawings used in the following description of the example embodiment, the same reference numerals are given to the same parts unless there is a particular reason. Further, in the following example embodiments, repeated description of similar configurations and operations may be omitted.

First Example Embodiment

First, a detection system according to a first example embodiment will be described with reference to the drawings. The detection system of the present example embodiment detects a gait event of a pedestrian using sensor data acquired by a sensor installed on a foot portion of the pedestrian. In particular, in the present example embodiment, a gait event of both feet of a pedestrian is detected using sensor data acquired by a sensor installed on footwear on one foot of the pedestrian. As will be described in detail later, the gait event includes an event in which the foot touches the ground, an event in which the foot leaves the ground, and the like. In the present example embodiment, a system in which the right foot is a reference foot and the left foot is an opposite foot will be described. In the present example embodiment, the present invention can also be applied to a system in which the left foot is a reference foot and the right foot is an opposite foot.

(Configuration)

FIG. 1 is a block diagram illustrating an example of a configuration of a detection system 1 of the present example embodiment. As illustrated in FIG. 1, the detection system 1 includes a data acquisition device 11 and a detection device 12. The data acquisition device 11 and the detection device 12 may be connected by wire or wirelessly. In addition, the data acquisition device 11 and the detection device 12 may be configured by a single device. In addition, the detection system 1 may be configured only by the detection device 12 by excluding the data acquisition device 11 from the configuration of the detection system 1.

The data acquisition device 11 is installed on a foot portion. For example, the data acquisition device 11 is installed on footwear on the right foot. The data acquisition device 11 measures acceleration (also referred to as spatial acceleration) and angular velocity (also referred to as spatial angular velocity) as physical quantities related to the movement of the foot of the user wearing footwear such as shoes. The physical quantity related to the movement of the foot measured by the data acquisition device 11 includes a speed, an angle, and a trajectory calculated by integrating the acceleration and the angular velocity in addition to the acceleration and the angular velocity. The data acquisition device 11 converts the measured physical quantity into digital data (also referred to as sensor data). The data acquisition device 11 transmits the converted sensor data to the detection device 12. Sensor data such as acceleration and angular velocity generated by the data acquisition device 11 is also referred to as a gait parameter. In addition, a speed, an angle, a trajectory, and the like calculated by integrating the acceleration and the angular velocity are also included in the gait parameter.

The data acquisition device 11 is implemented by, for example, an inertial measurement device including an acceleration sensor and an angular velocity sensor. An example of the inertial measurement unit is an inertial measurement unit (IMU). The IMU includes a three-axis acceleration sensor and a three-axis angular velocity sensor. Furthermore, examples of the inertial measurement device include a vertical gyro (VG), an attitude heading (AHRS), and a GPS/INS (Global Positioning System/Inertial Navigation System).

Figure 2:
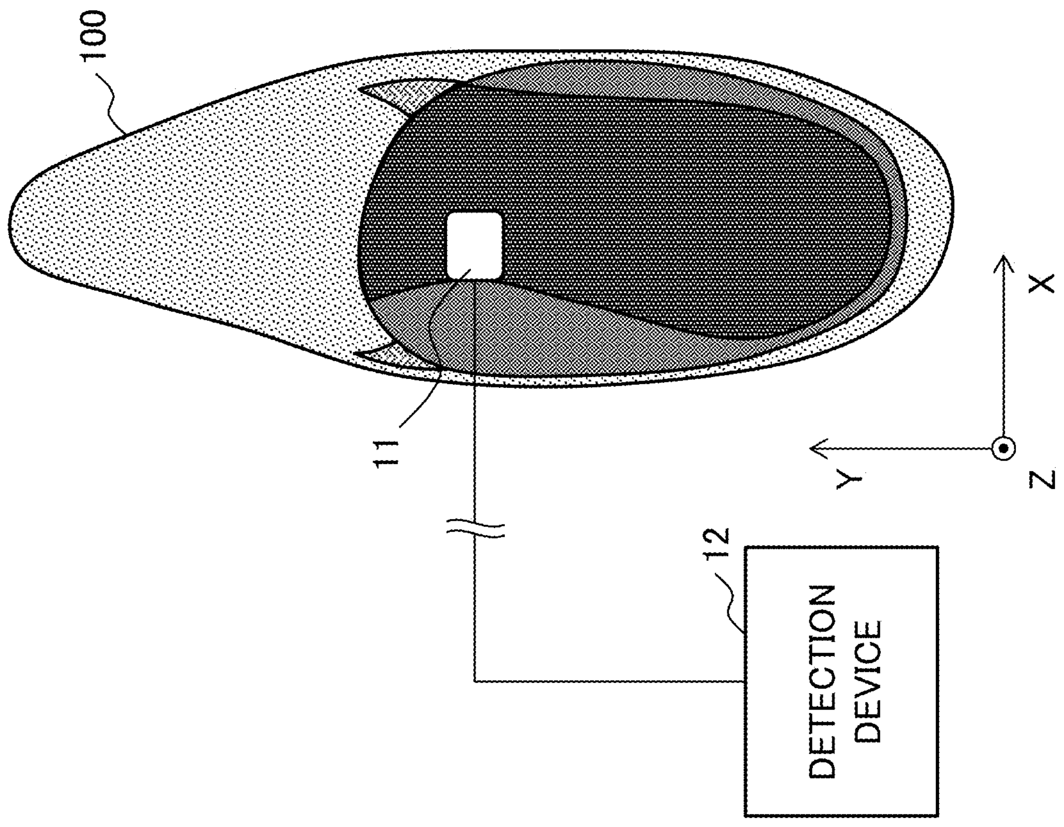
FIG. 2 is a conceptual diagram illustrating an example in which a data acquisition device of the detection system according to the first example embodiment is disposed in footwear.

FIG. 2 is a conceptual diagram illustrating an example in which the data acquisition device 11 is installed in the shoe 100. In the example of FIG. 2, the data acquisition device 11 is installed at a position corresponding to the back side of the arch of foot. For example, the data acquisition device 11 is installed in an insole inserted into the shoe 100. For example, the data acquisition device 11 is installed on the bottom surface of the shoe 100. For example, the data acquisition device 11 is embedded in the main body of the shoe 100. The data acquisition device 11 may be detachable from the shoe 100 or may not be detachable from the shoe 100. The data acquisition device 11 may be installed at a position that is not the back side of the arch of the foot as long as it can acquire sensor data related to the movement of the foot. Furthermore, the data acquisition device 11 may be installed on a sock worn by the user or a decorative article such as an anklet worn by the user. In addition, the data acquisition device 11 may be directly attached to the foot or may be embedded in the foot. FIG. 2 illustrates an example in which the data acquisition device 11 is installed in the shoe 100 of the right foot. The data acquisition device 11 only needs to be installed on at least one foot, and may be installed on both left and right feet. If the data acquisition device 11 is installed in the shoes 100 of both feet, the gait event can be detected in association with the movement of both feet.

Figure 3:
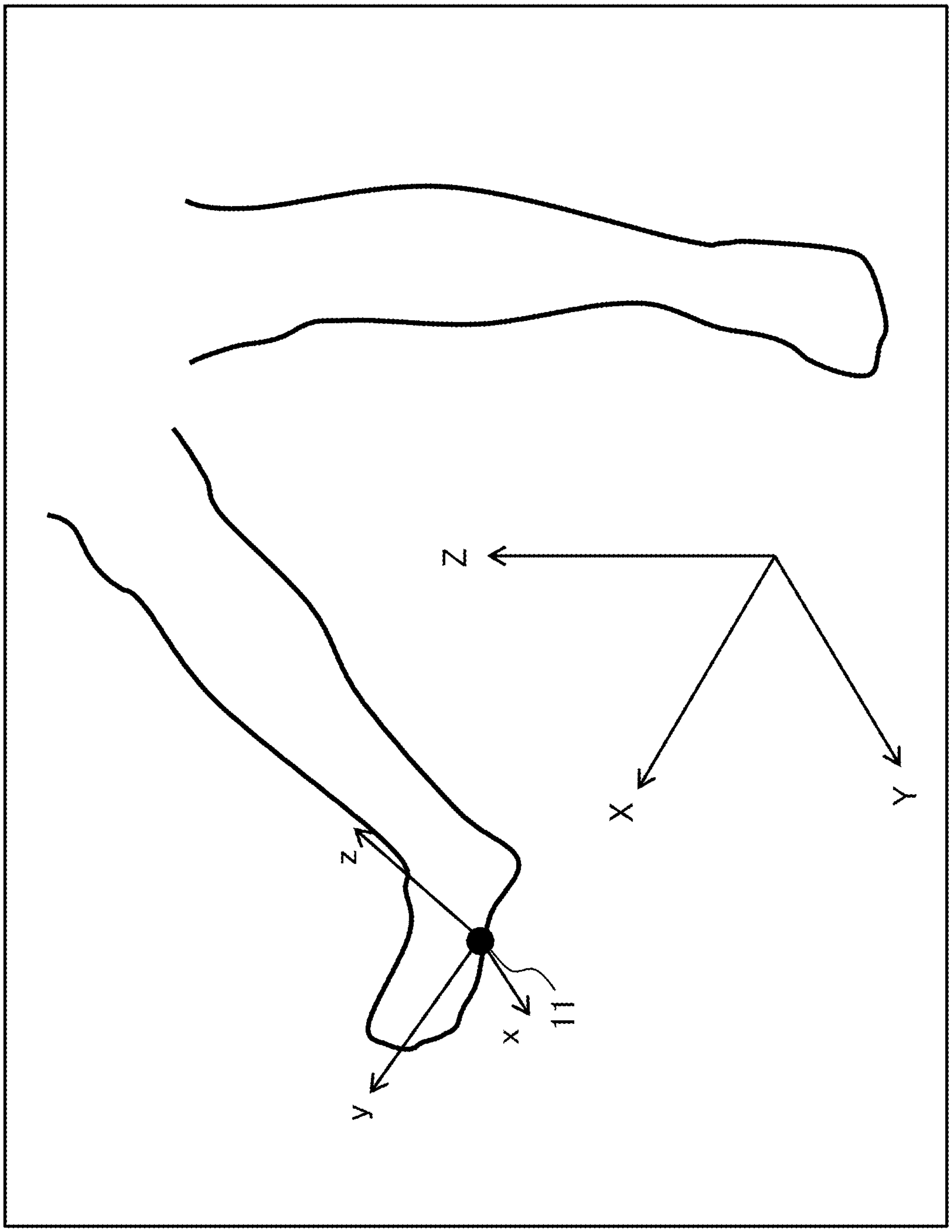
FIG. 3 is a conceptual diagram for explaining a local coordinate system and a world coordinate system set in the data acquisition device of the detection system according to the first example embodiment.

FIG. 3 is a conceptual diagram for describing a local coordinate system (x-axis, y-axis, z-axis) set in the data acquisition device 11 and a world coordinate system (X-axis, Y-axis, Z-axis) set with respect to the ground in a case where the data acquisition device 11 is installed on the back side of the arch of foot. In the world coordinate system (X-axis, Y-axis, Z-axis), in a state where the user is standing upright, a lateral direction of the user is set to an X-axis direction (rightward direction is positive), a front direction of the user (traveling direction) is set to a Y-axis direction (forward direction is positive), and a gravity direction is set to a Z-axis direction (vertically upward direction is positive). Furthermore, in the present example embodiment, a local coordinate system including an x-direction, a y-direction, and a z-direction based on the data acquisition device 11 is set. In the present example embodiment, rotation around the x-axis is defined as pitch, rotation around the y-axis is defined as roll, and rotation around the z-axis is defined as yaw.

The detection device 12 acquires sensor data in the local coordinate system from the data acquisition device 11. The detection device 12 converts the acquired sensor data in the local coordinate system into the world coordinate system to generate time-series data. The detection device 12 extracts waveform data (hereinafter, also referred to as a gait waveform) for one gait cycle or two gait cycles from the generated time-series data. The detection device 12 detects a gait event to be described later from the extracted gait waveform. The gait event detected by the detection device 12 is used for measuring the gait of the pedestrian and the like.

Figure 4:
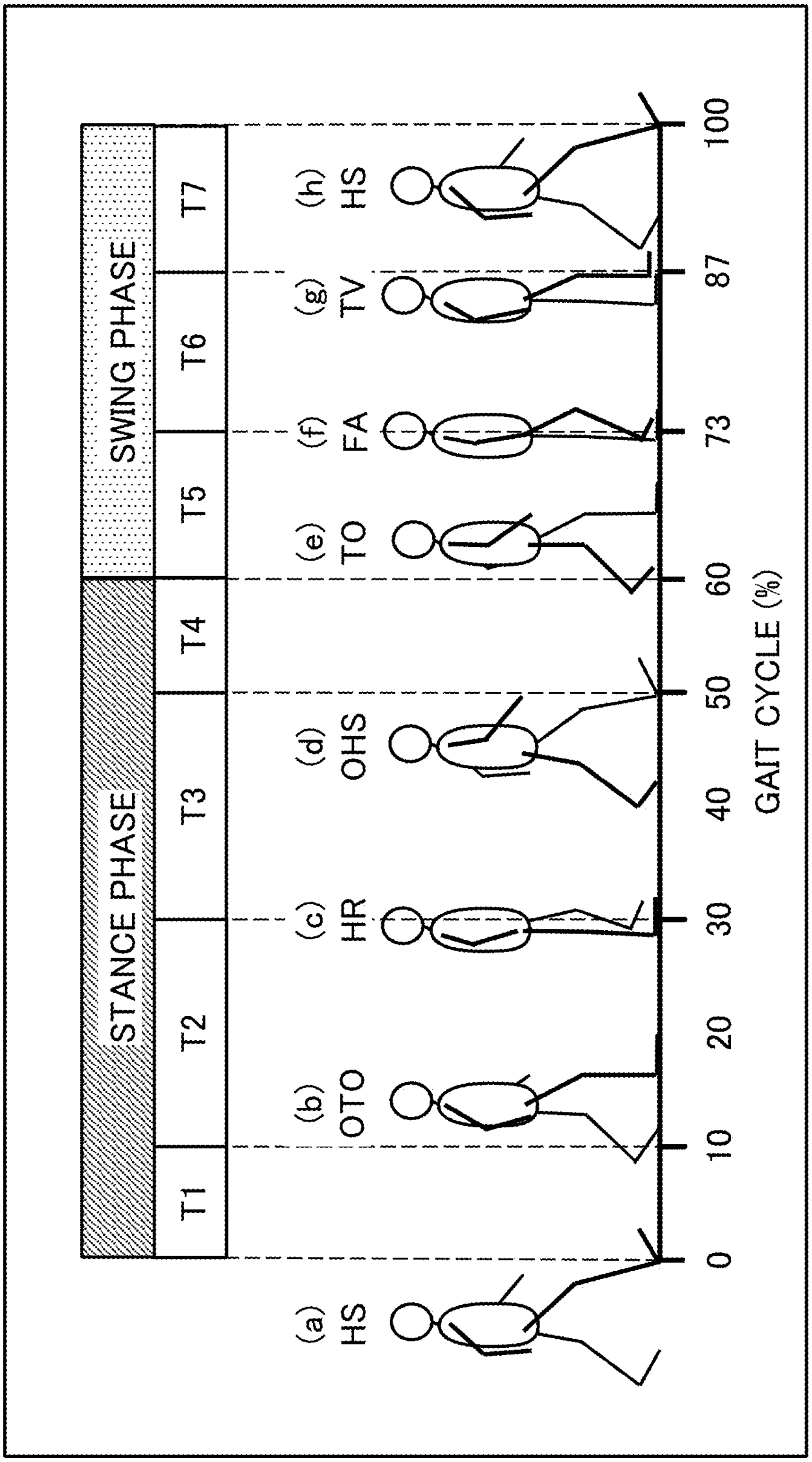
FIG. 4 is a conceptual diagram for explaining a gait event detected by the detection system according to the first example embodiment.

FIG. 4 is a conceptual diagram for explaining the gait event detected by the detection device 12. FIG. 4 is associated with one gait cycle of the right foot. The horizontal axis in FIG. 4 represents a normalized time (also referred to as normalization time) with one gait cycle of the right foot as 100%, with a time at which the heel of the right foot lands on the ground as a start point and a time at which the heel of the right foot next lands on the ground as an end point. In general, one gait cycle of one foot is roughly divided into a stance phase in which at least a part of the back side of the foot is in contact with the ground and a swing phase in which the back side of the foot is away from the ground. The stance phase is further subdivided into an initial stance stage T1, a mid-stance stage T2, a terminal stance stage T3, and a preswing stage T4. The swing phase is further subdivided into an initial swing stage T5, a mid-swing stage T6, and a terminal swing stage T7.

In FIG. 4, (a) represents an event (heel-strike (HS)) in which the heel of the right foot touches the ground. (b) represents an event (opposite toe-off: OTO) in which the toe of the opposite foot (left foot) leaves the ground with the sole of the right foot in contact with the ground. (c) represents an event (heel-rise: HR) in which the heel of the right foot lifts with the sole of the right foot in contact with the ground. (d) represents an event (opposite heel-strike: OHS) in which the heel of the opposite foot (left foot) touches the ground. (e) represents an event (toe-off (TO)) in which the toe of the right foot leaves the ground with the sole of the opposite foot (left foot) in contact with the ground. (f) represents an event (foot-adjacent: FA) in which the opposite foot (left foot) passes the right foot. (g) represents the event (tibia-vertical: TV) in which the tibia of the right foot becomes almost vertical to the ground with the sole of the left foot in contact with the ground. (h) represents an event (heel-strike: HS) in which the heel of the right foot touches the ground. (h) corresponds to the end point of one gait cycle starting from the heel-strike in (a) and corresponds to the start point of the next gait cycle.

In the present example embodiment, each of the events (also referred to as gait events) illustrated in (a) to (h) is detected on the basis of the physical quantity related to the movement of the right foot. In the present example embodiment, the above-described gait events (heel-strike HS, opposite toe-off OTO, heel-rise HR, opposite heel-strike OHS, toe-off TO, foot-adjacent FA, and tibia-vertical TV) are detected from the gait waveform of the pedestrian.

[Data Acquisition Device]

Figure 5:
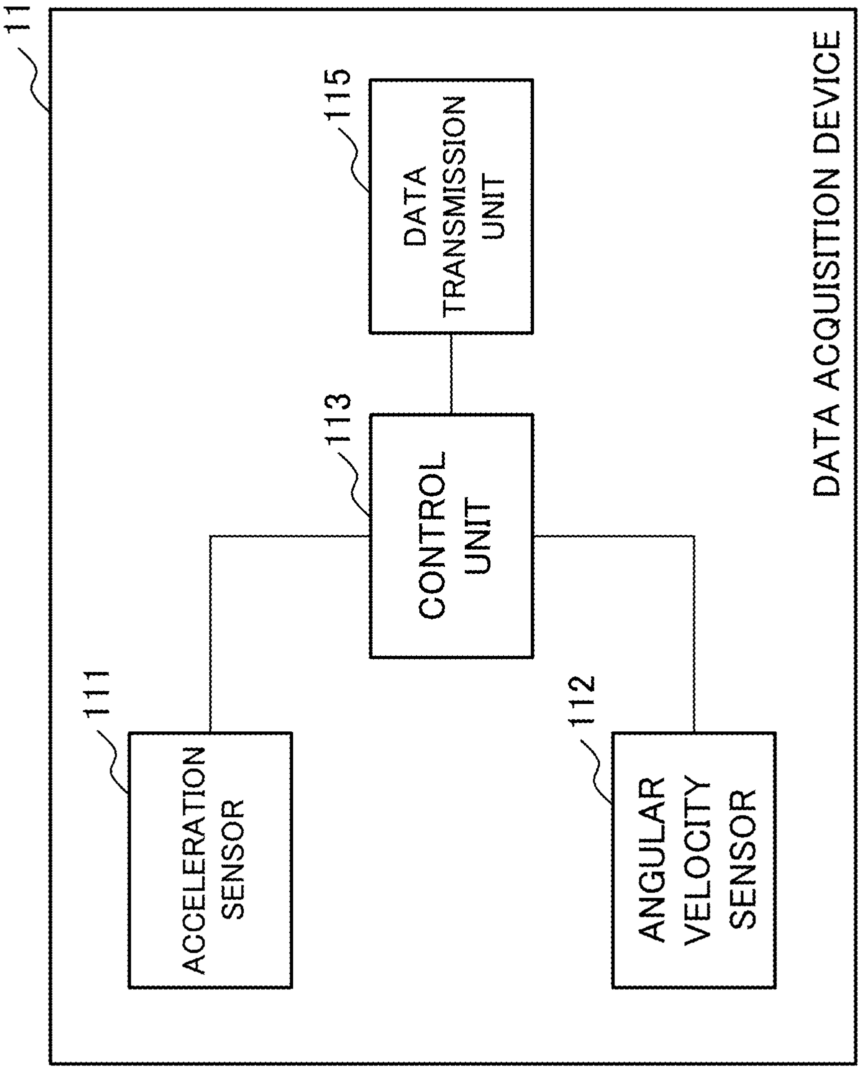
FIG. 5 is a block diagram illustrating an example of a configuration of a data acquisition device of the detection system according to the first example embodiment.

Next, details of the data acquisition device 11 will be described with reference to the drawings. FIG. 5 is a block diagram illustrating an example of a detailed configuration of the data acquisition device 11. The data acquisition device 11 includes an acceleration sensor 111, an angular velocity sensor 112, a control unit 113, and a data transmission unit 115. In addition, the data acquisition device 11 includes a power supply (not illustrated). In the following description, each of the acceleration sensor 111, the angular velocity sensor 112, the control unit 113, and the data transmission unit 115 will be described as the subject of operation, but the data acquisition device 11 may be regarded as the subject of operation.

The acceleration sensor 111 is a sensor that measures accelerations (also referred to as spatial accelerations) in three axial directions. The acceleration sensor 111 outputs the measured acceleration to the control unit 113. For example, a sensor of a piezoelectric type, a piezoresistive type, a capacitance type, or the like can be used as the acceleration sensor 111. Note that the sensor used for the acceleration sensor 111 is not limited to the measurement type as long as the sensor can measure acceleration.

The angular velocity sensor 112 is a sensor that measures angular velocities in three axial directions (also referred to as spatial angular velocities). The angular velocity sensor 112 outputs the measured angular velocity to the control unit 113. For example, a sensor of a vibration type, a capacitance type, or the like can be used as the angular velocity sensor 112. Note that the sensor used for the angular velocity sensor 112 is not limited to the measurement type as long as the sensor can measure the angular velocity.

The control unit 113 acquires each of acceleration and angular velocity in three axial directions from each of the acceleration sensor 111 and the angular velocity sensor 112. The control unit 113 converts the acquired acceleration and angular velocity into digital data, and outputs the converted digital data (also referred to as sensor data) to the data transmission unit 115. The sensor data includes at least acceleration data (including acceleration vectors in three axial directions) obtained by converting acceleration of analog data into digital data and angular velocity data (including angular velocity vectors in three axial directions) obtained by converting angular velocity of analog data into digital data. Note that acquisition times of the acceleration data and the angular velocity data are associated with the acceleration data and the angular velocity data. Furthermore, the control unit 113 may be configured to output sensor data obtained by adding correction such as a mounting error, temperature correction, and linearity correction to the acquired acceleration data and angular velocity data. Furthermore, the control unit 113 may generate angle data in three axial directions using the acquired acceleration data and angular velocity data.

For example, the control unit 113 is a microcomputer or a microcontroller that performs overall control and data processing of the data acquisition device 11. For example, the control unit 113 includes a central processing unit (CPU), a random access memory (RAM), a read only memory (ROM), a flash memory, and the like. The control unit 113 controls the acceleration sensor 111 and the angular velocity sensor 112 to measure the angular velocity and the acceleration. For example, the control unit 113 performs analog-to-digital conversion (AD conversion) on physical quantities (analog data) such as the measured angular velocity and acceleration, and stores the converted digital data in a flash memory. Note that the physical quantity (analog data) measured by the acceleration sensor 111 and the angular velocity sensor 112 may be converted into digital data in each of the acceleration sensor 111 and the angular velocity sensor 112. The digital data stored in the flash memory is output to the data transmission unit 115 at a predetermined timing.

The data transmission unit 115 acquires sensor data from the control unit 113. The data transmission unit 115 transmits the acquired sensor data to the detection device 12. The data transmission unit 115 may transmit the sensor data to the detection device 12 via a wire such as a cable, or may transmit the sensor data to the detection device 12 via wireless communication. For example, the data transmission unit 115 is configured to transmit sensor data to the detection device 12 via a wireless communication function (not illustrated) conforming to a standard such as Bluetooth (registered trademark) or WiFi (registered trademark). Note that the communication function of the data transmission unit 115 may conform to a standard other than Bluetooth (registered trademark) or WiFi (registered trademark).

[Detection Device]

Figure 6:
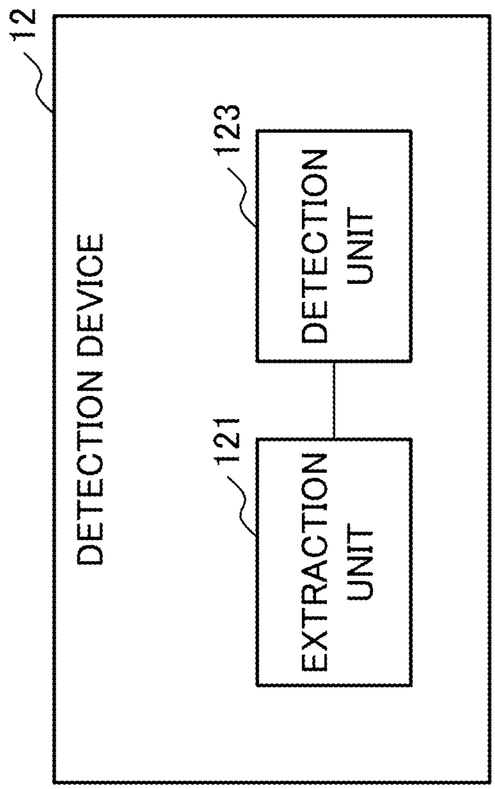
FIG. 6 is a block diagram illustrating an example of a configuration of a detection device of the detection system according to the first example embodiment.

Next, details of the detection device 12 included in the detection system 1 will be described with reference to the drawings. FIG. 6 is a block diagram illustrating an example of a configuration of the detection device 12. The detection device 12 includes an extraction unit 121 and a detection unit 123.

The extraction unit 121 acquires sensor data from the data acquisition device 11 (sensor) installed on the footwear worn by the pedestrian. The extraction unit 121 uses the sensor data to generate time-series data associated with walking of the pedestrian wearing the footwear on which the data acquisition device 11 is installed. The extraction unit 121 extracts gait waveform data for one gait cycle or two gait cycles from the generated time-series data.

For example, the extraction unit 121 acquires sensor data from the data acquisition device 11. The extraction unit 121 converts the coordinate system of the acquired sensor data from the local coordinate system to the world coordinate system. When the user is standing upright, the local coordinate system (x-axis, y-axis, z-axis) and the world coordinate system (X-axis, Y-axis, Z-axis) coincide. Since the spatial orientation of the data acquisition device 11 changes while the user is walking, the local coordinate system (x-axis, y-axis, z-axis) and the world coordinate system (X-axis, Y-axis, Z-axis) do not match. Therefore, the extraction unit 121 converts the sensor data acquired by the data acquisition device 11 from the local coordinate system (x-axis, y-axis, z-axis) of the data acquisition device 11 into the world coordinate system (X-axis, Y-axis, Z-axis).

For example, the extraction unit 121 generates time-series data such as a spatial acceleration and a spatial angular velocity. Furthermore, the extraction unit 121 integrates the spatial acceleration and the spatial angular velocity, and generates time-series data such as the spatial velocity, the spatial angle (plantar angle), and the spatial trajectory. The extraction unit 121 generates time-series data at a predetermined timing or time interval set in accordance with a general gait cycle or a gait cycle unique to the user. The timing at which the extraction unit 121 generates the time-series data can be arbitrarily set. For example, the extraction unit 121 is configured to continue to generate time-series data during a period in which walking of the user is continued. Furthermore, the extraction unit 121 may be configured to generate time-series data at a specific time.

The detection unit 123 detects a gait event of a pedestrian walking in footwear on which the data acquisition device 11 is installed from the gait waveform data generated by the extraction unit 121. For example, the detection unit 123 extracts a feature for each gait event from a gait waveform of a physical quantity related to the movement of the foot. For example, the detection unit 123 detects the timing of the extracted feature for each gait event as the timing of each gait event. For example, the detection unit 123 outputs the detected gait event to a system or a device (not illustrated).

[Gait Event]

Next, an example of detection of a gait event by the detection device 12 will be described with reference to the drawings. In the present example embodiment, the center timing of the stance phase (the start of the terminal stance stage) is set as the start point of one gait cycle. In the present example embodiment, an example of detecting a heel-strike, an opposite toe-off, a heel-rise, an opposite heel-strike, a toe-off, a foot-adjacent, and a tibia-vertical as a gait event will be described. In the following, description will be made along the order of detection of the gait event, not the order of time-series in the gait waveform of one gait cycle.

Hereinafter, an example in which the data acquisition device 11 verifies the gait of a subject wearing the footwear on which the device is installed will be described. In this verification, the data acquisition device 11 was installed on one foot (right foot). This verification uses, as a population, thirty two male and female subjects of ages of 20s to 50s, heights of 150 to 180 cm, and weights of 45 to 100 kilograms. In this verification, a population of thirty two subjects was set, and the gait of the pedestrian wearing the footwear in which the data acquisition device 11 was installed was measured by the motion capture and the detection device 12. In this verification, the gait (Y-direction position, Z-direction height, roll angle) measured by motion capture was compared with the gait measured by the detection device 12 using the sensor data based on the physical quantity measured by the data acquisition device 11.

Figure 7:
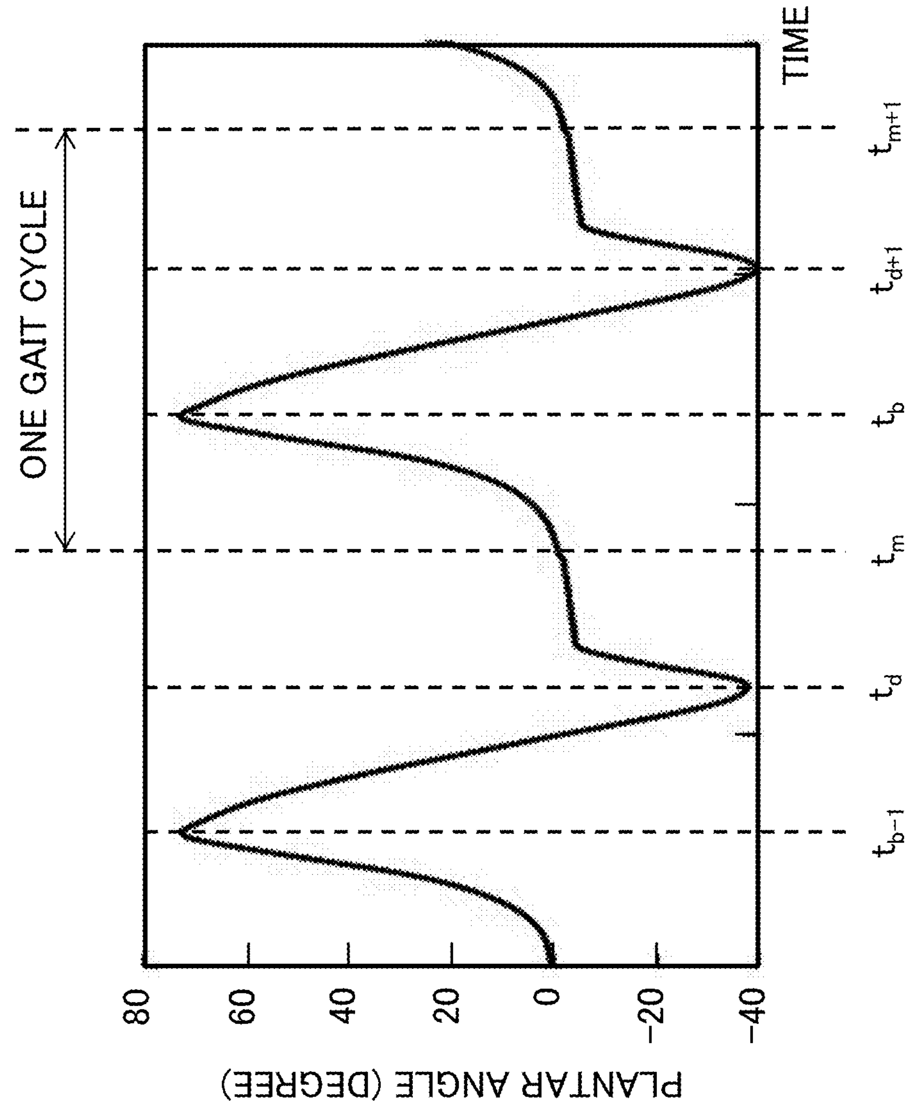
FIG. 7 is a graph for explaining a gait waveform of a plantar angle generated by the detection device of the detection system according to the first example embodiment.

FIG. 7 is a graph for explaining a gait waveform of the plantar angle. In FIG. 7, a state (dorsiflexion) in which the toe is located above the heel is defined as negative, and a state (plantarflexion) in which the toe is located below the heel is defined as positive. The time $t_d$ at which the gait waveform of the plantar angle becomes minimum corresponds to the start timing of the stance phase. The time $t_b$ at which the gait waveform of the plantar angle becomes maximum corresponds to the start timing of the swing phase.

The time at the midpoint between time $t_d$ of the start of the stance phase and time $t_b$ of the start of the swing phase corresponds to the center timing of the stance phase. In the present example embodiment, the time at the center timing of the stance phase is set to time $t_m$ of the start point of one gait cycle. Furthermore, in the present example embodiment, the time at the center timing of the stance phase next to the timing of time $t_m$ is set to time $t_{m+1}$ of the end point of one gait cycle.

Figure 8:
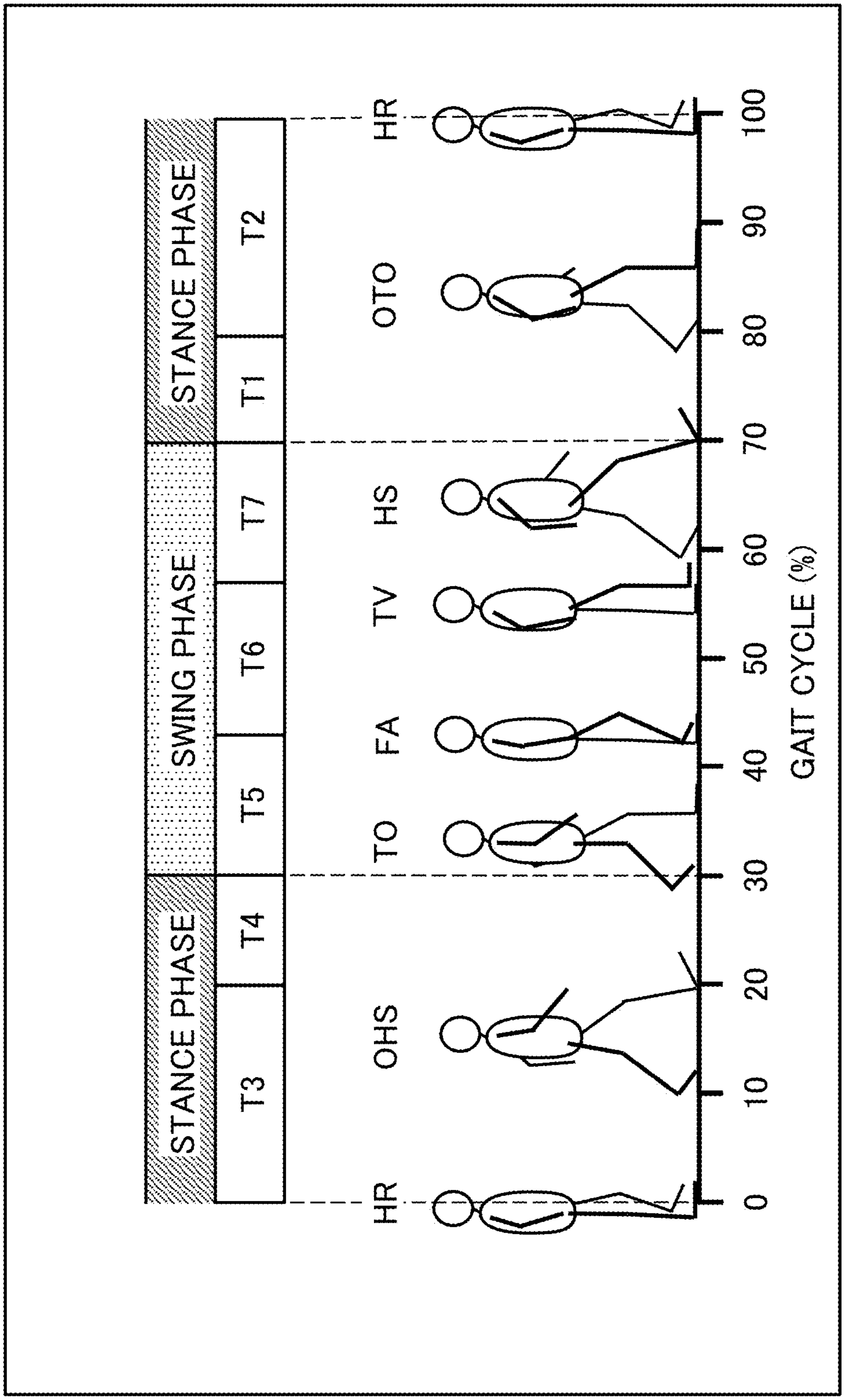
FIG. 8 is a conceptual diagram for explaining a gait cycle corresponding to one gait cycle cut out by the detection device of the detection system according to the first example embodiment.

FIG. 8 is a graph for explaining one gait cycle with time $t_m$ as a start point and time $t_{m+1}$ as an end point. The detection unit 123 detects, from the gait waveform of the plantar angle for one gait cycle, time $t_d$ at which the gait waveform becomes minimum (first dorsiflexion peak) and time $t_b$ at which the gait waveform becomes maximum (first plantarflexion peak) next to the first dorsiflexion peak. Furthermore, the detection unit 123 detects, from the gait waveform of the plantar angle for the next one gait cycle, time $t_{d+1}$ at which the gait waveform becomes minimum (second dorsiflexion peak) next to the first plantarflexion peak and time $t_{b+1}$ at which the gait waveform becomes maximum (second plantarflexion peak) next to the second dorsiflexion peak. The detection unit 123 sets the time at the midpoint between time $t_d$ and time $t_b$ as time $t_m$ of the start point of one gait cycle. In addition, the detection unit 123 sets the time at the midpoint between time $t_{d+1}$ and time $t_{b+1}$ as time $t_{m+1}$ of the end point of one gait cycle.

The detection unit 123 cuts out a gait waveform for one gait cycle from time $t_m$ to time $t_{m+1}$ with respect to time-series data of sensor data based on a physical quantity related to the movement of the foot measured by the data acquisition device 11. For example, the detection unit 123 cuts out gait waveform data for one gait cycle starting from the midpoint (time $t_m$) between time $t_d$ of the first dorsiflexion peak and time $t_b$ of the first plantarflexion peak and ending at the midpoint (time $t_{m+1}$) between time $t_{d+1}$ of the second dorsiflexion peak and time $t_{b+1}$ of the second plantarflexion peak. Similarly, the detection unit 123 cuts out a gait waveform for one gait cycle from time $t_m$ to time $t_{m+1}$ with respect to time-series data of sensor data based on a physical quantity (spatial acceleration, spatial angular velocity, spatial trajectory) related to the movement of the foot measured by the data acquisition device 11.

For example, the detection unit 123 divides the cut-out gait waveform for one gait cycle into a section from time $t_m$ to time $t_b$, a section from time $t_b$ to time $t_{d+1}$, and a section from time $t_{d+1}$ to time $t_{m+1}$. A waveform in a section from time $t_m$ to time $t_b$ is referred to as a first gait waveform W1, a waveform in a section from time $t_b$ to time $t_{d+1}$ is referred to as a second gait waveform W2, and a waveform in a section from time $t_{d+1}$ to time $t_{m+1}$ is referred to as a third gait waveform W3. Expressed as a gait event, a waveform in a section from the heel-rise HR to the toe-off TO is a first gait waveform W1, a waveform in a section from the toe-off TO to the heel-strike HS is a second gait waveform W2, and a waveform in a section from the heel-strike HS to the heel-rise HR is a third gait waveform W3. In FIG. 8, 30% of one gait cycle corresponds to the timing of toe-off, and 70% of one gait cycle corresponds to the timing of the heel-strike. Since the timing at which each gait event appears differs depending on the person and the physical condition, the timing of the toe-off and the heel-strike does not completely coincide with the gait cycle of FIG. 8.

Figure 9:
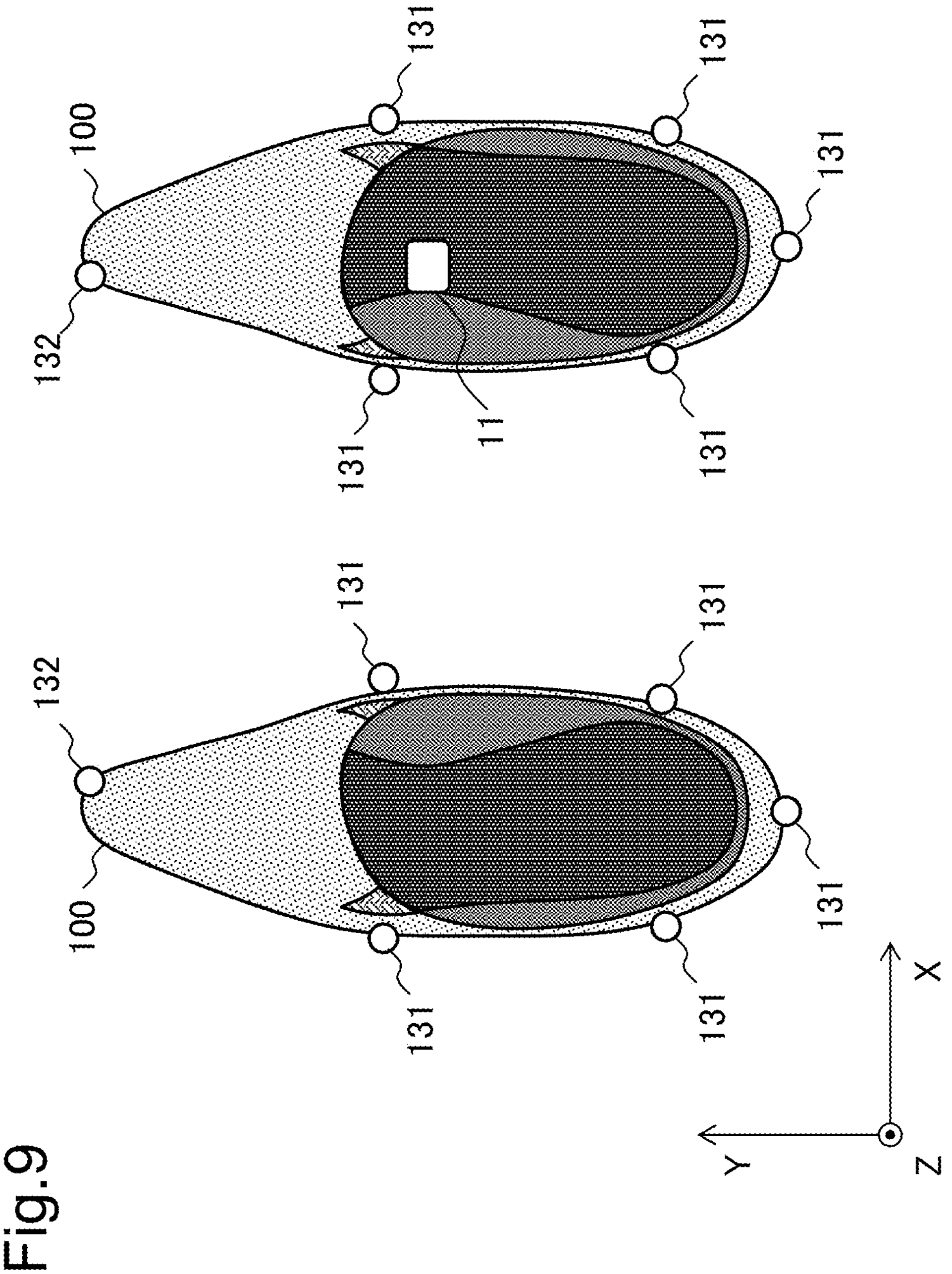
FIG. 9 is a conceptual diagram for explaining a position of a mark attached to the periphery of the shoe when the gait of the subject is measured.

FIG. 9 is a conceptual diagram of shoes 100 with marks 131 and 132 attached for motion capture. In this verification, five marks 131 and one mark 132 were attached to each of the shoes 100 of both feet. Five marks 131 were arranged on the side surface around the opening of the shoe. The five marks 131 are marks for detecting the movement of the heel. The center of gravity of the rigid body model that regards the five marks 131 as rigid bodies is detected as the position of the heel. The mark 132 is arranged at the position of the toe of the shoe 100. The mark 132 is detected as the position of the toe. In addition, the data acquisition device 11 was installed at a position corresponding to the back side of the arch of the right foot.

Figure 10:
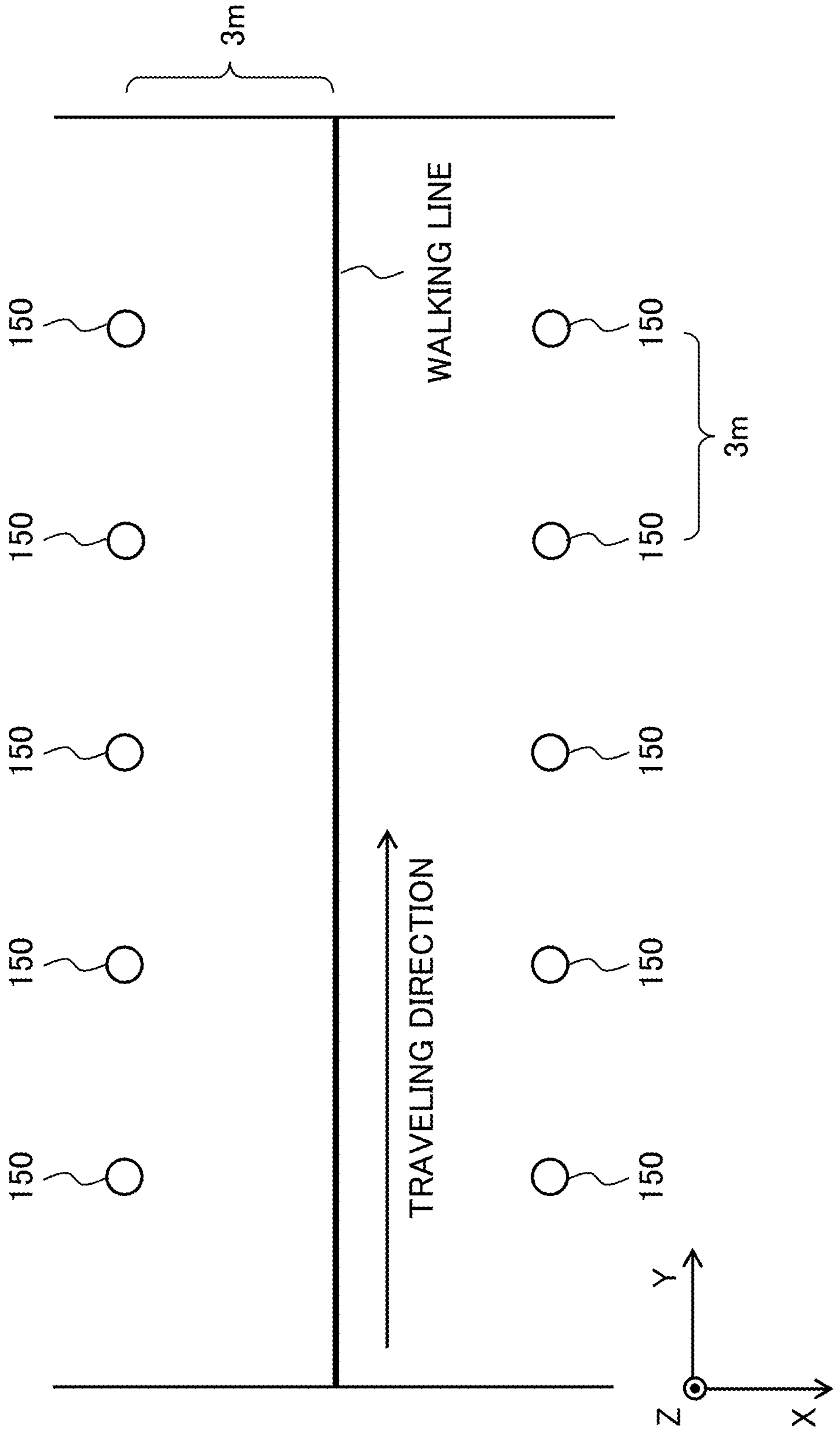
FIG. 10 is a conceptual diagram for describing arrangement of cameras for measuring the gait of a subject.

FIG. 10 is a conceptual diagram for explaining a walking line and positions at which a plurality of cameras 150 are arranged when the gait of the pedestrian wearing the shoe 100 to which the marks 131 and the mark 132 are attached is verified by motion capture. In this verification, five cameras 150 (ten cameras in total) were arranged on both sides across the walking line. Each of the plurality of cameras 150 was disposed at an interval of 3 m at a position of 3 m from the walking line. The height of each of the plurality of cameras 150 was fixed at a height of 2 m from a horizontal plane (XY plane). The focal point of each of the plurality of cameras 150 was aligned with the position of the walking line.

The movement of the mark 131 and the mark 132 installed on the shoe 100 of the pedestrian walking along the walking line was analyzed using the moving images captured by the plurality of cameras 150. The movement of the heel was verified by considering the plurality of marks 131 as one rigid body and analyzing the movement of the center of gravity of the marks. The movement of the toe was verified by analyzing the movement of the mark 132. In this verification, the heights of the heel and the toe in the direction of gravity (hereinafter, referred to as a Z-direction height), the positions of the toe and the heel in the traveling direction with respect to the central axis of the body (hereinafter, referred to as a Y-direction position), and the angle of the sole (roll angle) were measured by motion capture.

Figure 11:
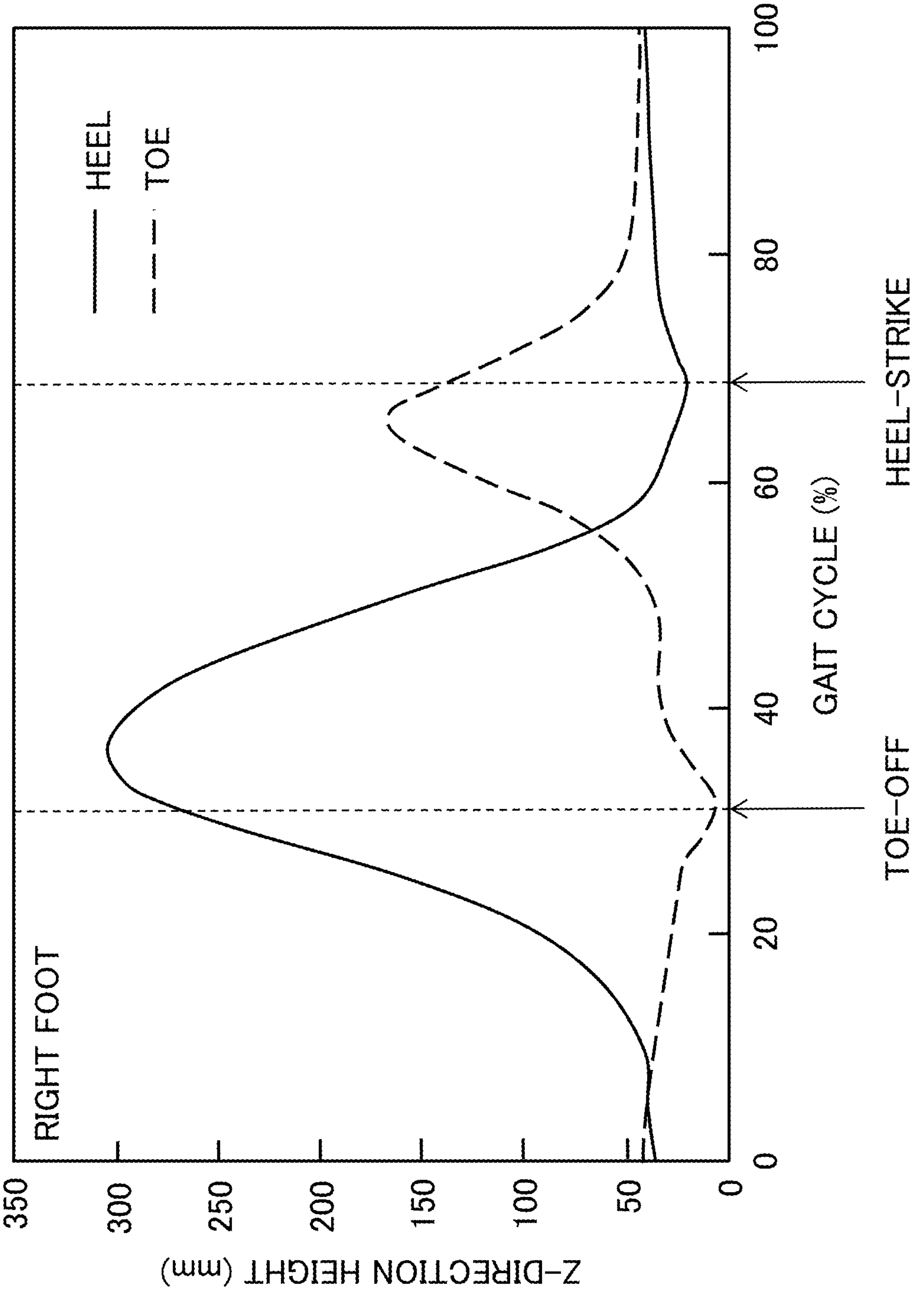
FIG. 11 is a graph of an example of time-series data of the Z-direction heights of the toe and the heel measured by motion capture.

FIG. 11 is a graph illustrating the gait cycle dependency of the Z-direction heights of the toe and heel of the right foot measured by motion capture. In FIG. 11, a change in the Z-direction height of the toe is indicated by a broken line, and a change in the Z-direction height of the heel is indicated by a solid line. The timing at which the height of the toe in the Z-direction becomes minimum is the timing of the toe-off. The timing at which the height of the heel in the Z-direction becomes minimum is the timing of the heel-strike.

Figure 12:
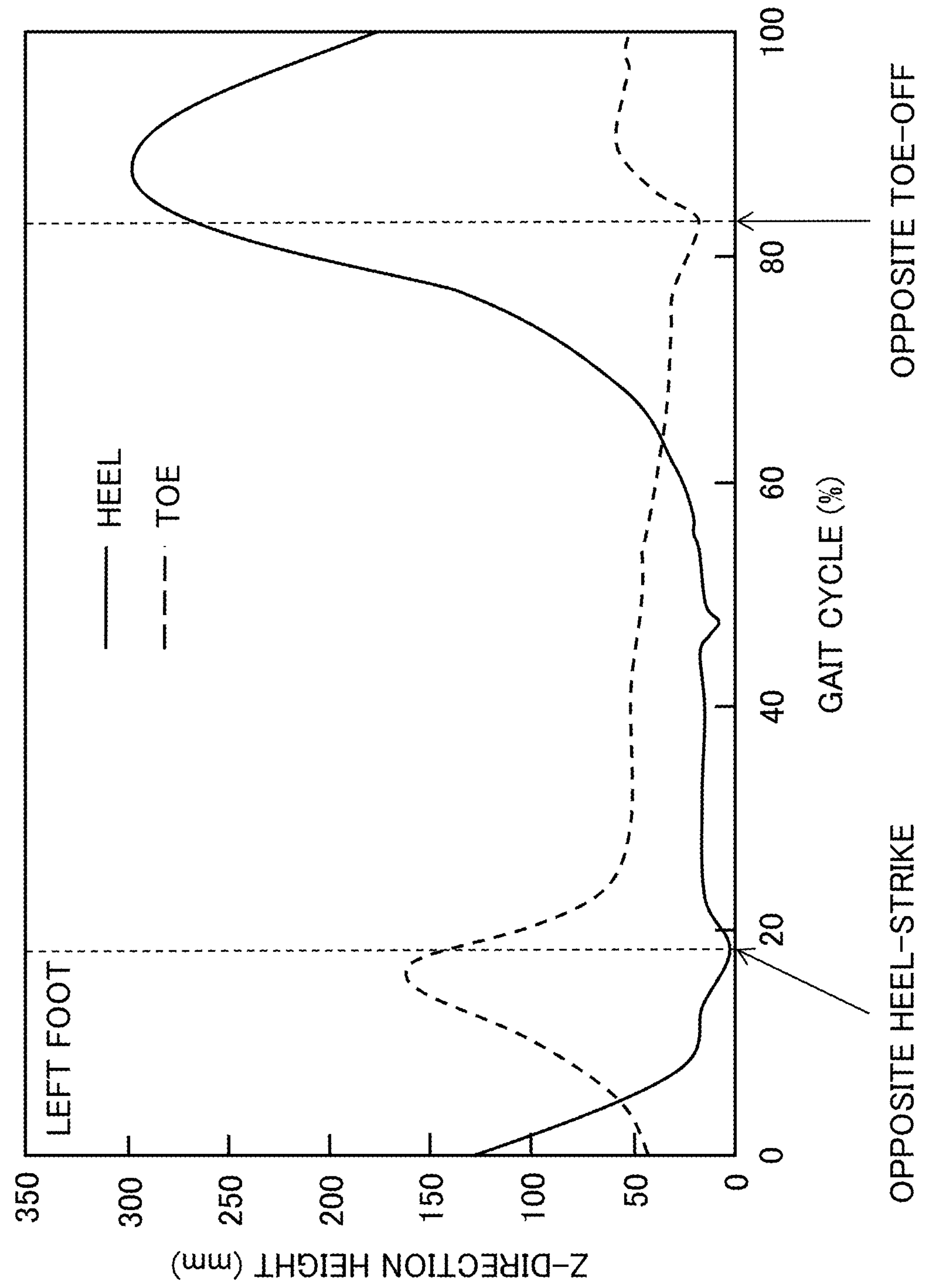
FIG. 12 is a graph of an example of time-series data of the Z-direction heights of the toe and the heel of the opposite foot measured by motion capture.

FIG. 12 is a graph illustrating the gait cycle dependency of the Z-direction heights of the toe and the heel of the left foot (opposite foot) measured by motion capture. In FIG. 12, a change in the Z-direction height of the toe is indicated by a broken line, and a change in the Z-direction height of the heel is indicated by a solid line. The timing at which the height of the toe in the Z-direction becomes minimum is the timing of the opposite toe-off. The timing at which the height of the heel in the Z-direction becomes minimum is the timing of the opposite heel-strike.

Hereinafter, an example in which the detection device 12 detects a gait event on the basis of the physical quantity related to the movement of the foot measured by the data acquisition device 11 will be described. In the following, description will be made along the order of detection of the gait event, not the order of time-series in the gait waveform of one gait cycle. Specifically, detection of toe-off, heel-strike, opposite heel-strike, opposite toe-off, tibia-vertical, foot-adjacent, and heel-rise will be described in order.

<Toe-Off>

First, the detection device 12 detects the timing of the toe-off from the gait waveform of the Y-direction acceleration for one gait cycle.

Figure 13:
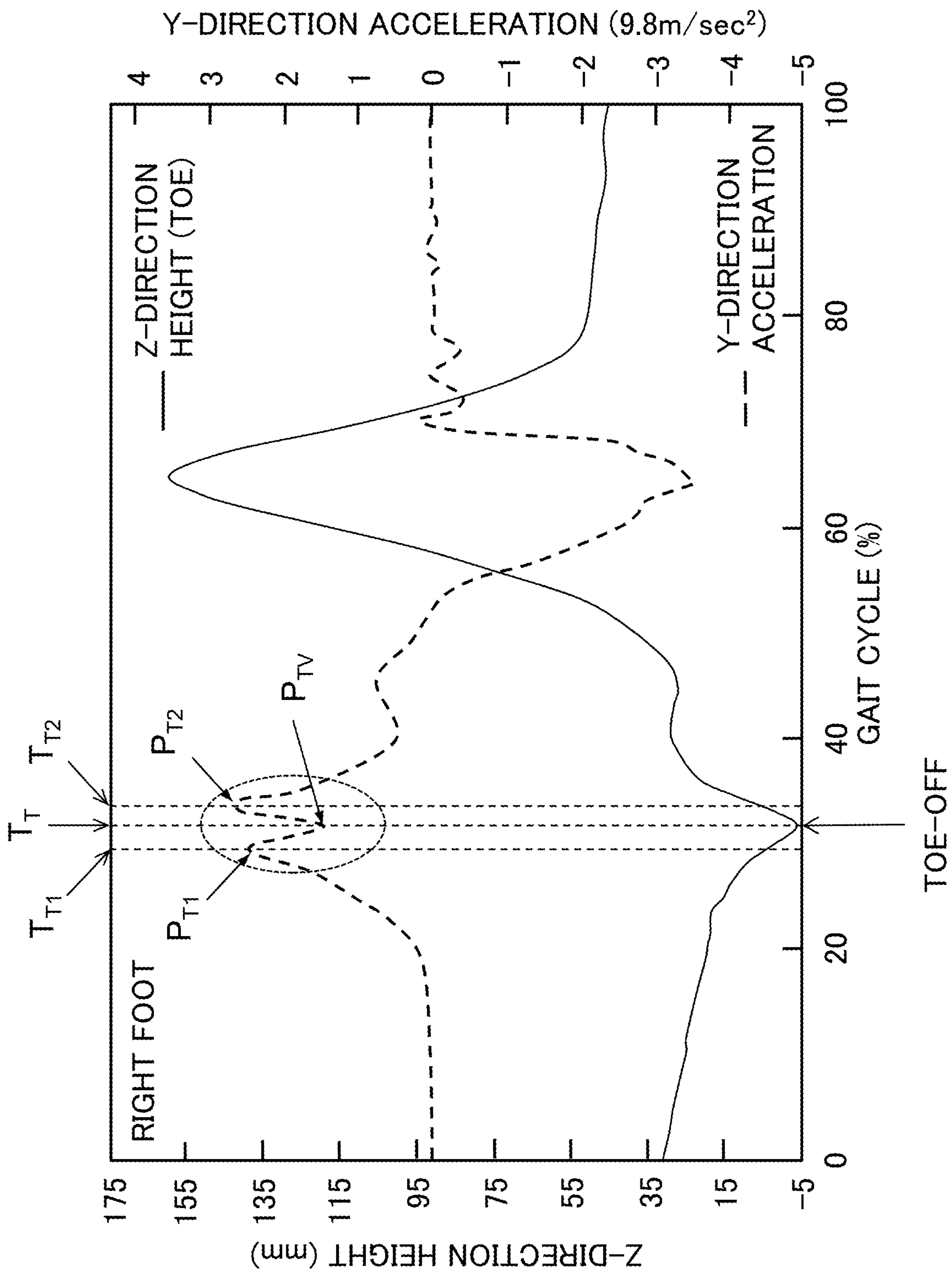
FIG. 13 is a graph for explaining an example in which the detection device of the detection system according to the first example embodiment detects the timing of the toe-off from the gait waveform of the acceleration in the traveling direction (Y-direction acceleration).

FIG. 13 is a graph in which the Z-direction height of the toe measured by motion capture is associated with the gait waveform of the Y-direction acceleration generated by the detection device 12 using the sensor data generated by the data acquisition device 11. The waveform of the Z-direction height of the toe measured by motion capture is indicated by a solid line. The gait waveform of the Y-direction acceleration generated by the detection device 12 is indicated by a broken line.

As shown in FIG. 13, in the Y-direction acceleration, two maximum peaks (peak $P_{T1}$, peak $P_{T2}$) and one minimum peak (peak $P_{TV}$) were detected at the maximum peak detected around 20 to 40% of the gait cycle (within a range surrounded by a dotted line). The timing of the toe-off corresponds to timing $T_T$ at which the peak $P_{TV}$ is detected between timing $T_{T1}$ at which the peak $P_{T1}$ is detected and timing $T_{T2}$ at which the peak $P_{T2}$ is detected.

In a case where thirty two subjects were set as a population, a root mean squared error (RMSE) of a regression line between the timing of the toe-off detected by the motion capture and the timing of the toe-off detected by the detection device 12 was 1.22%. That is, a sufficient correlation was confirmed between the timing of the toe-off detected by the motion capture and the timing of the toe-off detected by the detection device 12.

<Heel-Strike>

Next, the detection device 12 detects the timing of the heel-strike from the gait waveform of the Y-direction acceleration or the Z-direction acceleration for one gait cycle. Note that the order of detecting the toe-off and the heel-strike from the gait waveform for one gait cycle may be switched.

Figure 14:
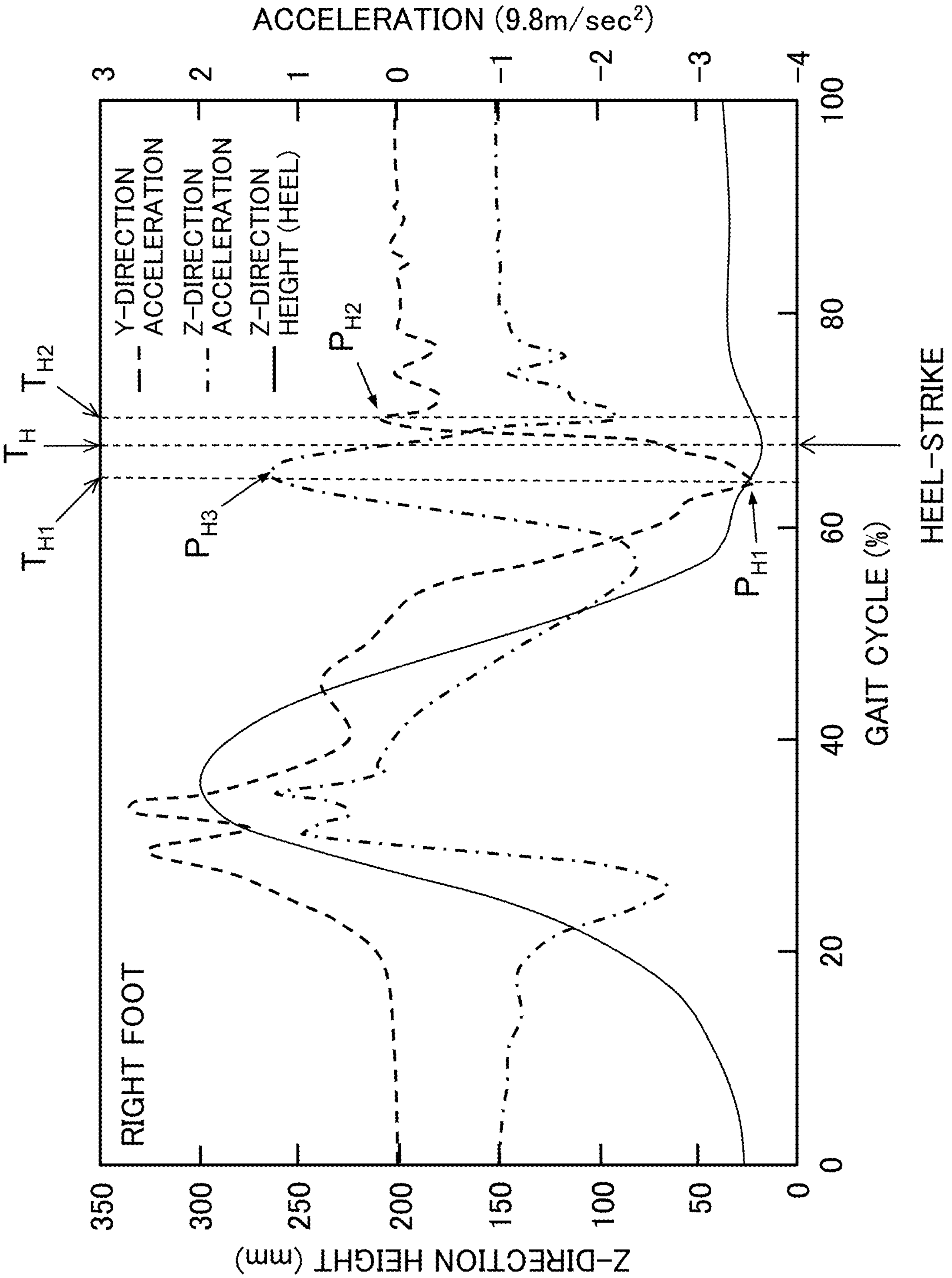
FIG. 14 is a graph for describing an example in which the detection device of the detection system according to the first example embodiment detects the timing of the heel-strike from a gait waveform of acceleration in the traveling direction (Y-direction acceleration) and a gait waveform of acceleration in the gravity direction (Z-direction height).

FIG. 14 is a graph in which the Z-direction height (left axis) of the heel measured by motion capture is associated with the gait waveform data (right axis) of the Y-direction acceleration and the Z-direction acceleration generated by the detection device 12 using the sensor data generated by the data acquisition device 11. The waveform of the Z-direction height of the heel measured by motion capture is indicated by a solid line. The gait waveform of the Y-direction acceleration measured by the detection device 12 is indicated by a broken line. The gait waveform of the Z-direction acceleration measured by the detection device 12 is indicated by a dashed line.

The timing at which the Z-direction height (solid line) of the heel measured by the motion capture becomes minimum corresponds to the timing of the heel-strike. However, a characteristic peak at the heel-strike does not appear in the Y-direction acceleration (broken line) and the Z-direction acceleration (dashed line). Therefore, in the present example embodiment, the timing of the heel-strike is specified using a characteristic peak appearing in the vicinity of the timing of the heel-strike.

As shown in FIG. 14, in the Y-direction acceleration (broken line), a minimum peak (peak $P_H$1) was detected around when the gait cycle exceeded 60%. The peak $P_H$1 corresponds to the timing of sudden deceleration of the foot at the terminal swing stage. In addition, in the Y-direction acceleration (broken line), a maximum peak $P_H$2 was detected around when the gait cycle is 70%. The peak $P_H$2 corresponds to the timing of the heel-rocker. When the data acquisition device 11 is installed at the position of the arch of foot, since the data acquisition device 11 is located on the toe side with respect to the rotation axis of the heel joint, an acceleration amount in the traveling direction (+Y-direction) is generated during the operation of the heel-rocker (rotation). Therefore, the period of the operation of the heel-rocker includes a period in which the acceleration in the gravity direction (Z-direction) is converted in the traveling direction (Y-direction) by the rotation along the outer periphery of the heel in contact with the ground after the heel-strike. As illustrated in FIG. 14, the timing of the heel-strike is included in the period from timing $T_{H1}$ at which the peak $P_{H1}$ is detected to timing $T_{H2}$ at which the peak $P_{H2}$ is detected. In the present example embodiment, timing $T_H$ at the midpoint between timing $T_{H1}$ at which the peak $P_{H1}$ is detected and timing $T_{H2}$ at which the peak $P_{H2}$ is detected is set as the timing of the heel-strike. The timing at which the peak $P_{H1}$ is detected in the Y-direction acceleration (broken line) substantially coincides with the timing at which the peak $P_{H3}$ is detected in the Z-direction acceleration (dashed line). Therefore, instead of timing $T_{H1}$ at which the peak $P_{H1}$ is detected in the Y-direction acceleration (broken line), the timing at which the peak $P_{H3}$ is detected in the Z-direction acceleration (dashed line) may be used as the timing of the sudden deceleration of the leg the terminal swing stage.

In a case where thirty two subjects were set as a population, the RMS of a regression line between the timing of the heel-strike detected by motion capture and the timing of the heel-strike detected by the detection device 12 was 1.40%. That is, a sufficient correlation was confirmed between the timing of the toe-off detected by the motion capture and the timing of the toe-off detected by the detection device 12.

<Opposite Heel-Strike>

Next, the detection device 12 detects the timing of the opposite heel-strike from the gait waveform of the roll angular velocity for one gait cycle. The detection device 12 detects an opposite heel-strike using a triangle thresholding algorithm. For example, the detection device 12 detects the opposite heel-strike from the first gait waveform W1 from the start point of one gait cycle to the toe-off.

Figure 15:
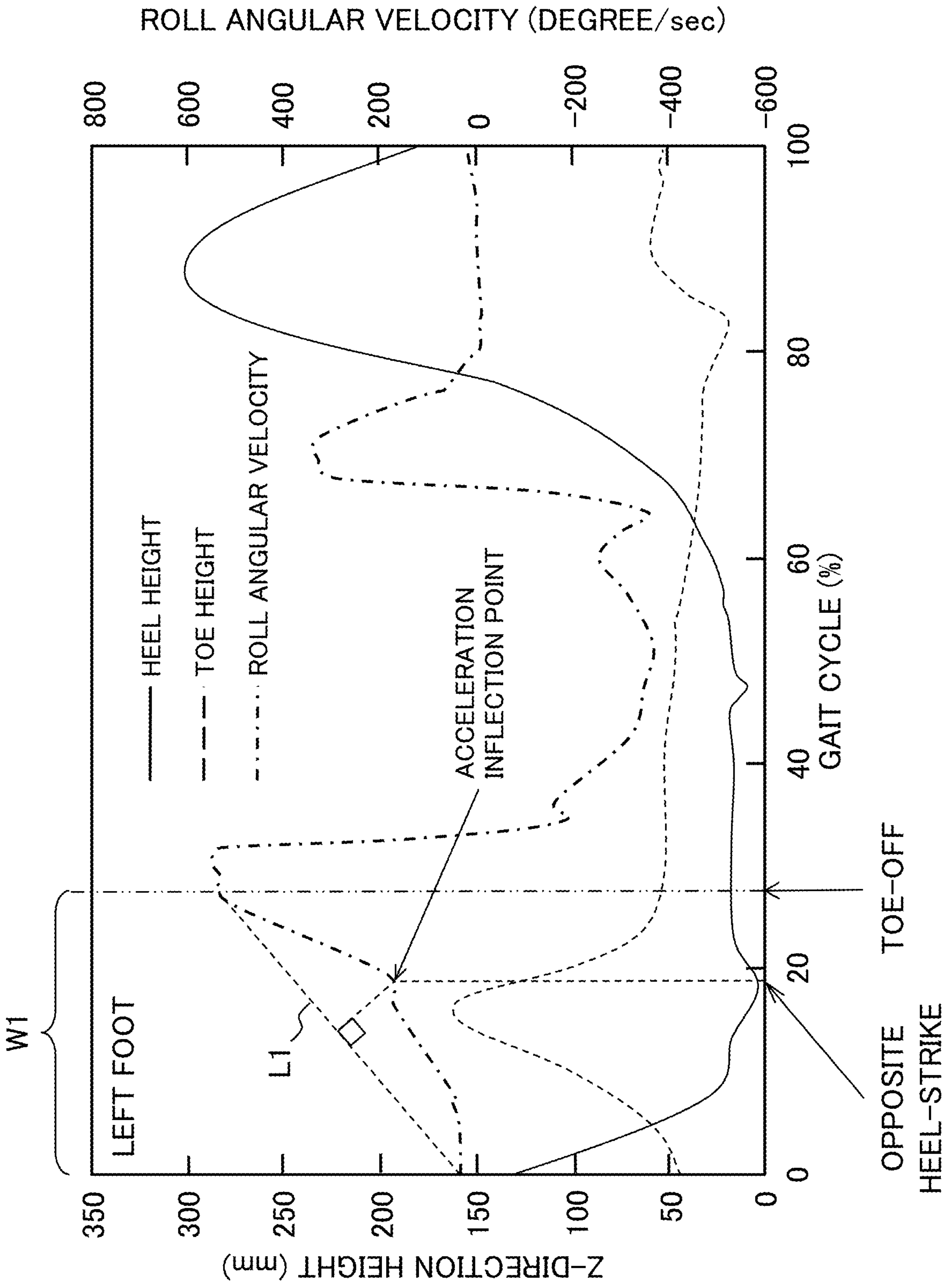
FIG. 15 is a graph for describing an example in which the detection device of the detection system according to the first example embodiment detects the timing of the opposite heel-strike from the gait waveform of the roll angular velocity.

FIG. 15 is a graph in which the Z-direction height (left axis) of the heel measured by motion capture is associated with the gait waveform (right axis) of the roll angular velocity measured by the detection device 12 using the sensor data generated by the data acquisition device 11. The waveform of the Z-direction height of the heel measured by motion capture is indicated by a solid line. The waveform of the Z-direction height of the toe measured by motion capture is indicated by a broken line. A walking change in the roll angular velocity measured by the detection device 12 is indicated by a dashed line.

The heel-strike of the left foot (opposite heel-strike) occurs immediately before the toe-off of the right foot. When the heel of the left foot touches the ground, a double-leg support state by both right and left feet is created. At this time, since the left foot provides a fulcrum of kicking of the right foot, the kicking speed of the right foot increases, and the rotation speed of the right foot is accelerated. Therefore, the timing of the opposite heel-strike corresponds to the timing of the acceleration inflection point in the first gait waveform W1 of the roll angular velocity. In the gait waveform of the roll angular velocity, the detection unit 123 obtains, as an acceleration inflection point, a point at which the length of a perpendicular line drawn from a line segment L1 connecting the start point (0%) of one gait cycle and the peak of the toe-off toward the gait waveform of the roll angular velocity becomes maximum. The detection unit 123 detects the timing of the acceleration inflection point in the first gait waveform W1 of the roll angular velocity as the timing of the opposite heel-strike.

In a case where thirty two subjects were set as a population, the RMSE of a regression line between the timing of the opposite heel-strike detected by motion capture and the timing of the opposite heel-strike detected by the detection device 12 was 2.41%. That is, a correlation was confirmed between the timing of the opposite heel-strike detected by the motion capture and the timing of the opposite heel-strike detected by the detection device 12.

<Opposite Toe-Off>

Next, the detection device 12 detects the timing of the opposite toe-off from the gait waveform of the roll angular velocity for one gait cycle. The detection device 12 detects an opposite toe-off using a triangle thresholding algorithm. For example, the detection device 12 detects the opposite toe-off from the third gait waveform W3 from the heel-strike to the end point of one gait cycle. Note that the order of detecting the opposite toe-off and the opposite heel-strike from the gait waveform for one gait cycle may be switched.

Figure 16:
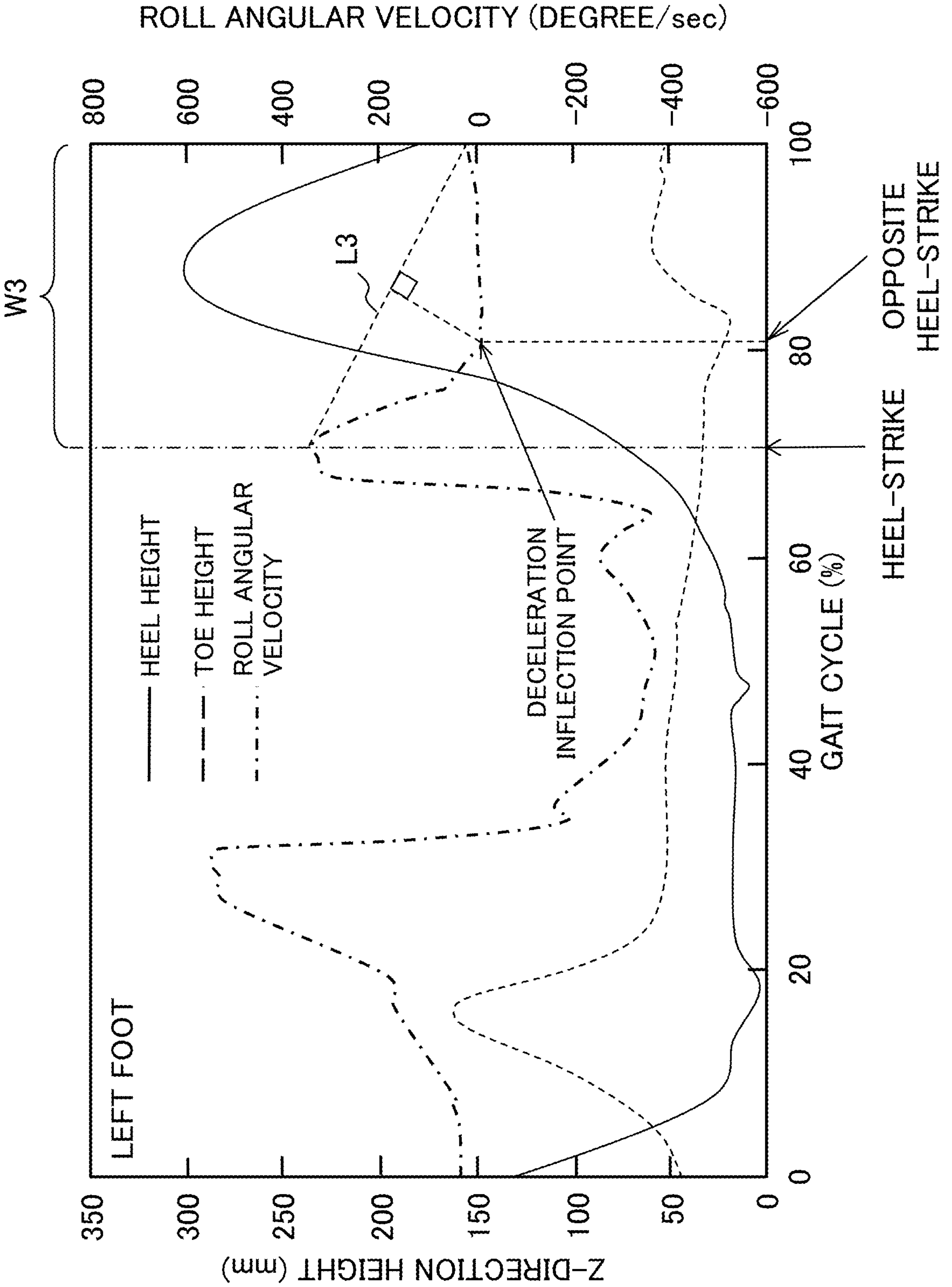
FIG. 16 is a graph for describing an example in which the detection device of the detection system according to the first example embodiment detects the timing of the opposite toe-off from the gait waveform of the roll angular velocity.

FIG. 16 is a graph in which the Z-direction height (left axis) of the heel measured by motion capture is associated with the gait waveform data (right axis) of the roll angular velocity measured by the detection device 12 using the sensor data generated by the data acquisition device 11. A change in the Z-direction height of the heel measured by motion capture is indicated by a solid line. A change in the Z-direction height of the toe measured by motion capture is indicated by a broken line. A change in the roll angular velocity measured by the detection device 12 is indicated by a dashed line.

The toe-off of the left foot (opposite toe-off) occurs immediately after the heel-strike of the right foot. If the right foot does not completely land on the ground, the left foot is not stably kicked out. Therefore, when the rotation of the right foot is completely ended, kicking of the left foot occurs. Therefore, the timing of the opposite toe-off corresponds to the timing of the deceleration inflection point in the third gait waveform W3 of the roll angular velocity. In the gait waveform of the roll angular velocity, the detection unit 123 obtains, as the deceleration inflection point, a point at which the length of a perpendicular line drawn from a line segment L3 connecting the peak of the heel-strike and the end point (100%) of one gait cycle toward the gait waveform of the roll angular velocity becomes maximum. The detection unit 123 detects the timing of the deceleration inflection point in the third gait waveform W3 of the roll angular velocity as the timing of the opposite toe-off.

In a case where thirty two subjects were set as a population, the RMSE of a regression line between the timing of the opposite toe-off detected by the motion capture and the timing of the opposite toe-off detected by the detection device 12 was 1.98%. That is, a correlation was confirmed between the timing of the opposite heel-strike detected by the motion capture and the timing of the opposite heel-strike detected by the detection device 12.

<Tibia-Vertical>

Next, the detection device 12 detects the timing of the tibia-vertical from the gait waveform of the Z-direction acceleration for one gait cycle. For example, the detection device 12 detects the tibia-vertical from the second gait waveform W2 from the toe-off to the heel-strike. Note that the order of detecting the tibia-vertical from the gait waveform for one gait cycle may be before the opposite toe-off and the opposite heel-strike.

Figure 17:
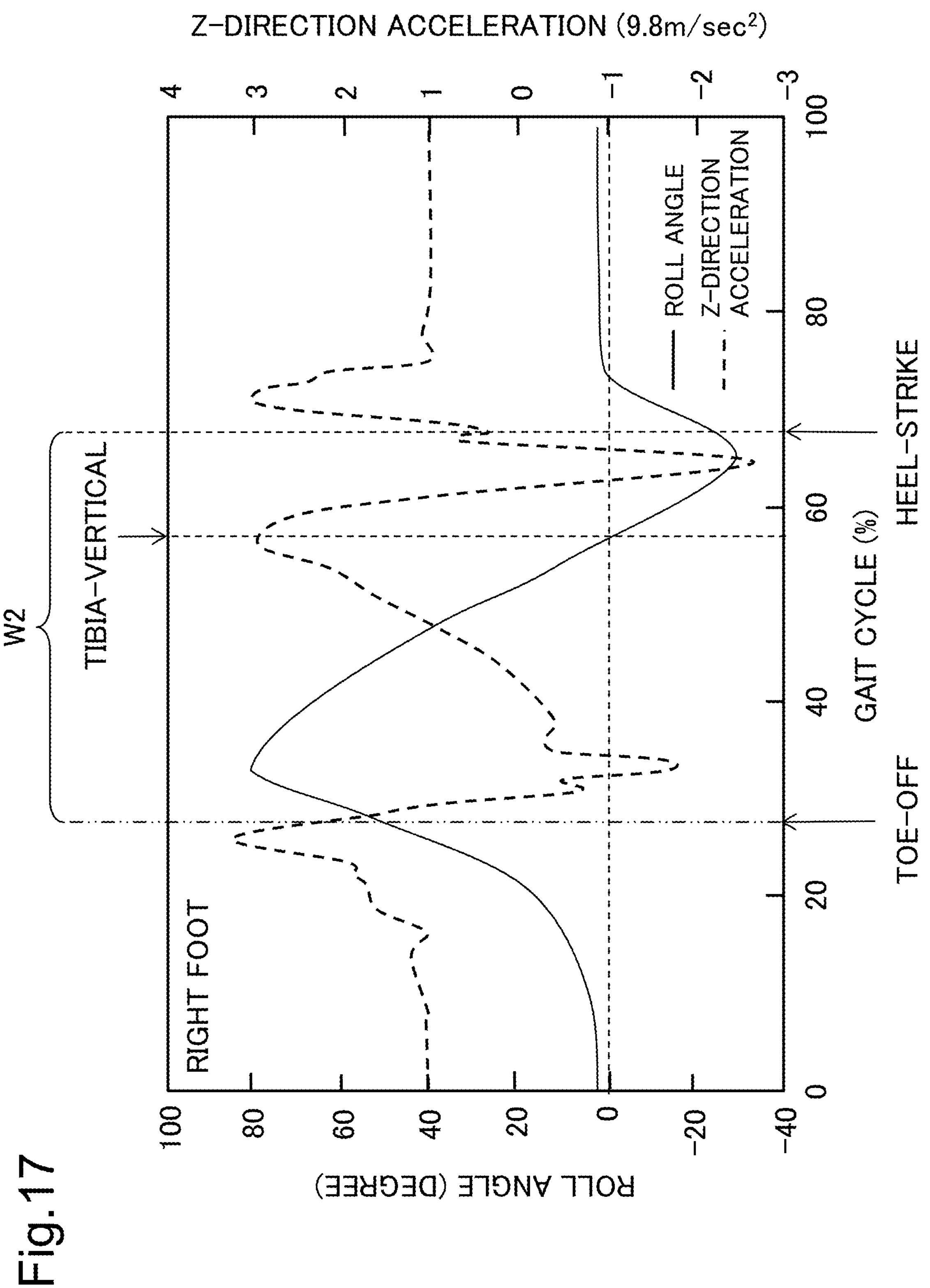
FIG. 17 is a graph for describing an example in which the detection device of the detection system according to the first example embodiment detects the timing of the tibia-vertical from the gait waveform of the acceleration in the gravity direction (Z-direction height).

FIG. 17 is a graph in which the waveform of the roll angle (left axis) measured by motion capture is associated with the gait waveform (right axis) of the Z-direction acceleration generated by the detection device 12 using the sensor data generated by the data acquisition device 11. The waveform of the roll angle measured by motion capture is indicated by a solid line. A gait waveform of the Z-direction acceleration generated by the detection device 12 is indicated by a broken line.

The tibia-vertical is the state where the tibia is approximately vertical to the ground. In the tibia-vertical, the heel joint is in a neutral state and the sole of the foot is vertical to the tibia. That is, in the tibia-vertical, the roll angle associated with the rotation of the heel joint becomes 0 degrees. As illustrated in FIG. 17, the peak of the gait waveform of the Z-direction acceleration becomes maximum at the timing when the roll angle measured by motion capture is 0 degrees. That is, the tibia-vertical corresponds to the timing of the maximum value in the second gait waveform W2 between the toe-off and the heel-strike cut out from the gait waveform of the Z-direction acceleration. The detection unit 123 detects the timing at which the peak generated in the second gait waveform W2 cut out from the gait waveform of the Z-direction acceleration becomes maximum as the timing of the tibia-vertical.

In a case where thirty two subjects were set as a population, the RMSE of a regression line between the timing of the tibia-vertical detected by motion capture and the timing of the tibia-vertical detected by the detection device 12 was 1.85%. That is, a correlation was confirmed between the timing of the tibia-vertical detected by the motion capture and the timing of the tibia-vertical detected by the detection device 12.

<Foot-Adjacent>

Next, the detection device 12 detects the timing of the foot-adjacent from the gait waveform of the Y-direction acceleration for one gait cycle. For example, the detection device 12 detects the foot-adjacent from a gait waveform from the toe-off to the tibia-vertical (also referred to as a fourth gait waveform W4).

Figure 18:
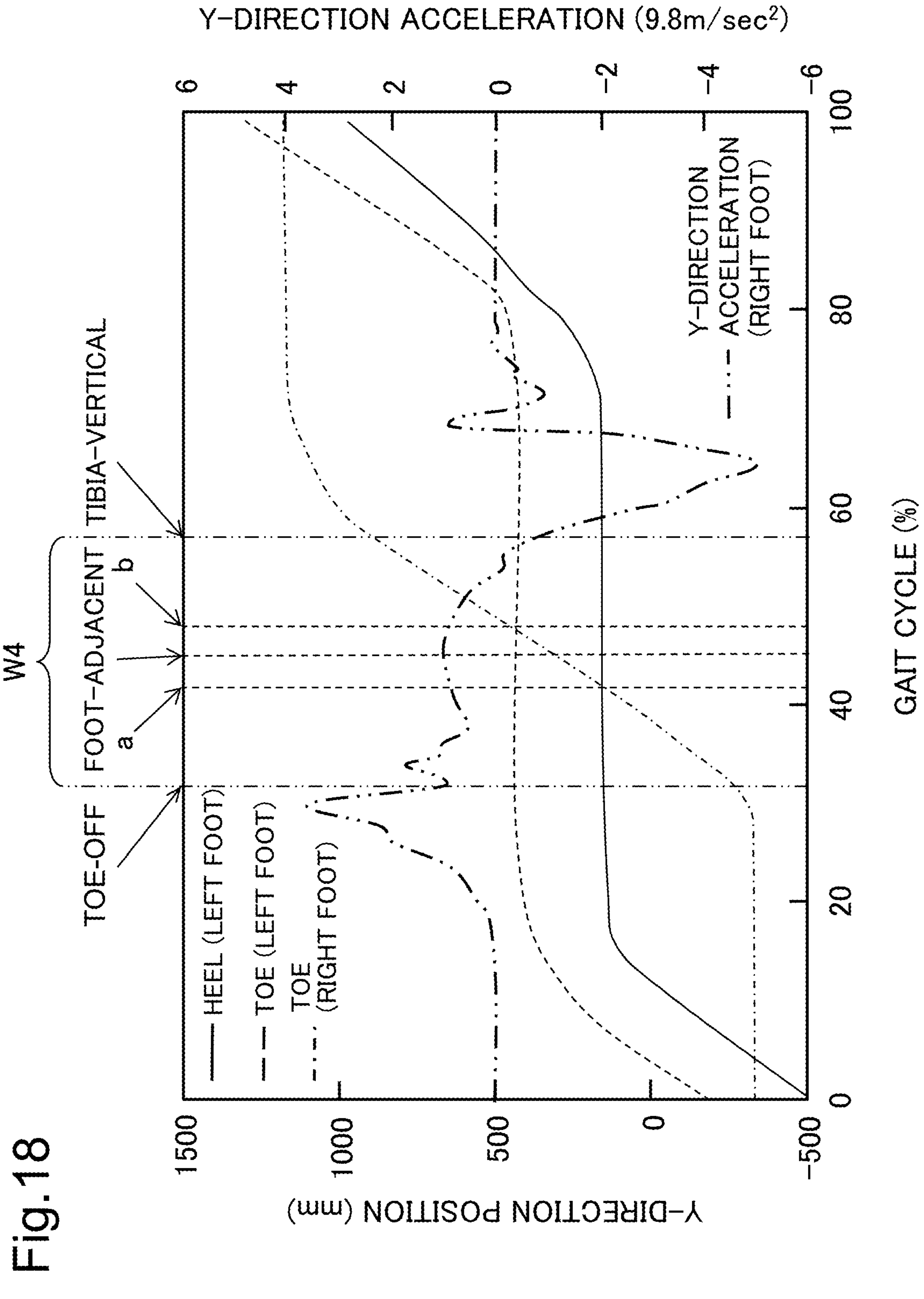
FIG. 18 is a graph for explaining an example in which the detection device of the detection system according to the first example embodiment detects the timing of the foot-adjacent from the gait waveform of the acceleration in the traveling direction (Y-direction acceleration).

FIG. 18 is a graph in which waveforms of the Y-direction positions (left axis) of the heel and the toe of the left foot and the toe of the right foot measured by motion capture are associated with the gait waveform (right axis) of the Y-direction acceleration generated by the detection device 12 using the sensor data generated by the data acquisition device 11. The waveform of the Y-direction position of the heel of the left foot measured by motion capture is indicated by a solid line. The waveform of the Y-direction position of the toe of the left foot measured by motion capture is indicated by a broken line. The waveform of the Y-direction position of the toe of the right foot measured by motion capture is indicated by a dashed line. The gait waveform of the Y-direction acceleration generated by the detection device 12 is indicated by a double-dotted line.

In the present example embodiment, in a state where the left foot in contact with the ground is in the front of the right foot, the timing at which the toe of the right foot passes the position of the heel of the left foot is defined as a, and the timing at which the toe of the right foot passes the position of the toe of the left foot is defined as b. The center timing between the timing a and the timing b is defined as the timing of the foot-adjacent. As illustrated in FIG. 18, the timing of the foot-adjacent corresponds to the timing of the maximum value of the gentle peak on the side close to the tibia-vertical in the fourth gait waveform W4 between the tibia-vertical and the toe-off, which is cut out from the gait waveform of the Y-direction acceleration. The detection unit 123 detects the timing at which the gentle peak on the side close to the tibia-vertical becomes maximum in the fourth gait waveform W4 of the Y-direction acceleration as the timing of the foot-adjacent.

In a case where thirty two subjects were set as a population, the RMSE of a regression line between the foot-adjacent detected by the motion capture and the timing of the foot-adjacent detected by the detection device 12 was 2.02%. That is, a correlation was confirmed between the timing of the foot-adjacent detected by the motion capture and the timing of the foot-adjacent detected by the detection device 12.

<Heel-Rise>

Next, the detection device 12 detects the timing of the heel-rise from the gait waveform of the roll angular velocity for two consecutive gait cycles. The detection device 12 detects the timing of the heel-rise using the triangle thresholding algorithm. For example, the detection device 12 detects the heel-rise from a gait waveform (also referred to as a fifth gait waveform W5) from an opposite toe-off in one gait cycle (first gait cycle) to an opposite heel-strike in two gait cycles (second gait cycle) in a gait waveform of two gait cycles.

Figure 19:
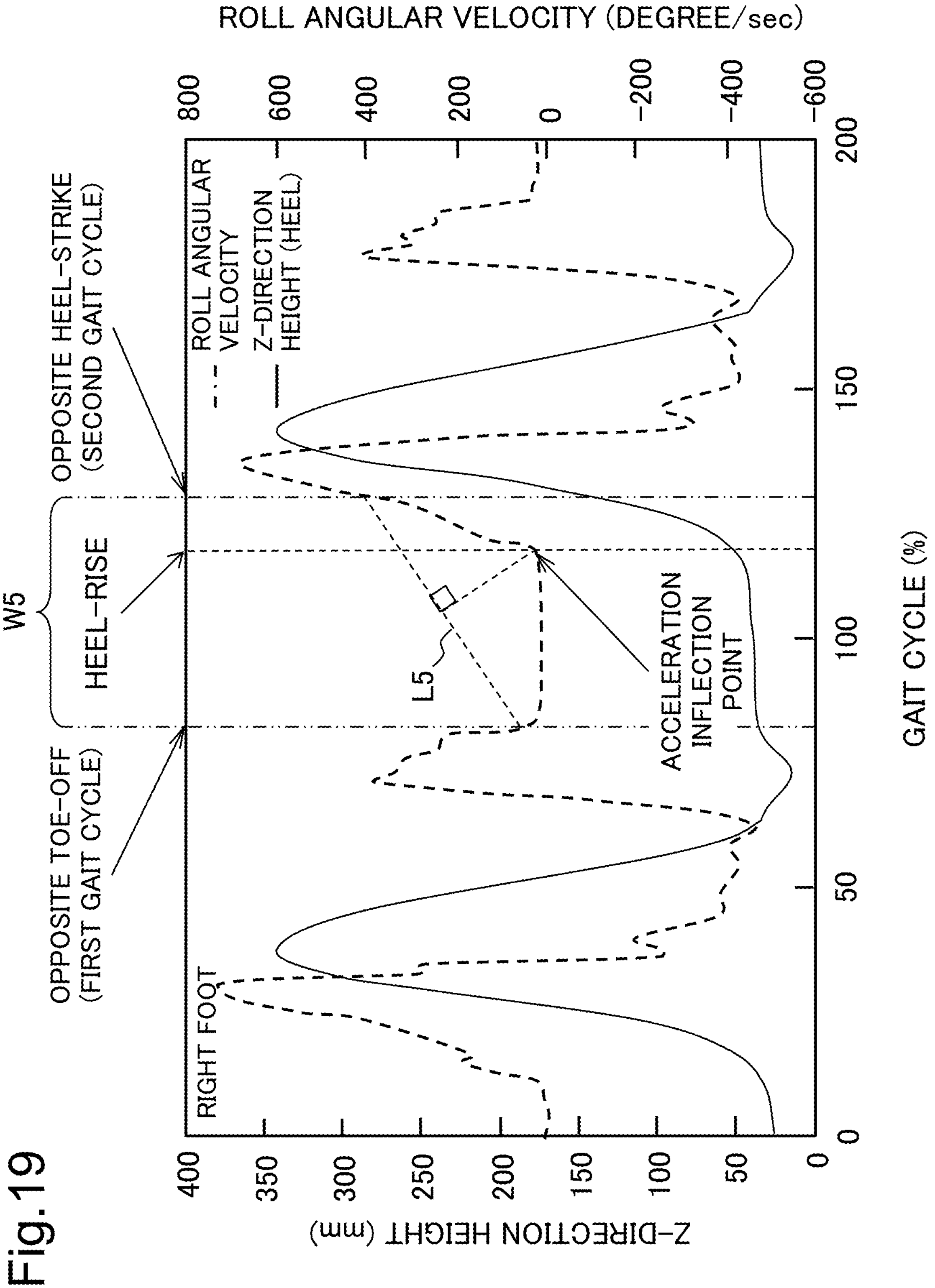
FIG. 19 is a graph for explaining an example in which the detection device of the detection system according to the first example embodiment detects the timing of a heel-rise from the gait waveform of the roll angular velocity.

FIG. 19 is a graph in which the Z-direction height (left axis) of the heel measured by motion capture is associated with the gait waveform data (right axis) of the roll angular velocity generated by the detection device 12 using the sensor data generated by the data acquisition device 11. The waveform of the Z-direction height of the heel measured by motion capture is indicated by a solid line. A gait waveform of the roll angular velocity measured by the detection device 12 is indicated by a broken line.

In the heel-rise, the heel of the right foot in contact with the ground starts to be displaced in the Z-direction. When the heel of the right foot in contact with the ground starts to be displaced in the Z-direction, a change occurs in the roll angular velocity. The heel-rise corresponds to the timing of the acceleration inflection point in the fifth gait waveform W5 between the opposite toe-off in the first gait cycle and the opposite heel-strike in the second gait cycle, which is cut out from the gait waveform of the roll angular velocity. In the fifth gait waveform W5, the detection unit 123 obtains, as an acceleration inflection point, a point at which the length of a perpendicular line drawn from a line segment connecting the timing of the opposite toe-off in the first gait cycle and the timing of the opposite heel-strike in the second gait cycle toward the gait waveform of the roll angular velocity becomes maximum. The detection unit 123 detects the timing of the acceleration inflection point in the fifth gait waveform W5 of the roll angular velocity as the timing of the heel-rise.

In a case where thirty two subjects were set as a population, the RMSE of a regression line between the timing of the heel-rise detected by motion capture and the timing of the heel-rise detected by the detection device 12 was 4.49%. That is, although the RMSE was larger than that of other gait events, a correlation was confirmed between the timing of the opposite heel-rise detected by the motion capture and the timing of the heel-rise detected by the detection device 12.

As described with reference to FIGS. 13 to 19, the detection unit 123 generates a gait waveform from the sensor data based on the physical quantity related to the movement of the foot measured by the data acquisition device 11, and detects the timing of a gait event from the generated gait waveform. If the timing of the gait event can be specified, the movement of the foot, the angle of the foot, the force applied to the foot, and the like at each timing can be verified. In addition, if the time at which the gait event occurs is specified, the ratio between the single-support period and the double-support period, the ratio between the stance phase and the swing phase, the asymmetry of walking, and the like can be verified. For example, the timing of the gait event detected by the detection unit 123 may be output to another system, a display device, or the like (not illustrated). The timing of the gait event detected by the detection unit 123 can be applied to various uses for measuring the gait and various uses for estimating the physical condition on the basis of the gait.

(Operation)

Next, the operation of the detection device 12 of the detection system 1 of the present example embodiment will be described with reference to the drawings. Hereinafter, the extraction unit 121 and the detection unit 123 of the detection device 12 are regarded as the subject of operation. Note that the subject of operation described below may be the detection device 12.

Figure 20:
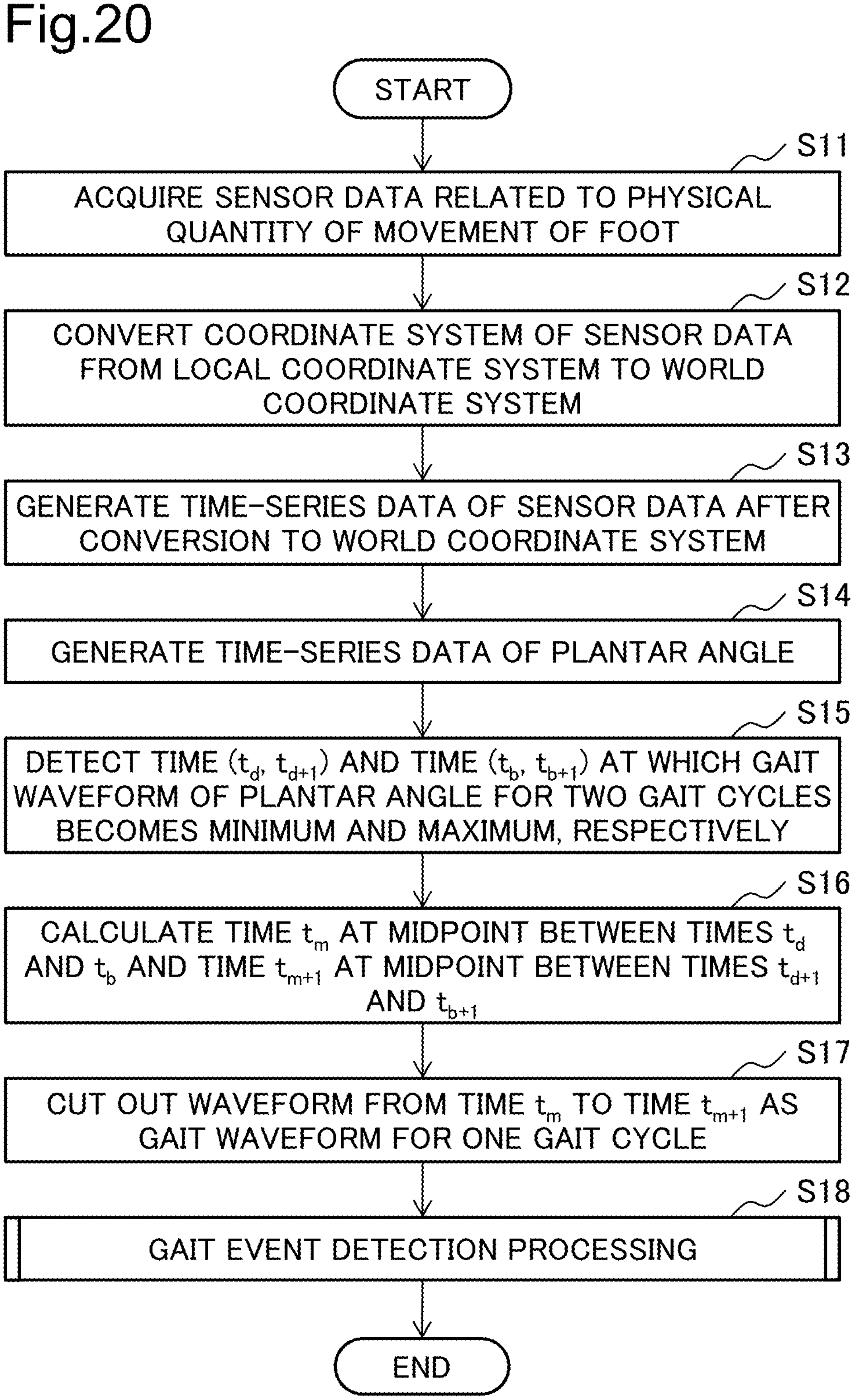
FIG. 20 is a flowchart for explaining an example of the operation of the detection device according to the first example embodiment.

First, the operation of the extraction unit 121 will be described with reference to the drawings. FIG. 20 is a flowchart for explaining an example of operations of the extraction unit 121 and the detection unit 123.

In FIG. 20, first, the extraction unit 121 acquires, from the data acquisition device 11, sensor data related to the physical quantity of the movement of the foot of the pedestrian walking in the footwear on which the data acquisition device 11 is installed (step S11). The extraction unit 121 acquires sensor data in a local coordinate system of the data acquisition device 11. For example, the extraction unit 121 acquires a three-dimensional spatial acceleration and a three-dimensional spatial angular velocity from the data acquisition device 11 as sensor data related to the movement of the foot.

Next, the extraction unit 121 converts the coordinate system of the sensor data from the local coordinate system of the data acquisition device 11 to the world coordinate system (step S12).

Next, the extraction unit 121 generates time-series data of the sensor data after conversion to the world coordinate system (step S13).

Next, the extraction unit 121 calculates a spatial angle (plantar angle) using at least one of the spatial acceleration and the spatial angular velocity, and generates time-series data of the plantar angle (step S14). The extraction unit 121 generates time-series data of the spatial velocity and the spatial trajectory as necessary.

Next, the extraction unit 121 detects a time (time $t_d$, time $t_{d+1}$) and a time (time $t_b$, time $t_{b+1}$) at which the gait waveform of the plantar angle for two gait cycles become minimum and maximum, respectively (step S15).

Next, the extraction unit 121 calculates time $t_m$ at the midpoint between time $t_d$ and time $t_b$ and time $t_{m+1}$ at the midpoint between time $t_{d+1}$ and time $t_{b+1}$ (step S16).

Next, the extraction unit 121 cuts out a waveform from time $t_m$ to time $t_{m+1}$ as a gait waveform for one gait cycle (step S17).

Then, the detection unit 123 executes gait event detection processing of detecting a gait event from the gait waveform for one gait cycle cut out by the extraction unit (step S18).

[Gait Event Detection Processing]

Figure 21:
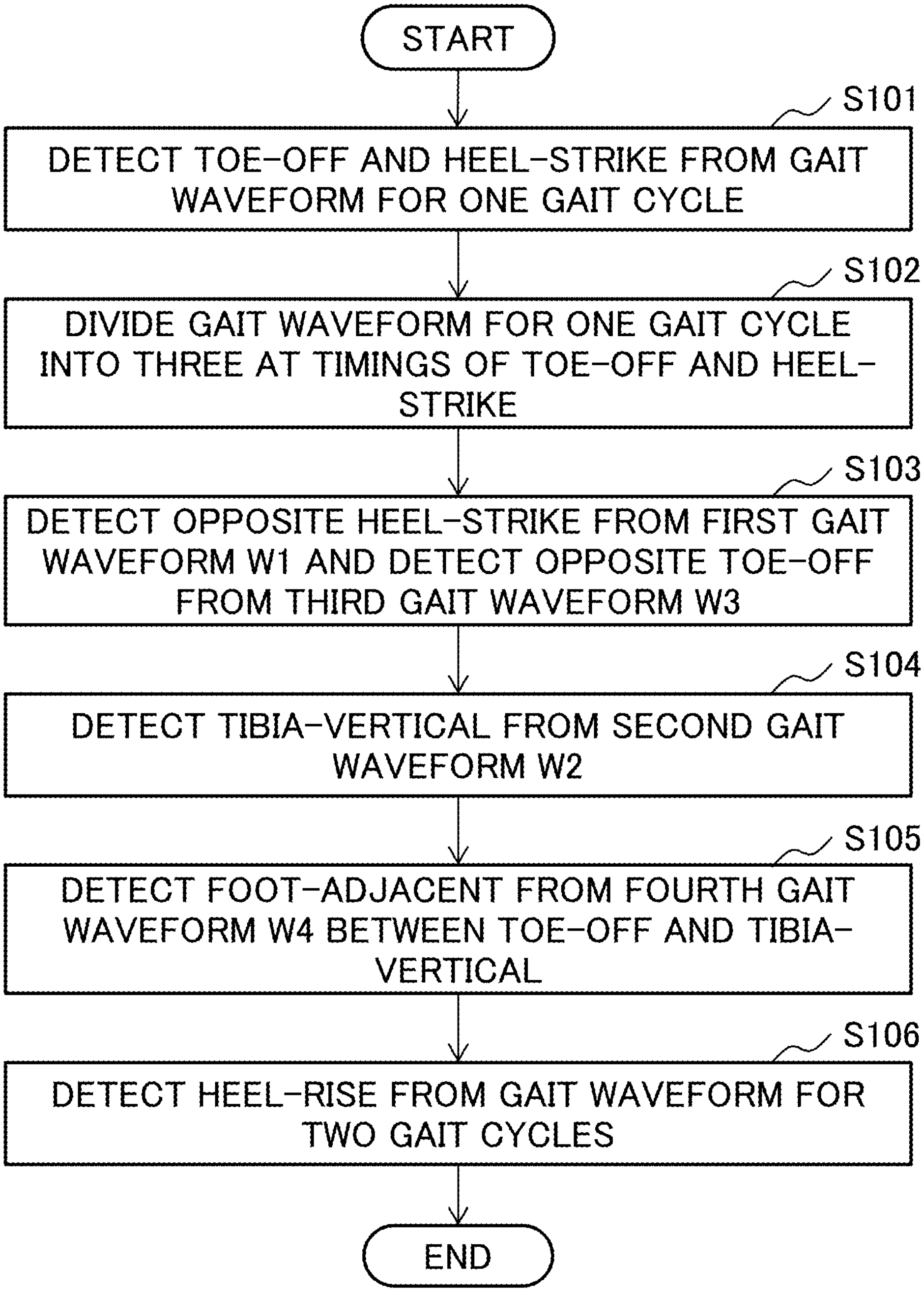
FIG. 21 is a flowchart for explaining an example of gait event detection processing of the detection device according to the first example embodiment.

Next, an outline of gait event detection processing (step S18 in FIG. 20) of the detection unit 123 will be described with reference to the drawings. FIG. 21 is a flowchart for explaining an example of gait event detection processing of the detection unit 123. The flowchart of FIG. 21 is schematic, and detection of individual gait events will be sequentially described.

In FIG. 21, first, the detection unit 123 detects the toe-off and the heel-strike from the gait waveform for one gait cycle (step S101). For example, the detection unit 123 detects the toe-off and the heel-strike from the gait waveform of the Y-direction acceleration for one gait cycle.

Next, the detection unit 123 divides the gait waveform of one gait cycle into three at the timings of the toe-off and the heel-strike (step S102). For example, the detection unit 123 divides the gait waveform used for detection of the gait event into a first gait waveform W1 from the start point of one gait cycle to the toe-off, a second gait waveform W2 from the toe-off to the heel-strike, and a third gait waveform W3 from the heel-strike to the end point of one gait cycle.

Next, the detection unit 123 detects an opposite heel-strike from the first gait waveform W1 and detects an opposite toe-off from the third gait waveform W3 (step S103). For example, in the gait waveform of the roll angular velocity, the detection unit 123 detects the opposite heel-strike from the first gait waveform W1, and detects the opposite toe-off from the third gait waveform W3.

Next, the detection unit 123 detects the tibia-vertical from the second gait waveform W2 (step S104). For example, the detection unit 123 detects the tibia-vertical from the second gait waveform W2 of the Z-direction acceleration.

Next, the detection unit 123 detects the foot-adjacent from the fourth gait waveform W4 between the toe-off and the tibia-vertical (step S105). For example, the detection unit 123 detects the foot-adjacent from the fourth gait waveform W4 of the Y-direction acceleration.

Next, the detection unit 123 detects the heel-rise from the gait waveform corresponding to the two gait cycles (step S106). For example, the detection unit 123 detects the heel-rise from the fifth gait waveform W5 from the opposite toe-off in the first gait cycle to the opposite heel-strike in the second gait cycle in the gait waveform for two gait cycles.

<Toe-Off>

Figure 22:
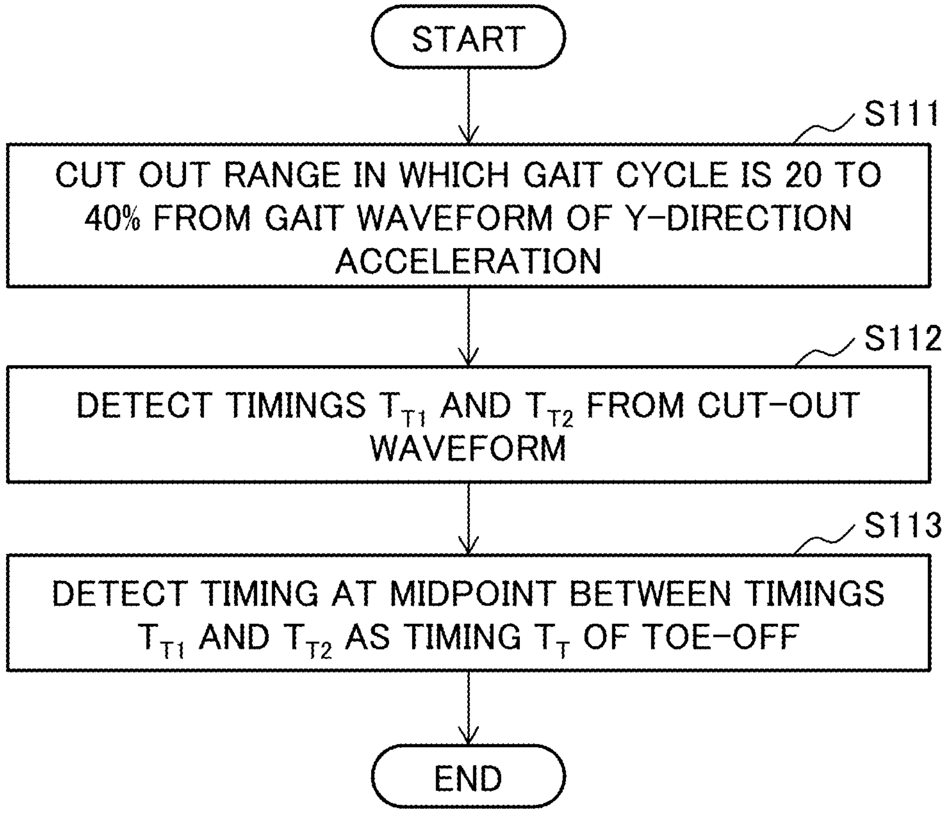
FIG. 22 is a flowchart for explaining an example of detection of a toe-off by the detection device according to the first example embodiment.

Next, an algorithm for detecting the toe-off will be described with reference to the drawings. FIG. 22 is a flowchart for describing an example of an algorithm for detecting the toe-off. The toe-off corresponds to the start timing of the swing phase.

In FIG. 22, first, the detection unit 123 cuts out a range of 20 to 40% of the gait cycle from the gait waveform of the Y-direction acceleration (step S111).

Next, the detection unit 123 detects the maximum timing $T_{T1}$ and the maximum timing $T_{T2}$ from the cut-out waveforms (step S112).

Then, the detection unit 123 detects the timing at the midpoint between timing $T_{T1}$ and timing $T_{T2}$ as timing $T_T$ of the toe-off (step S113).

<Heel-Strike>

Figure 23:
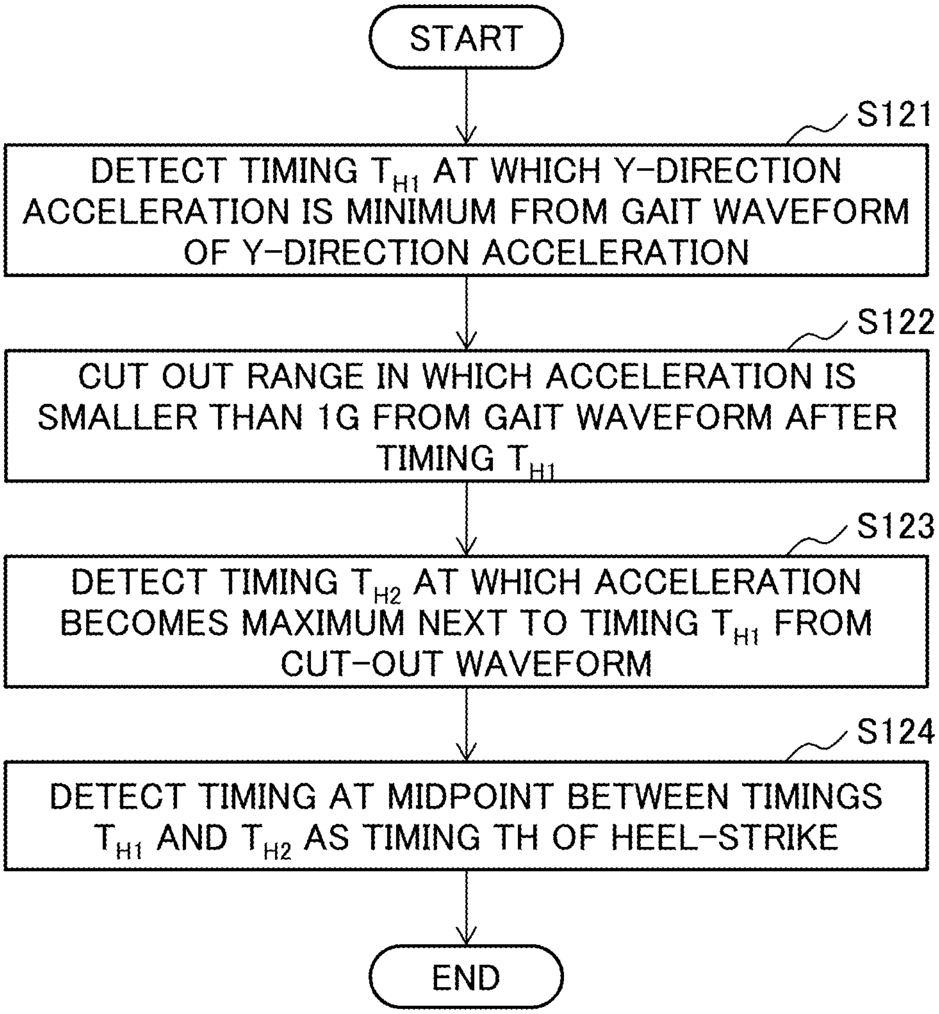
FIG. 23 is a flowchart for explaining an example of detection of a heel-strike by the detection device according to the first example embodiment.

Next, an example of an algorithm for detecting the heel-strike will be described with reference to the drawings. FIG. 23 is a flowchart for explaining an example of an algorithm for detecting the heel-strike. The heel-strike corresponds to the start timing of the stance phase.

In FIG. 23, first, the detection unit 123 detects timing $T_{H1}$ at which the Y-direction acceleration becomes minimum from the gait waveform of the Y-direction acceleration (step S121).

Next, the detection unit 123 cuts out a range in which the value of the Y-direction acceleration becomes smaller than 1 G after timing $T_{H1}$ from the gait waveform of the Y-direction acceleration (step S122).

Next, the detection unit 123 detects a timing $T_{H1}$ at which the Y-direction acceleration becomes minimum and a timing $T_{H2}$ at which the Y-direction acceleration becomes maximum from the cut-out waveform (step S123).

Then, the detection unit 123 detects the timing at the midpoint between timing $T_{H1}$ and timing $T_{H2}$ as timing $T_H$ of the heel-strike (step S124).

<Opposite Heel-Strike>

Figure 24:
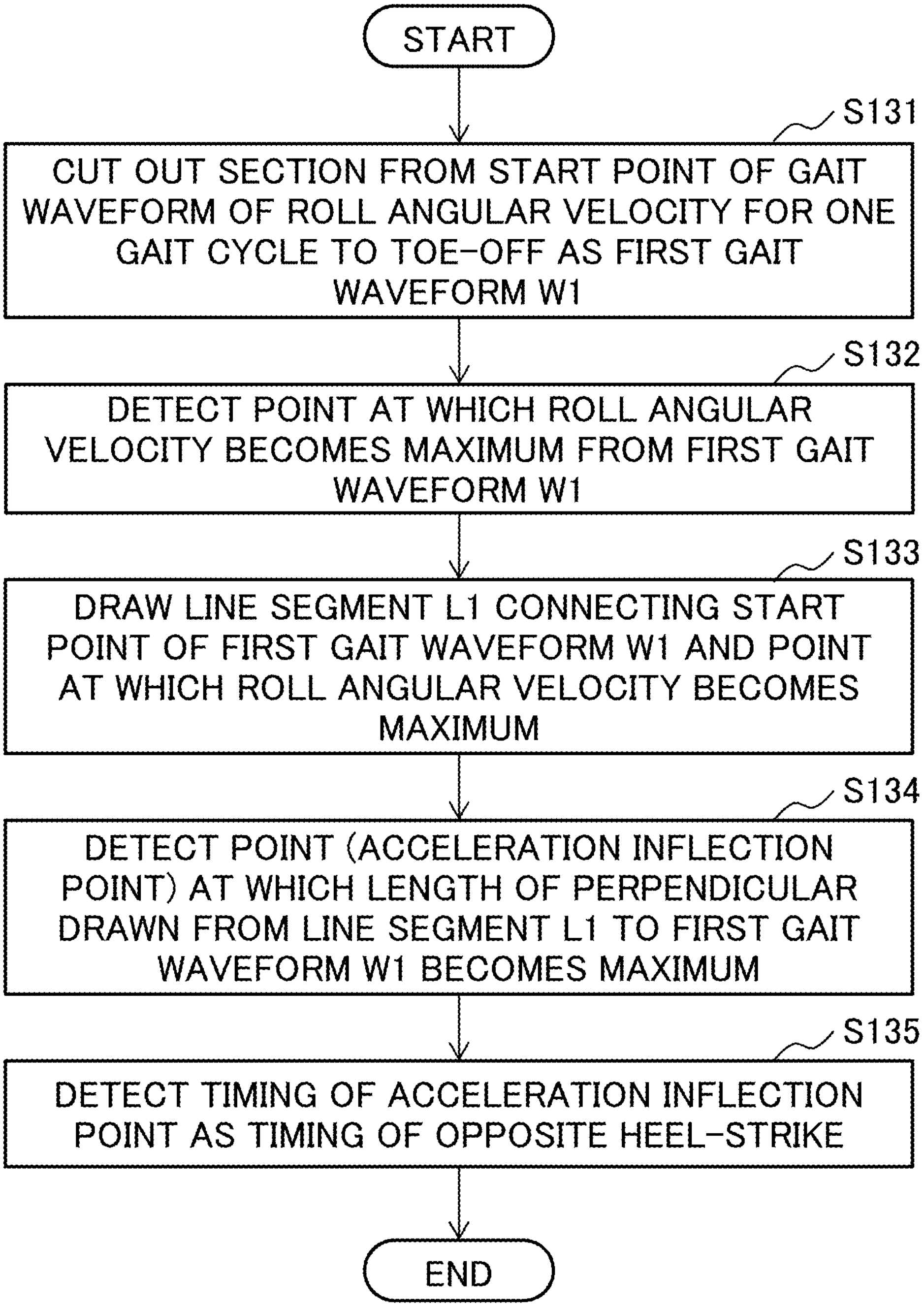
FIG. 24 is a flowchart for explaining an example of detection of an opposite heel-strike by the detection device according to the first example embodiment.

Next, an example of an algorithm for detecting the opposite heel-strike will be described with reference to the drawings. FIG. 24 is a flowchart for explaining an example of an algorithm for detecting the opposite heel-strike. The opposite foot-heel-strike corresponds to the start timing of the preswing stage of the stance phase.

In FIG. 24, first, the detection unit 123 cuts out a section from the start point of the gait waveform of the roll angular velocity for one gait cycle to the toe-off as a first gait waveform W1 (step S131).

Next, the detection unit 123 detects a point at which the roll angular velocity becomes maximum from the cut-out first gait waveform W1 (step S132).

Next, the detection unit 123 draws a line segment L1 connecting the start point of the first gait waveform W1 and the point at which the roll angular velocity becomes maximum (step S133).

Next, the detection unit 123 detects a point (acceleration inflection point) at which the length of the perpendicular line drawn from the line segment L1 to the first gait waveform W1 becomes maximum (step S134).

Then, the detection unit 123 detects the timing of the acceleration inflection point as the timing of the opposite heel-strike (step S135).

<Opposite Toe-Off>

Figure 25:
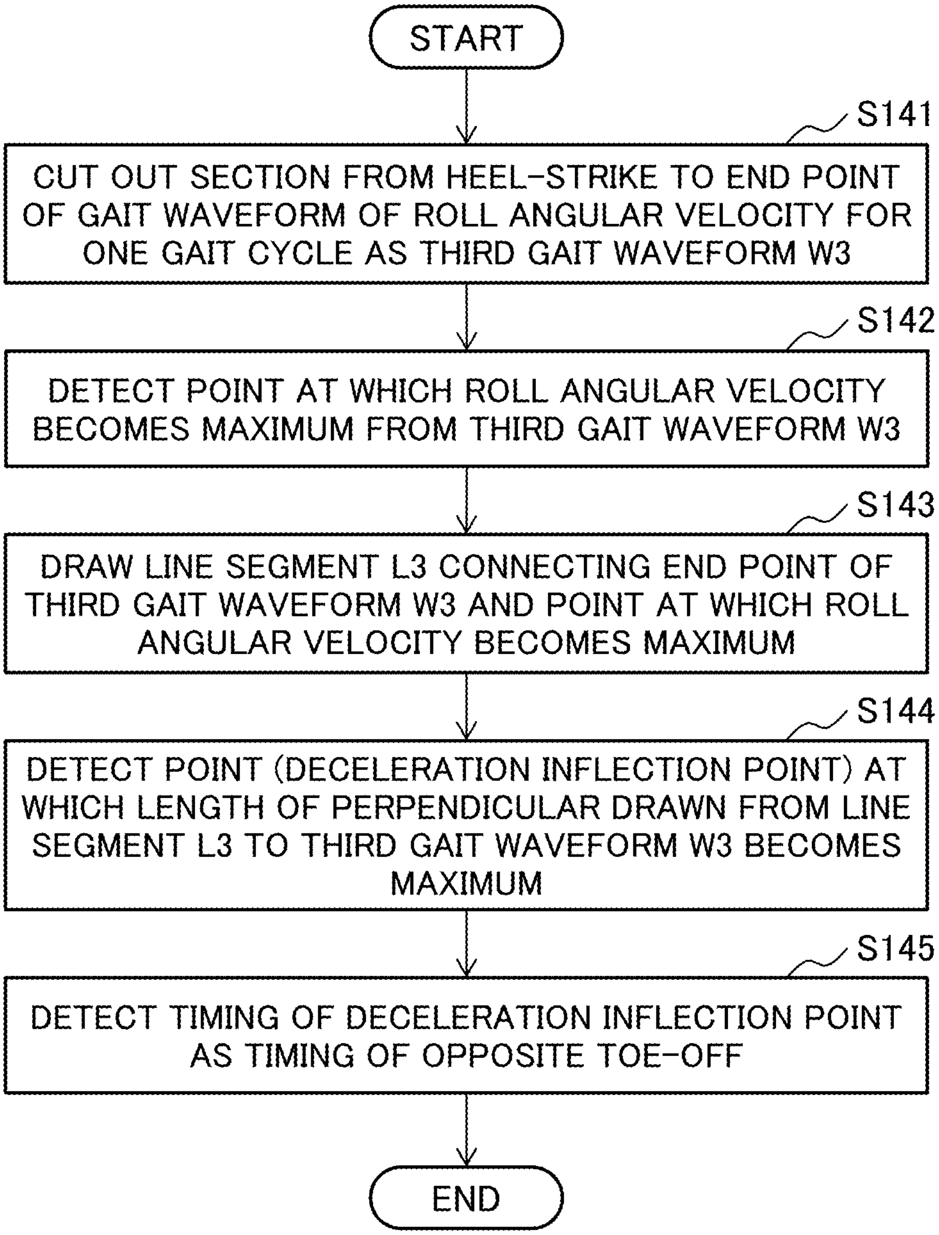
FIG. 25 is a flowchart for explaining an example of detection of an opposite toe-off by the detection device according to the first example embodiment.

Next, an example of an algorithm for detecting the opposite toe-off will be described with reference to the drawings. FIG. 25 is a flowchart for explaining an example of an algorithm for detecting the opposite toe-off. The opposite toe-off corresponds to the start timing of the mid-stance stage of the stance phase.

In FIG. 25, first, the detection unit 123 cuts out a section from the heel-strike to the end point of the gait waveform having the roll angular velocity for one gait cycle as a third gait waveform W3 (step S141).

Next, the detection unit 123 detects a point at which the roll angular velocity becomes maximum from the cut-out third gait waveform W3 (step S142).

Next, the detection unit 123 draws a line segment L3 connecting the end point of the third gait waveform W3 and the point at which the roll angular velocity becomes maximum (step S143).

Next, the detection unit 123 detects a point (deceleration inflection point) at which the length of the perpendicular line drawn from the line segment L3 to the third gait waveform W3 becomes maximum (step S144).

Then, the detection unit 123 detects the timing of the deceleration inflection point as the timing of the opposite toe-off (step S145).

<Tibia-Vertical>

Figure 26:
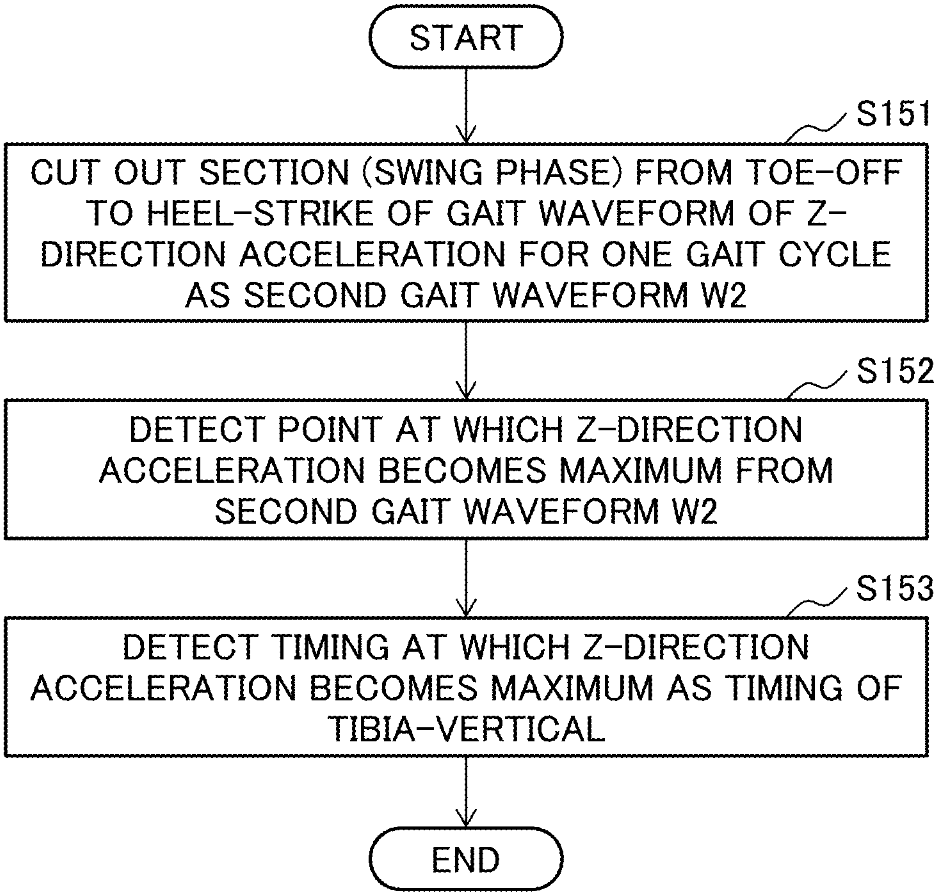
FIG. 26 is a flowchart for explaining an example of detection of a tibia-vertical by the detection device according to the first example embodiment.

Next, an example of an algorithm for detecting the tibia-vertical will be described with reference to the drawings. FIG. 26 is a flowchart for explaining an example of an algorithm for detecting the tibia-vertical. The tibia-vertical corresponds to the start timing of the end of the swing phase.

In FIG. 26, first, the detection unit 123 cuts out a section from the toe-off to the heel-strike of the gait waveform of the Z-direction acceleration for one gait cycle as a second gait waveform W2 (step S151).

Next, the detection unit 123 detects a point at which the Z-direction acceleration becomes maximum from the cut-out second gait waveform W2 (step S152).

Then, the detection unit 123 detects the timing at which the Z-direction acceleration becomes maximum as the timing of the tibia-vertical (step S153).

<Foot-Adjacent>

Figure 27:
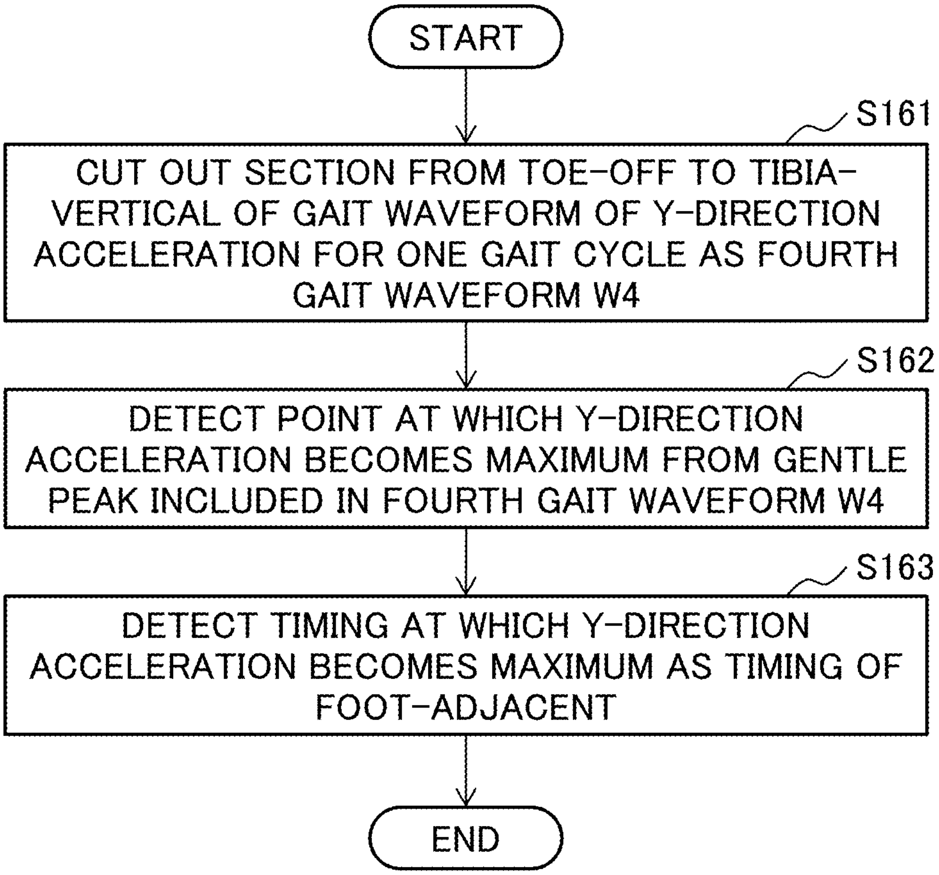
FIG. 27 is a flowchart for explaining an example of detection of a foot-adjacent by the detection device according to the first example embodiment.

Next, an example of an algorithm for detecting the foot-adjacent will be described with reference to the drawings. FIG. 27 is a flowchart for explaining an example of an algorithm for detecting the foot-adjacent. The foot-adjacent corresponds to the central timing of the mid-swing stage of the swing phase.

In FIG. 27, first, the detection unit 123 cuts out a section from the toe-off to the tibia-vertical of the gait waveform of the Y-direction acceleration for one gait cycle as a fourth gait waveform W4 (step S161).

Next, the detection unit 123 detects a point at which the Y-direction acceleration becomes maximum from a gentle peak (a peak on a side close to the tibia-vertical) included in the fourth gait waveform W4 (step S162).

Then, the detection unit 123 detects the timing at which the Y-direction acceleration becomes maximum as the timing of the foot-adjacent (step S163).

<Heel-Rise>

Figure 28:
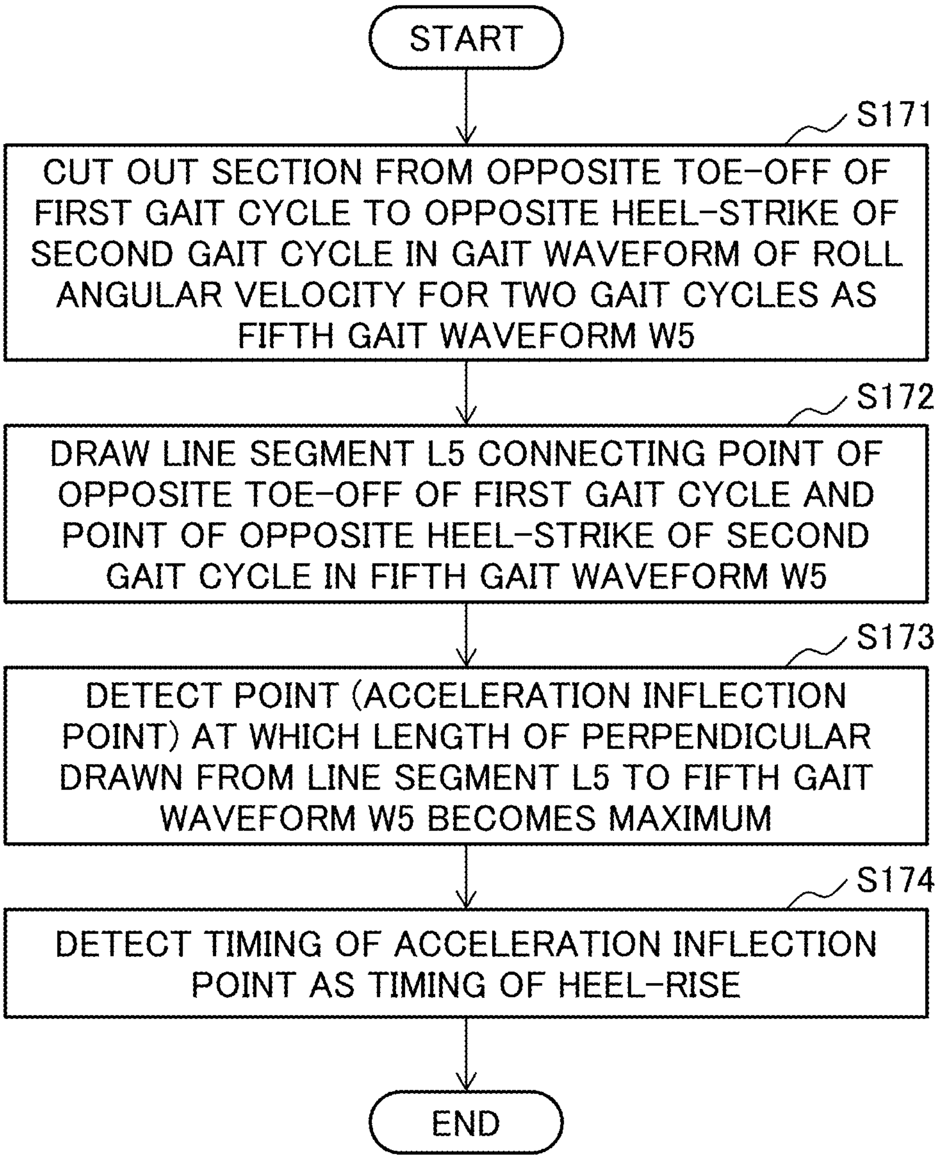
FIG. 28 is a flowchart for explaining an example of detection of a heel-rise by the detection device according to the first example embodiment.

Next, an example of an algorithm for detecting the heel-rise will be described with reference to the drawings. FIG. 28 is a flowchart for explaining an example of an algorithm for detecting the heel-rise. The timing of the heel-rise corresponds to the start timing of the terminal stance stage of the stance phase. That is, the timing of the heel-rise corresponds to the start point and the end point of one gait cycle.

In FIG. 28, first, in the gait waveform of the roll angular velocity for two gait cycles, the detection unit 123 cuts out a section from the opposite toe-off in the first gait cycle to the opposite heel-strike in the second gait cycle as a fifth gait waveform W5 (step S171).

Next, in the cut-out fifth gait waveform W5, the detection unit 123 draws a line segment L5 connecting the point of the opposite toe-off in the first gait cycle and the point of the opposite heel-strike in the second gait cycle (step S172).

Next, the detection unit 123 detects a point (acceleration inflection point) at which the length of the perpendicular line drawn from the line segment L5 to the fifth gait waveform W5 becomes maximum (step S173).

Then, the detection unit 123 detects the timing of the deceleration inflection point as the timing of the heel-rise (step S174).

As described above, the detection system of the present example embodiment includes the data acquisition device and the detection device. The data acquisition device measures the spatial acceleration and the spatial angular velocity, generates sensor data based on the measured spatial acceleration and spatial angular velocity, and transmits the generated sensor data to the detection device. The detection device includes an extraction unit and a detection unit. The extraction unit generates time-series data associated with walking using sensor data based on a physical quantity related to movement of a foot measured by a sensor installed in one foot portion of a pedestrian, and extracts a gait waveform from the generated time-series data. The detection unit detects a gait event of both feet of the pedestrian from the gait waveform extracted by the extraction unit.

In the present example embodiment, a gait waveform is extracted from time-series data generated using sensor data based on a physical quantity related to movement of a foot measured by a sensor installed in one foot portion of a pedestrian. Then, in the present example embodiment, a gait event of both feet is detected from the extracted gait waveform. Therefore, according to the present example embodiment, a detailed gait event of both feet can be detected on the basis of the physical quantity related to the movement of the foot measured by the sensor attached to one foot.

In one aspect of the present example embodiment, the extraction unit generates time-series data of the acceleration in the traveling direction of the pedestrian. The extraction unit extracts a gait waveform of the acceleration in the traveling direction for one gait cycle from the generated time-series data of the acceleration in the traveling direction. The detection unit detects a timing at which a trough is detected between two peaks included in the maximum peak in the extracted gait waveform of the acceleration in the traveling direction for one gait cycle as the timing of the toe-off. The detection unit detects the timing of the midpoint between the timing at which the minimum peak is detected and the timing at which the maximum peak appearing after the minimum peak is detected as the timing of the heel-strike.

For example, the extraction unit generates time-series data of the roll angular velocity of the pedestrian. The extraction unit extracts, from the generated time-series data of the roll angular velocity, a gait waveform of the roll angular velocity for one gait cycle starting from the start timing of the terminal stance stage. The detection unit divides the extracted gait waveform of the roll angular velocity for one gait cycle into a first gait waveform, a second gait waveform, and a third gait waveform at the timing of the toe-off and the timing of the heel-strike. The detection unit detects the timing of the opposite heel-strike from the first gait waveform of the roll angular velocity, and detects the timing of the opposite toe-off from the third gait waveform of the roll angular velocity.

For example, the detection unit detects a point at which the roll angular velocity becomes maximum from the first gait waveform of the roll angular velocity. The detection unit draws a perpendicular line to the first gait waveform of the roll angular velocity from a line segment connecting a start point of the first gait waveform of the roll angular velocity and a point at which the roll angular velocity becomes maximum in the first gait waveform of the roll angular velocity. The detection unit detects the timing of the acceleration inflection point at which the length of the perpendicular line becomes maximum as the timing of the opposite heel-strike.

For example, the detection unit detects a point at which the roll angular velocity becomes maximum from the third gait waveform of the roll angular velocity. The detection unit draws a perpendicular line to the third gait waveform of the roll angular velocity from a line segment connecting a start point of the third gait waveform of the roll angular velocity and a point at which the roll angular velocity becomes maximum in the third gait waveform of the roll angular velocity. The detection unit detects the timing of the deceleration inflection point at which the length of the perpendicular line becomes maximum as the timing of the opposite toe-off.

For example, the extraction unit generates time-series data of the acceleration in the gravity direction of the pedestrian. The extraction unit extracts, from the generated time-series data of the acceleration in the gravity direction, a gait waveform of the acceleration in the gravity direction for one gait cycle starting from the start timing of the terminal stance stage. The detection unit divides the extracted gait waveform of the acceleration in the gravity direction for one gait cycle into a first gait waveform, a second gait waveform, and a third gait waveform at the timing of the toe-off and the timing of the heel-strike. The detection unit detects a timing at which the second gait waveform of the acceleration in the gravity direction becomes maximum as a timing of the tibia-vertical.

For example, the detection unit cuts out a fourth gait waveform between the timing of the toe-off and the timing of the tibia-vertical from the gait waveform of the acceleration in the traveling direction for one gait cycle. The detection unit detects, as the timing of the foot-adjacent, the timing at which the peak on the side close to the timing of the tibia-vertical included in the fourth gait waveform of the acceleration in the traveling direction becomes maximum.

For example, the extraction unit extracts, from the time-series data of the roll angular velocity, a gait waveform of the roll angular velocity for two gait cycles starting from the start timing of the terminal stance stage. In the extracted gait waveform of the roll angular velocity for the two gait cycles, the detection unit draws a perpendicular line to the gait waveform of the roll angular velocity from a line segment connecting a point of the opposite toe-off of the first gait cycle and a point of the opposite toe-off of the second gait cycle subsequent to the first gait cycle. The detection unit detects the timing of the acceleration inflection point at which the length of the perpendicular line becomes maximum as the timing of the heel-rise.

In this aspect, a plurality of gait events is sequentially detected from the gait waveform of the pedestrian. Therefore, according to the present example embodiment, the gait event of both feet can be detected in more detail based on the physical quantity related to the movement of the foot measured by the sensor attached to one foot.

Second Example Embodiment

Next, a detection system according to a second example embodiment will be described with reference to the drawings. The detection system of the present example embodiment specifies the time at which each of the plurality of gait events detected from the gait waveform occurs, and calculates the time factor related to the gait based on the specified time. The detection system of the present example embodiment estimates the physical condition of the pedestrian using the calculated time factor related to the gait.

Figure 29:
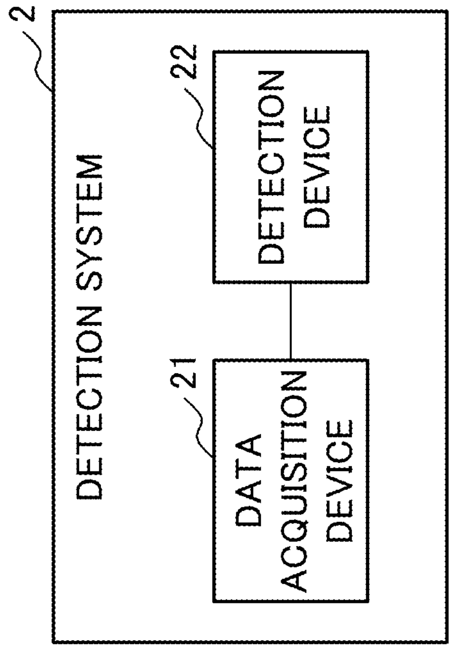
FIG. 29 is a block diagram for explaining an example of a configuration of a detection system according to a second example embodiment.

FIG. 29 is a block diagram illustrating an example of a configuration of a detection system 2 of the present example embodiment. As illustrated in FIG. 29, the detection system 2 includes a data acquisition device 21 and a detection device 22. The data acquisition device 21 and the detection device 22 may be connected by wire or wirelessly. In addition, the data acquisition device 21 and the detection device 22 may be configured by a single device. In addition, the detection system 2 may be configured only by the detection device 22 by excluding the data acquisition device 21 from the configuration of the detection system 2. The data acquisition device 21 has the same configuration as the data acquisition device 11 of the first example embodiment. Hereinafter, the detection device 22 different from that of the first example embodiment will be described focusing on differences from the first example embodiment.

[Detection Device]

Figure 30:
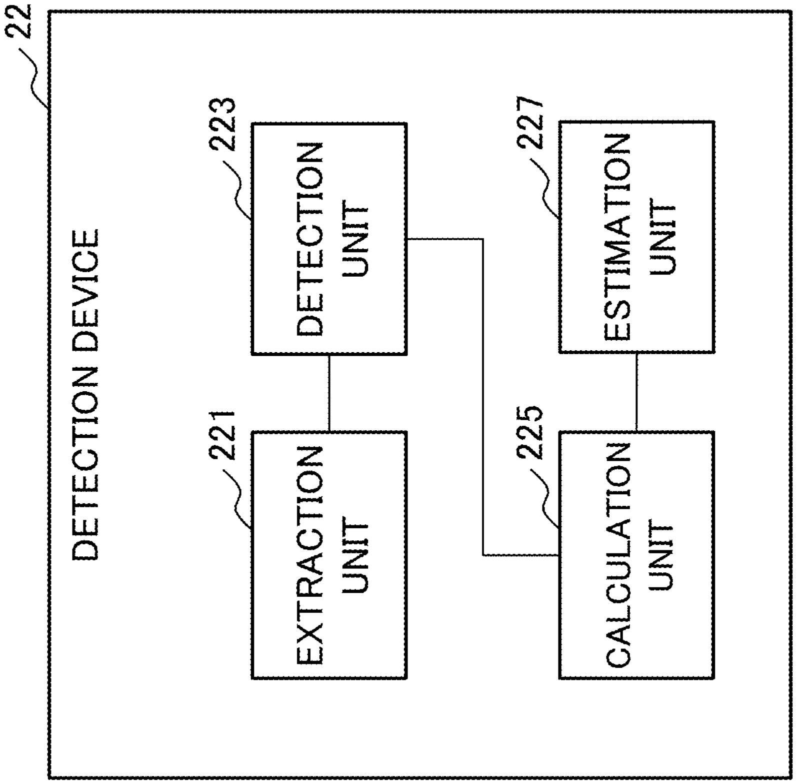
FIG. 30 is a block diagram for explaining an example of a configuration of a detection device of the detection system according to the second example embodiment.

FIG. 30 is a block diagram illustrating an example of a configuration of the detection device 22. The detection device 22 includes an extraction unit 221, a detection unit 223, a calculation unit 225, and an estimation unit 227.

The extraction unit 221 acquires sensor data from the data acquisition device 21 (sensor) installed on the footwear. The extraction unit 221 uses the sensor data to generate time-series data associated with walking of the pedestrian wearing the footwear on which the data acquisition device 21 is installed. The extraction unit 221 extracts gait waveform data for one gait cycle or two gait cycles from the generated time-series data. The extraction unit 221 has the same configuration as the extraction unit 121 of the first example embodiment.

The detection unit 223 detects a gait event of a pedestrian walking in footwear on which the data acquisition device 21 is installed from the gait waveform data generated by the extraction unit 221. For example, the detection unit 223 extracts a feature for each gait event from the gait waveform data related to the movement of the foot. For example, the detection unit 223 detects the timing of the extracted feature for each gait event as the timing of each gait event. The detection unit 223 has the same configuration as the detection unit 123 of the first example embodiment.

The calculation unit 225 specifies the time of the gait event detected by the detection unit 223. The calculation unit 225 calculates a time factor related to the gait on the basis of the specified time of the gait event. For example, the calculation unit 225 calculates a time factor related to a period (double-leg support period) in which both feet are in contact with the ground and a period (single-leg support period) in which one leg is in contact with the ground on the basis of the specified time of the gait event. For example, the calculation unit 225 calculates a time factor related to a period in which the right foot is in contact with the ground (right-foot stance period) and a period in which the left foot is in contact with the ground (left-foot stance period) on the basis of the specified time of the gait event. For example, the calculation unit 225 calculates a time factor related to the step time of the right foot and the step time of the left foot on the basis of the specified time of the gait event.

The estimation unit 227 estimates the physical condition of the pedestrian based on the time factor calculated by the calculation unit 225. For example, the estimation unit 227 estimates the muscle weakness situation of the pedestrian based on the time factor related to the ratio between the double-leg support period and the single-leg support period. For example, the estimation unit 227 estimates the bone density of the pedestrian on the basis of a time factor related to asymmetry between the right-foot stance period and the left-foot stance period. For example, the estimation unit 227 estimates the basal metabolism of the pedestrian based on a time factor related to asymmetry of the stride time of the right foot and the stride time of the left foot. The estimation unit 227 outputs the estimated physical condition of the pedestrian to a system or a device (not illustrated).

Figure 31:
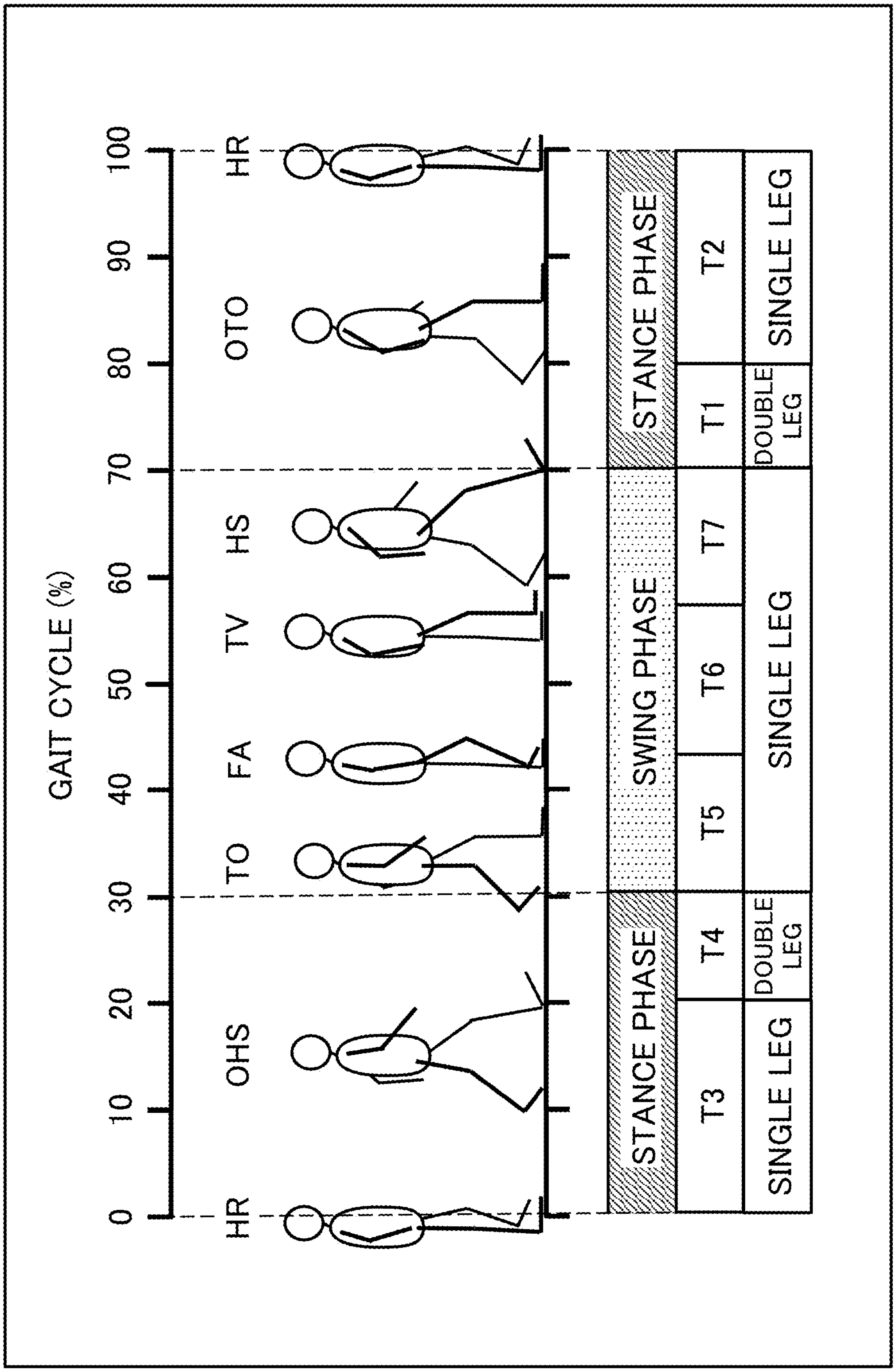
FIG. 31 is a conceptual diagram for explaining a single-leg support period and a double-leg support period in a gait cycle corresponding to one gait cycle cut out by the detection device of the detection system according to the second example embodiment.

FIG. 31 is a conceptual diagram for describing a double-leg support period and a single-leg support period in one gait cycle starting from the start timing of the terminal stance stage of the stance phase. The mid-stance stage T2 and the terminal stance stage T3 of the stance phase, the initial swing stage T5, the mid-swing stage T6, and the terminal swing stage T7 of the swing phase are in the single-leg support period. The initial stance stage T1 and the preswing stage T4 of the stance phase are in the double-leg support period. In the present example embodiment, since the stance phase and the swing phase can be subdivided based on the occurrence time of the gait event, the single-leg support period and the double-leg support period can be specified.

For example, the ratio between the double-leg support period and the single-leg support period is related to muscle strength. When muscle strength of a human decreases with aging, the double-leg support period in walking tends to increase. For example, the detection device 22 calculates a time factor related to the ratio between the double-leg support period and the single-leg support period, and estimates the muscle weakness situation of the pedestrian based on the calculated time factor. For example, the detection device 22 calculates the ratio of the double-leg support period to the single-leg support period as a time factor, and estimates that the muscle strength of the pedestrian tends to decrease when the value of the calculated time factor is large.

Figure 32:
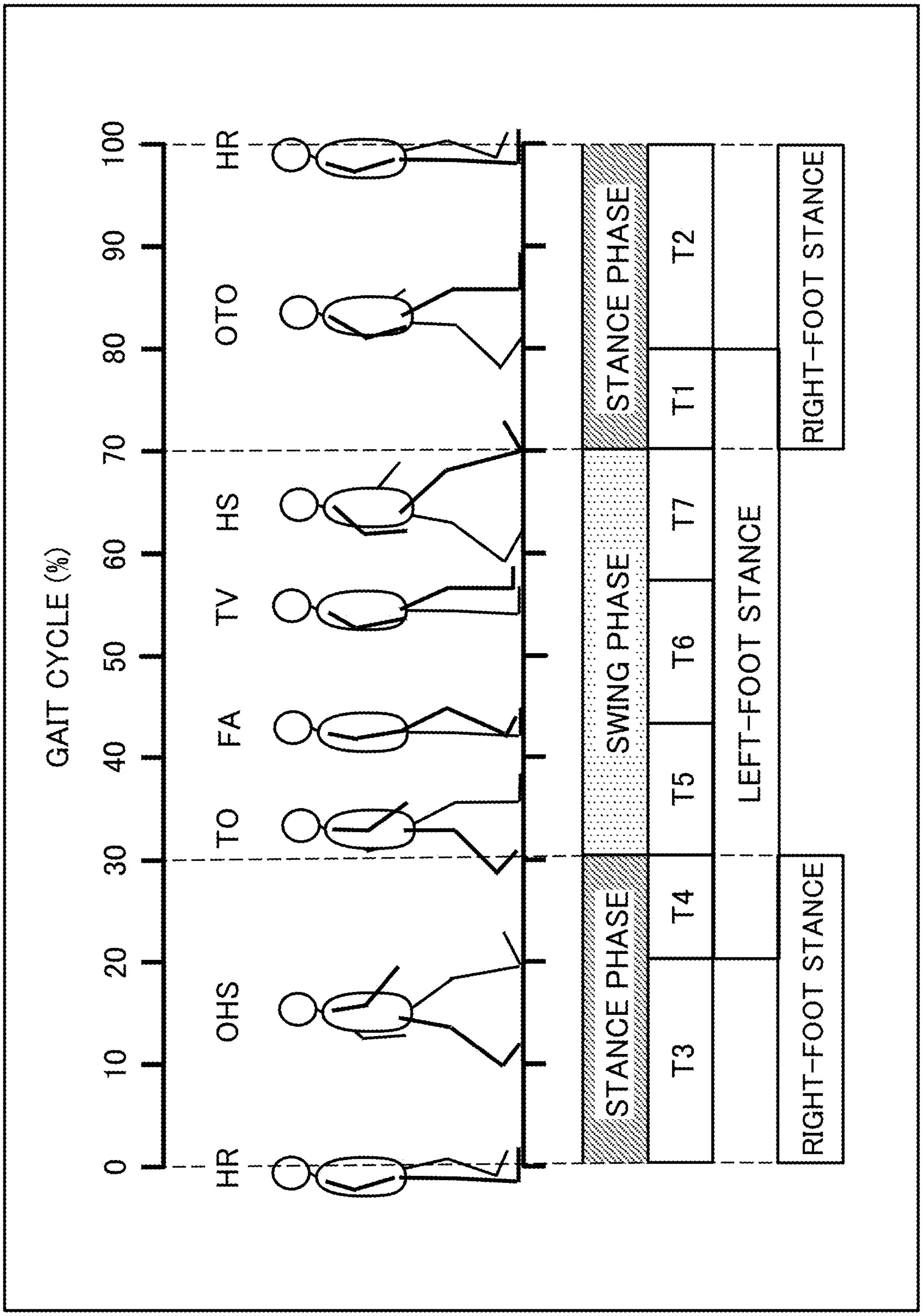
FIG. 32 is a conceptual diagram for explaining asymmetry of walking in a gait cycle corresponding to one gait cycle cut out by the detection device of the detection system according to the second example embodiment.

FIG. 32 is a conceptual diagram for explaining a right-foot grounding period and a left-foot grounding period in one gait cycle starting from the start timing of the terminal stance stage of the stance phase. The initial stance stage T1, the mid-stance stage T2, the terminal stance stage T3, and the preswing stage T4 of the stance phase are in the right-foot stance period. An initial swing stage T5, a mid-swing stage T6, and a terminal swing stage T7 of the swing phase are in the left-foot stance period. In the present example embodiment, since the stance phase and the swing phase can be subdivided based on the occurrence time of the gait event, the right-foot stance period and the left-foot stance period can be specified.

The asymmetry between the right-foot stance period and the left-foot stance period is related to bone density. When the bone density of a human decreases, asymmetry between the right-foot stance period and the left-foot stance period tends to increase. For example, the detection device 22 calculates a time factor related to a ratio between the right-foot stance period and the left-foot stance period, and estimates the bone density of the pedestrian on the basis of the value of the calculated time factor. For example, the detection device 22 calculates a ratio of a difference between the right-foot stance period and the left-foot stance period with respect to the both-feet stance period as a time factor, and estimates that the bone density of the pedestrian is decreased when the value of the calculated time factor is large.

The asymmetry of the stride time of the right foot and the stride time of the left foot is related to basal metabolism. When basal metabolism of a human decreases due to the influence of aging, metabolic syndrome, and the like, asymmetry between the stride time of the right foot and the stride time of the left foot tends to increase. For example, the detection device 22 calculates a time factor related to a ratio of the stride time of the right foot and the stride time of the left foot, and estimates the basal metabolism of the pedestrian based on the value of the calculated time factor. For example, the detection device 22 calculates a ratio of the stride time of the left foot to the stride time of the right foot as a time factor, and estimates that the basal metabolism of the pedestrian is decreased when the value of the calculated time factor is small.

The estimation unit 227 may estimate the physical condition of the pedestrian using a learned model that has learned the feature amount extracted from the gait waveform. For example, the estimation unit 227 inputs the feature amount extracted from the gait waveform to be estimated to the learned model that has learned the feature amount extracted from the gait waveform to be learned, and estimates the physical condition of the pedestrian. For example, the learned model is a model obtained by learning a predictor vector obtained by combining feature amounts (also referred to as predictors) extracted from a gait waveform to be learned. For example, the learned model is a model obtained by learning a predictor vector obtained by combining feature amounts (predictors) extracted from at least one of the gait waveforms of the acceleration in the three-axis directions, the angular velocity in the three-axis directions, the trajectory in the three-axis directions, and the plantar angle in the three-axis directions.

Figure 33:
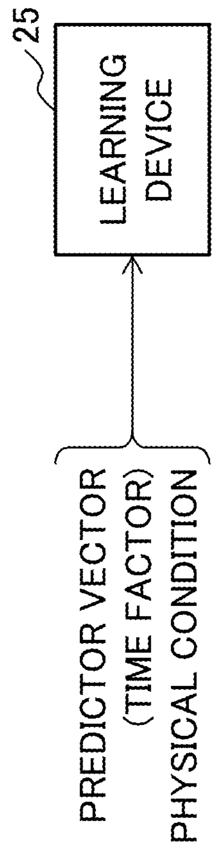
FIG. 33 is a conceptual diagram illustrating an example in which a learned model used by the detection device of the detection system according to the second example embodiment is generated by machine learning.
Figure 34:
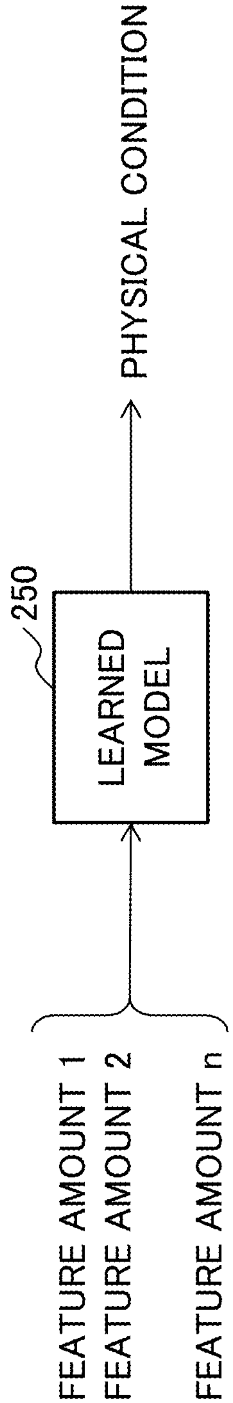
FIG. 34 is a conceptual diagram illustrating an example in which the detection device of the detection system according to the second example embodiment inputs the feature amount to the learned model, thereby outputting the body information of the user.

FIG. 33 is a conceptual diagram illustrating an example in which the learning device 25 learns the predictor vector (time factor) and the physical condition. For example, the physical condition is an index related to muscle weakness, bone density, and basal metabolism of a pedestrian. FIG. 34 is a conceptual diagram illustrating an example in which the feature amounts 1 to n extracted from the gait waveforms are input to a learned model 250 learned by the learning device 25, and the physical condition is output (n is a natural number).

The learning device 25 performs learning using, as training data, a predictor vector obtained by combining feature amounts (predictors) extracted from a gait waveform based on physical quantities related to movement of a foot and a physical condition. The learning device 25 generates the learned model 250 that outputs the physical condition when the feature amount extracted from the actually measured gait waveform is input by learning. For example, the learning device 25 generates the learned model 250 by supervised learning in which a feature amount such as the occurrence time of a toe-off or heel-strike, an opposite heel-strike, an opposite toe-off, a tibia-vertical, a foot-adjacent, and a heel-rise is used as an explanatory variable and a physical condition is used as a response variable. For example, the learning device 25 outputs, as the estimation result of the physical condition, an output from the learned model 250 when the occurrence time of the gait event such as the toe-off, the heel-strike, the opposite heel-strike, the opposite toe-off, the tibia-vertical, the foot-adjacent, and the heel-rise is input to the learned model 250.

(Operation)

Figure 35:
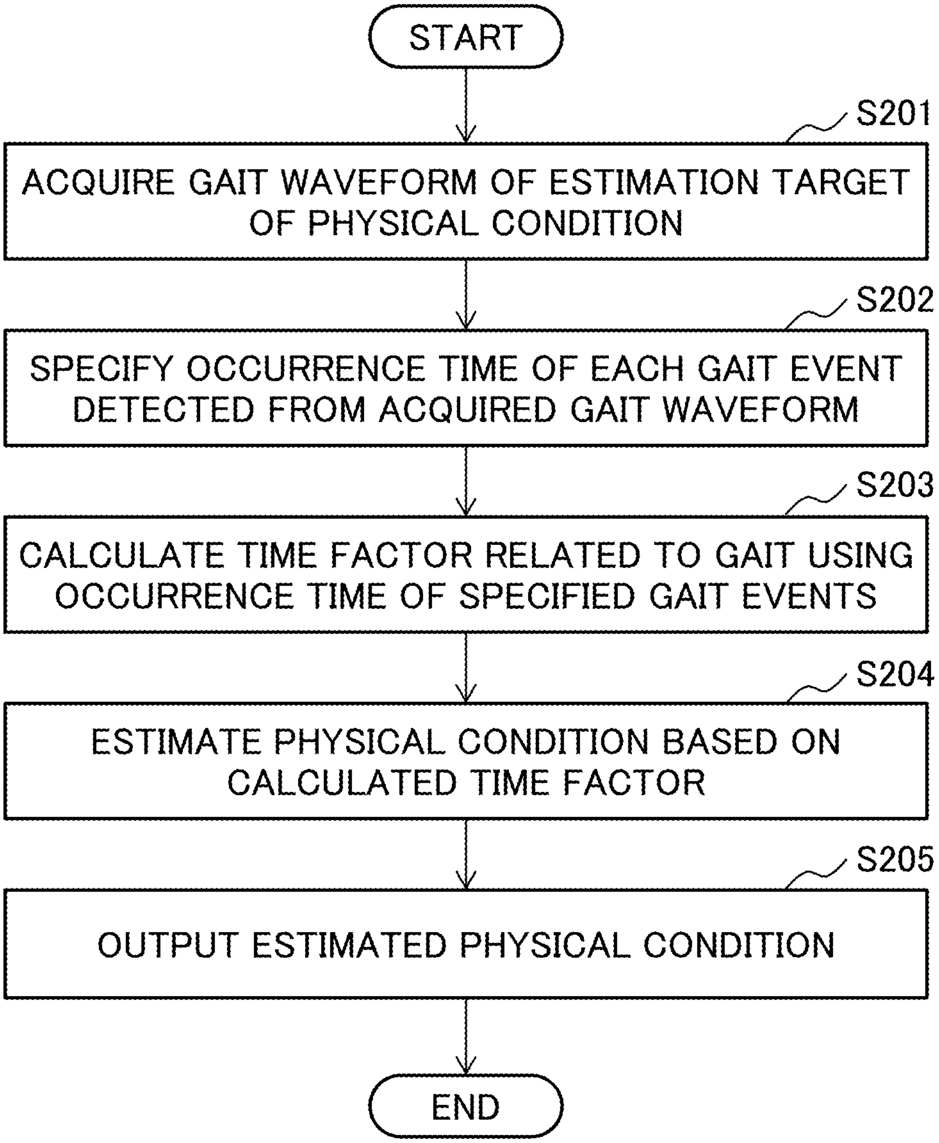
FIG. 35 is a flowchart for explaining an example of estimation of a physical condition by the detection device of the detection system according to the second example embodiment.

Next, an operation of the detection system 2 of the present example embodiment will be described with reference to the drawings. Hereinafter, processing in which the detection device 22 of the detection system 2 estimates the physical condition of the pedestrian based on the time factor of the gait event detected from the gait waveform will be described. Hereinafter, the detection device 22 will be described as the subject of operation. FIG. 35 is a flowchart for explaining processing in which the detection device 22 estimates the physical condition of the pedestrian.

In FIG. 35, first, the detection device 22 acquires a gait waveform of an estimation target of the physical condition (step S201).

Next, the detection device 22 specifies the occurrence time of each gait event detected from the acquired gait waveform (step S202).

Next, the detection device 22 calculates a time factor related to the gait using the specified occurrence time of each gait event (step S203).

Next, the detection device 22 estimates a physical condition on the basis of the calculated time factor (step S204).

Then, the detection device 22 outputs the estimated physical condition (step S205).

<Muscle Weakness Situation>

Figure 36:
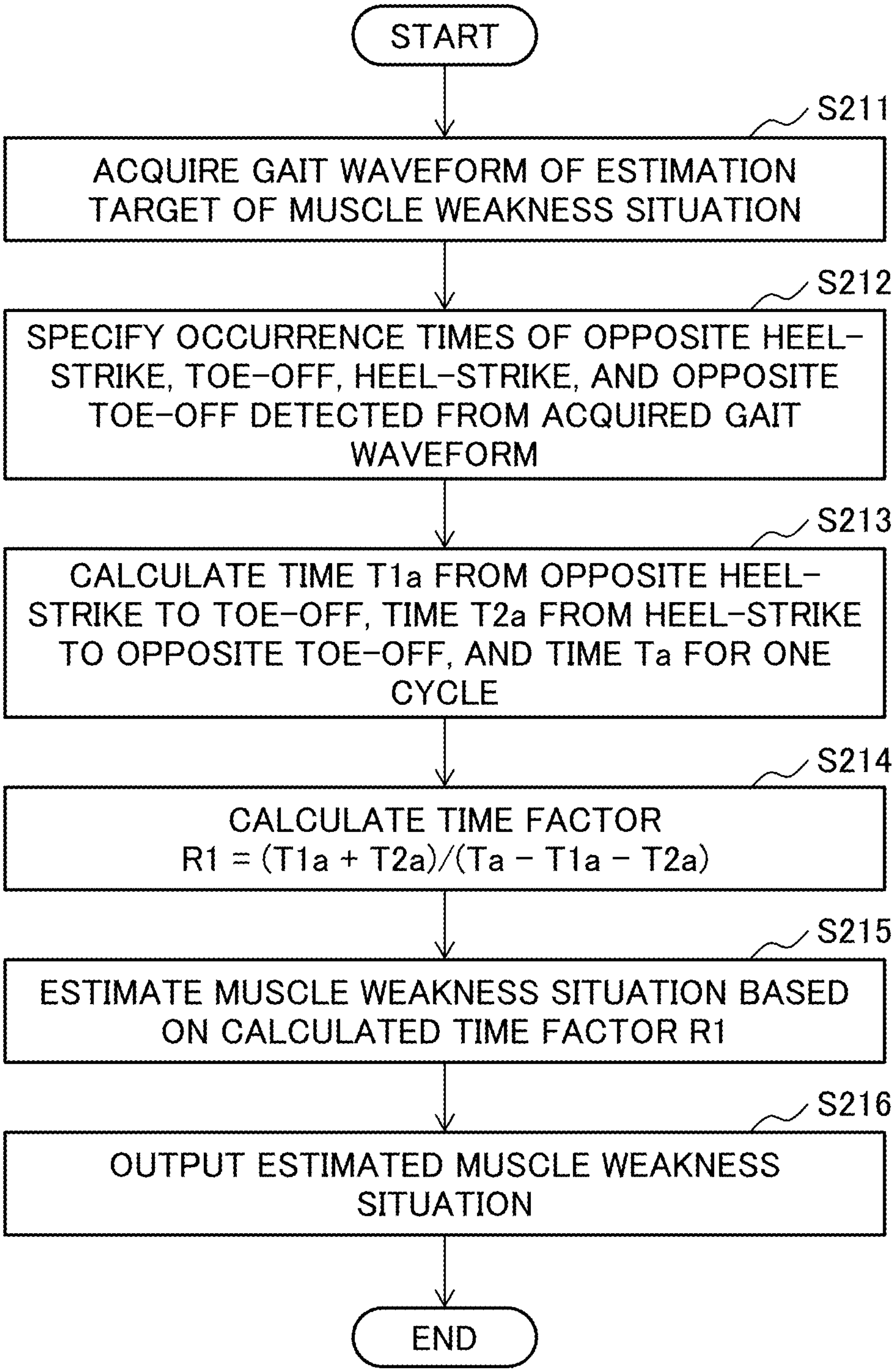
FIG. 36 is a flowchart for explaining an example of estimation of a muscle weakness situation by the detection device of the detection system according to the second example embodiment.

Next, an example in which the detection device 22 estimates a muscle weakness situation will be described as an example of processing of estimating the physical condition of the pedestrian from the gait waveform. FIG. 36 is a flowchart for explaining processing in which the detection device 22 estimates a muscle weakness situation of a pedestrian. Hereinafter, the detection device 22 will be described as the subject of operation.

In FIG. 36, first, the detection device 22 acquires a gait waveform of an estimation target of the muscle weakness situation (step S211).

Next, the detection device 22 specifies occurrence times of the opposite heel-strike, the toe-off, the heel-strike, and the opposite toe-off detected from the acquired gait waveform (step S212).

Next, the detection device 22 calculates a time T1$a$ from the opposite heel-strike to the toe-off, a time T2$a$ from the heel-strike to the opposite toe-off, and a time Ta of one gait cycle (step S213).

Next, the detection device 22 calculates a time factor R1 (also referred to as a first time factor) related to the muscle weakness situation using Formula 1 (step S214).

$$R1=(T1a+T2a)/(Ta-T1a-T2a) \quad (1)$$

Formula 1 is a ratio of the double-leg support period to the single-leg support period in one gait cycle.

Next, the detection device 22 estimates the muscle weakness situation based on the calculated time factor R1 (step S215). For example, the detection device 22 estimates the muscle weakness situation related to the calculated time factor R1 using a table in which the value of the time factor R1 is associated with the index value of the muscle weakness situation.

Then, the detection device 22 outputs the estimated muscle weakness situation (step S216).

<Bone Density>

Figure 37:
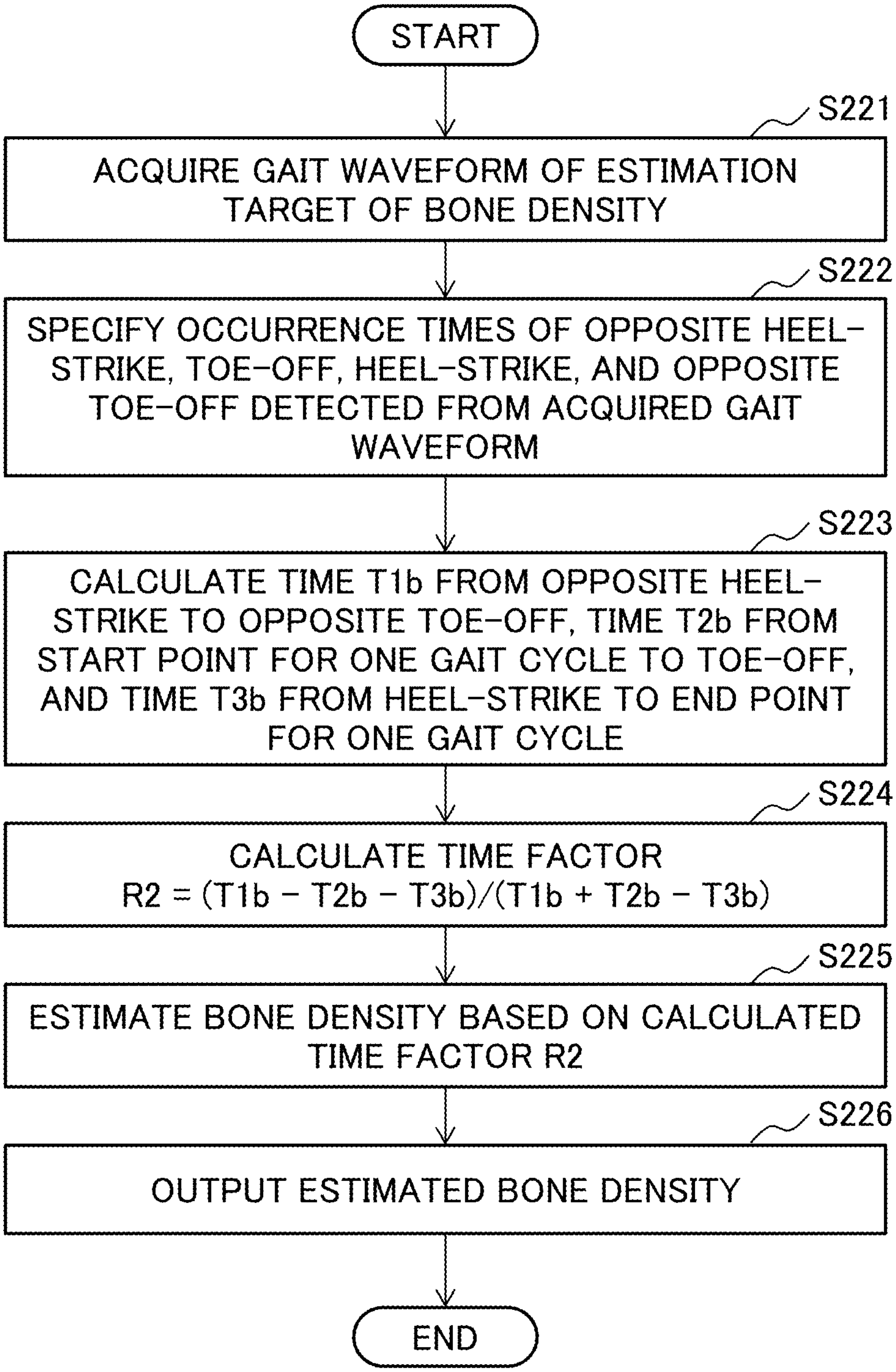
FIG. 37 is a flowchart for explaining an example of estimation of bone density by the detection device of the detection system according to the second example embodiment.

Next, an example in which the detection device 22 estimates the bone density will be described as an example of processing of estimating the physical condition of the pedestrian from the gait waveform. FIG. 37 is a flowchart for explaining processing in which the detection device 22 estimates the bone density of the pedestrian. Hereinafter, the detection device 22 will be described as the subject of operation.

In FIG. 37, first, the detection device 22 acquires a gait waveform of an estimation target of bone density (step S221).

Next, the detection device 22 specifies occurrence times of the opposite heel-strike, the toe-off, the heel-strike, and the opposite toe-off detected from the acquired gait waveform (step S222).

Next, the detection device 22 calculates a time T1$b$ from the opposite heel-strike to the opposite toe-off, a time T2$b$ from the start point of one gait cycle to the toe-off, and a time T3$b$ from the heel-strike to the end point of one gait cycle (step S223).

Next, the detection device 22 calculates a time factor R2 (also referred to as a second time factor) related to the bone density using Formula 2 (step S224).

$$R2=(T1b-T2b-T3b)/(T1b+T2b-T3b) \quad (2)$$

Formula 2 is the ratio of a difference between the right-foot stance period and the left-foot stance period with respect to the both-feet stance period.

Next, the detection device 22 estimates the bone density based on the calculated time factor R2 (step S225). For example, the detection device 22 estimates the bone density related to the calculated time factor R2 using a table in which the value of the time factor R2 is associated with the value of the bone density.

Then, the detection device 22 outputs the estimated bone density (step S226).

<Basal Metabolism>

Figure 38:
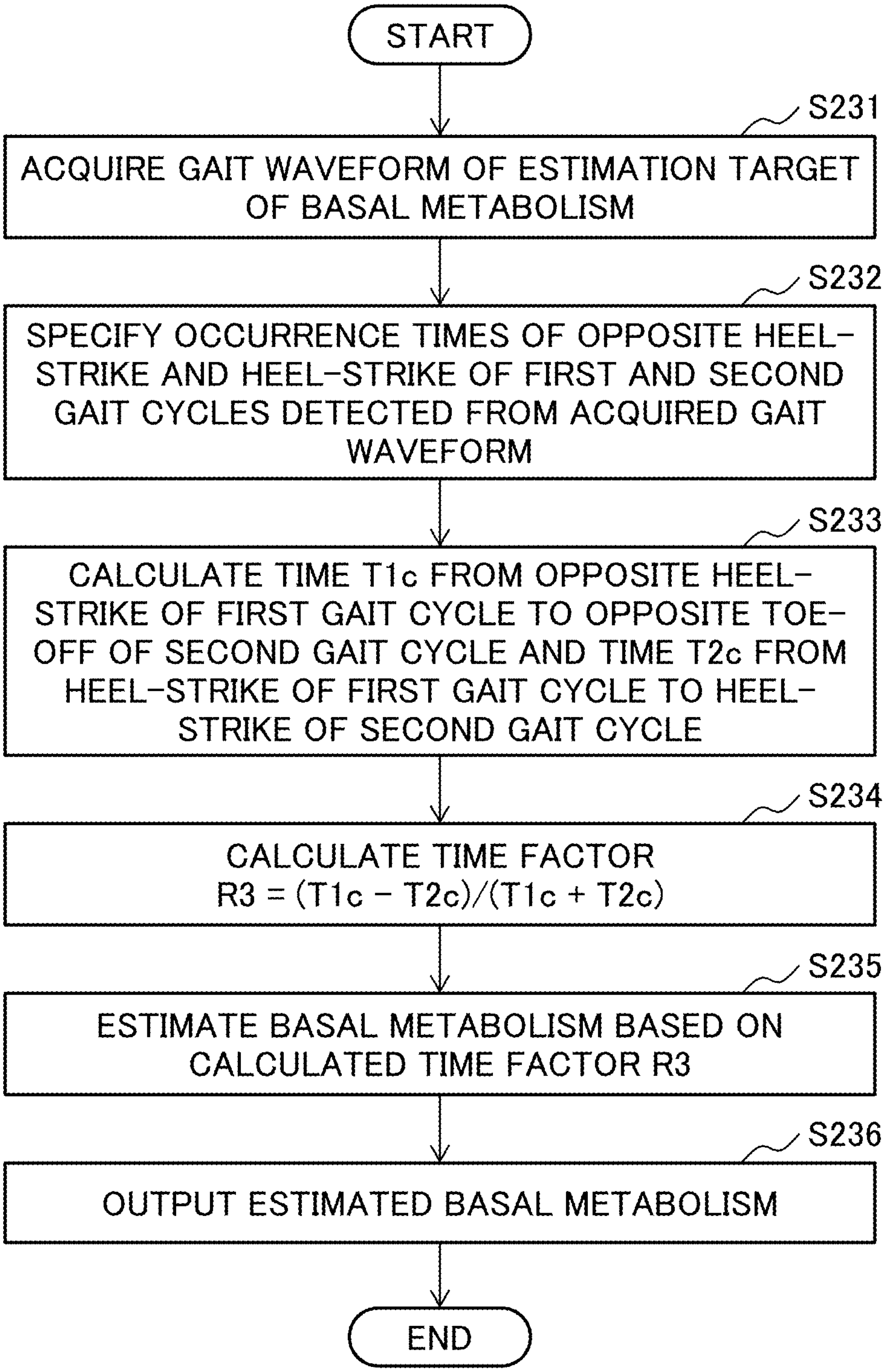
FIG. 38 is a flowchart for explaining an example of estimation of basal metabolism by the detection device of the detection system according to the second example embodiment.

Next, an example in which the detection device 22 estimates basal metabolism will be described as an example of processing of estimating the physical condition of the pedestrian from the gait waveform. FIG. 38 is a flowchart for explaining processing in which the detection device 22 estimates the basal metabolism of the pedestrian. Hereinafter, the detection device 22 will be described as the subject of operation.

In FIG. 38, first, the detection device 22 acquires a gait waveform of an estimation target of basal metabolism (step S231).

Next, the detection device 22 specifies occurrence times of the opposite heel-strike and the heel-strike of the first gait cycle and the second gait cycle detected from the acquired gait waveform (step S232).

Next, the detection device 22 calculates a time T1$c$ from the opposite heel-strike in the first gait cycle to the opposite toe-off in the second gait cycle, and a time T2$c$ from the heel-strike in the first gait cycle to the heel-strike in the second gait cycle (step S233).

Next, the detection device 22 calculates a time factor R3 (also referred to as a third time factor) related to basal metabolism using Formula 3 (step S234).

$$R3=(T1c-T2c)/(T1c+T2c) \quad (3)$$

Formula 3 is the ratio of the stride time of the left foot to the stride time of the right foot.

Next, the detection device 22 estimates basal metabolism on the basis of the calculated time factor R3 (step S235). For example, the detection device 22 estimates the basal metabolism related to the calculated time factor R3 using a table in which the value of the time factor R3 is associated with the value of the basal metabolism.

Then, the detection device 22 outputs the estimated basal metabolism (step S236).

Application Example

Next, an application example of the detection system 2 of the present example embodiment will be described with reference to the drawings. In the present application example, an index related to the physical condition output by the detection device 22 is displayed or transmitted to a health management system or the like. In the following example, it is assumed that a data acquisition device is installed in a shoe of a pedestrian, and sensor data based on a physical quantity related to movement of a foot measured by the data acquisition device is transmitted to a mobile terminal possessed by the pedestrian. The sensor data transmitted to the mobile terminal is processed by a program installed in the mobile terminal.

Figure 39:
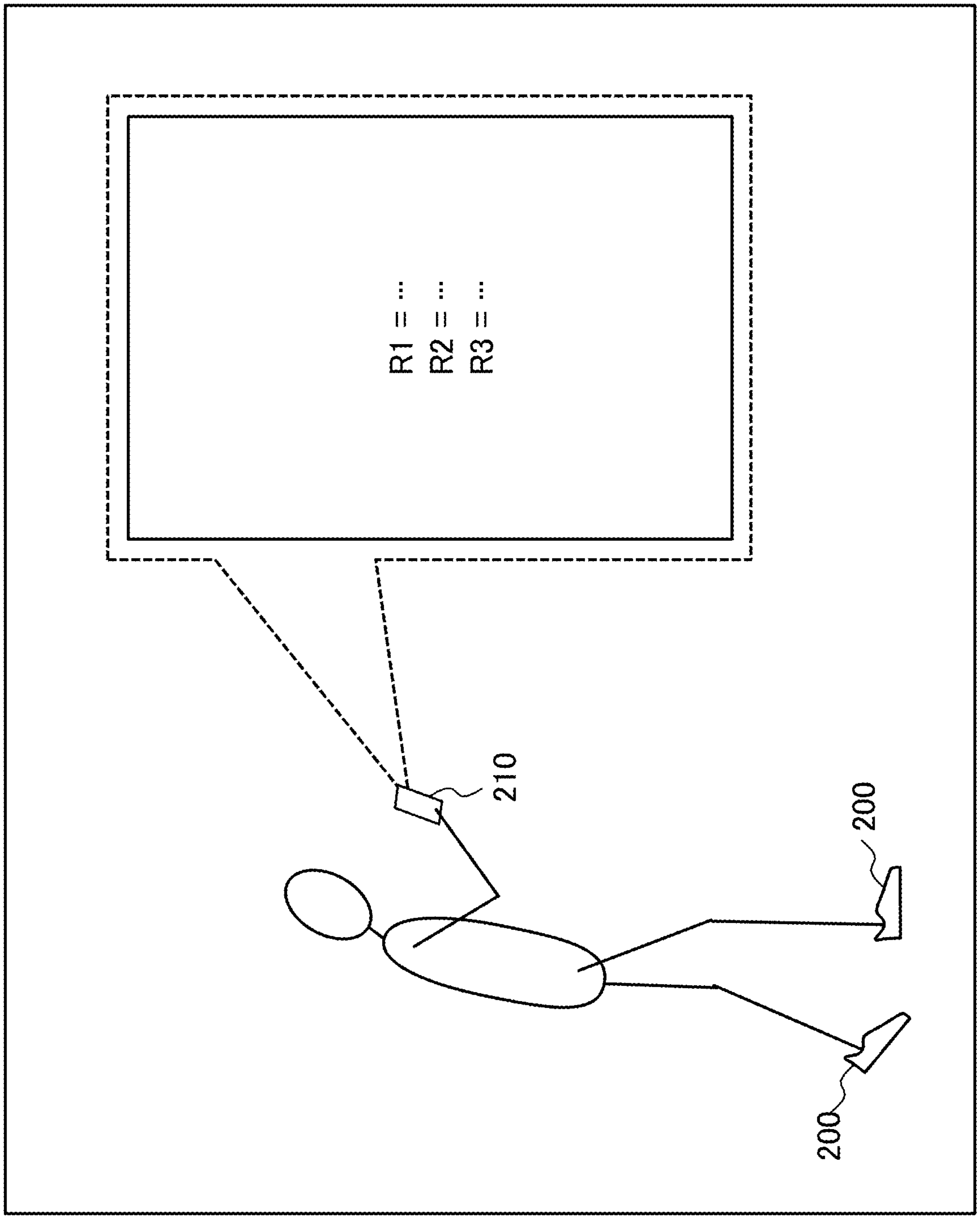
FIG. 39 is a conceptual diagram illustrating an example in which information related to a physical condition estimated by the detection device of the detection system according to the second example embodiment is displayed on a display unit of a mobile terminal.

FIG. 39 illustrates an example in which an index related to the physical condition of the pedestrian is displayed on the screen of a mobile terminal 210 of the pedestrian wearing a shoe 200 on which the data acquisition device (not illustrated) is installed. The pedestrian who has viewed the index related to the physical condition displayed on the screen of the mobile terminal 210 can take an action according to the physical condition. For example, a pedestrian who has viewed an index related to the physical condition displayed on the screen of the mobile terminal 210 can contact a medical institution, a workplace, an insurance company, or the like about his/her physical condition according to the physical condition. For example, a pedestrian who has viewed the index related to the physical condition displayed on the screen of the mobile terminal 210 can practice dietary habits and exercise suitable for the pedestrian according to the physical condition.

Figure 40:
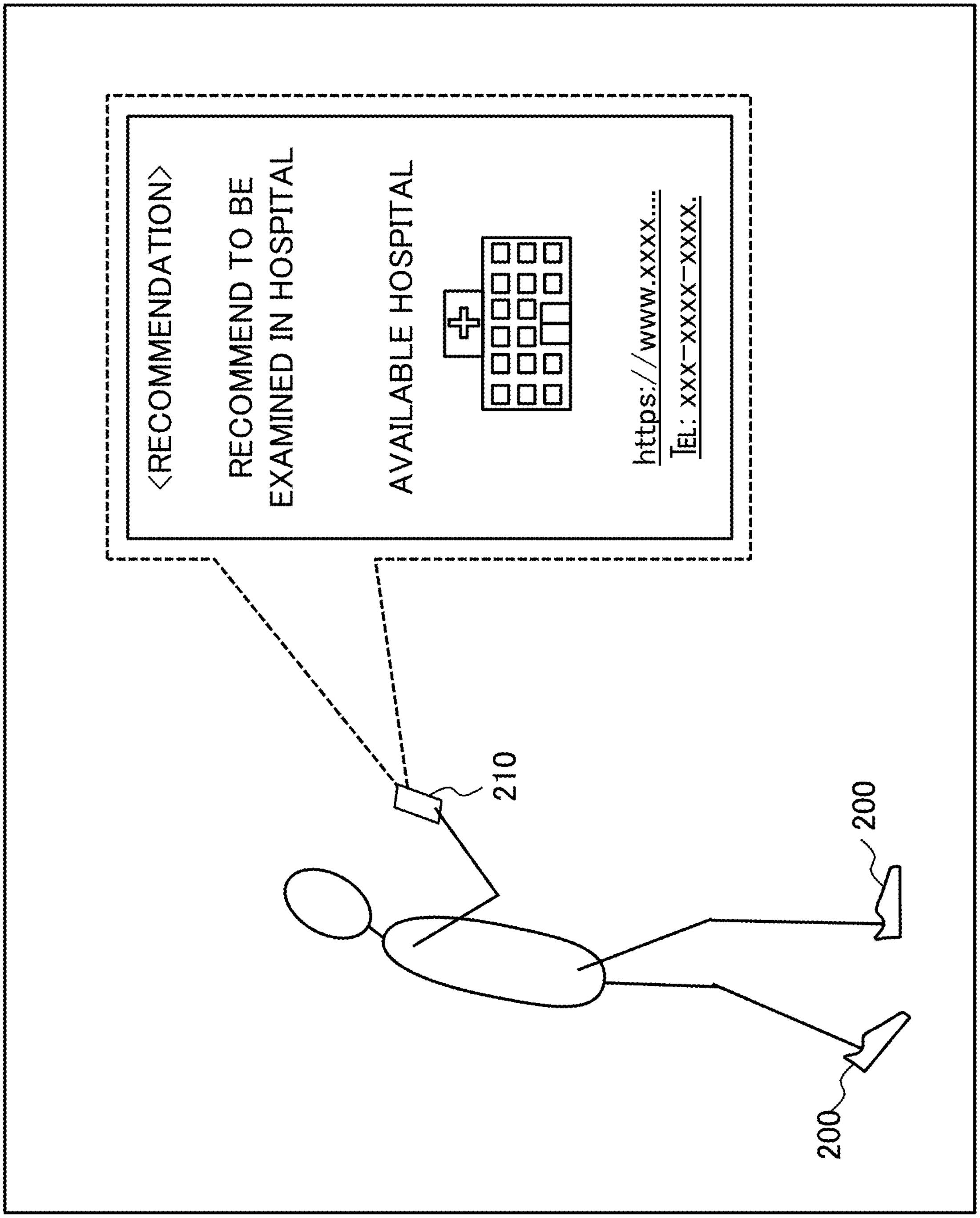
FIG. 40 is a conceptual diagram illustrating an example in which information according to a physical condition estimated by the detection device of the detection system according to the second example embodiment is displayed on a display unit of a mobile terminal.

FIG. 40 illustrates an example in which information corresponding to the physical condition is displayed on the screen of the mobile terminal 210 of the pedestrian wearing the shoe 200 in which the data acquisition device (not illustrated) is installed. For example, information recommending that a pedestrian be examined in a hospital is displayed on the screen of the mobile terminal 210 according to the progress state of muscle weakness and the deterioration state of bone density and basal metabolism. For example, a link to the site or a telephone number of an available hospital may be displayed on the screen of the mobile terminal 210 according to the progress state of muscle weakness or the deterioration state of bone density or basal metabolism.

Figure 41:
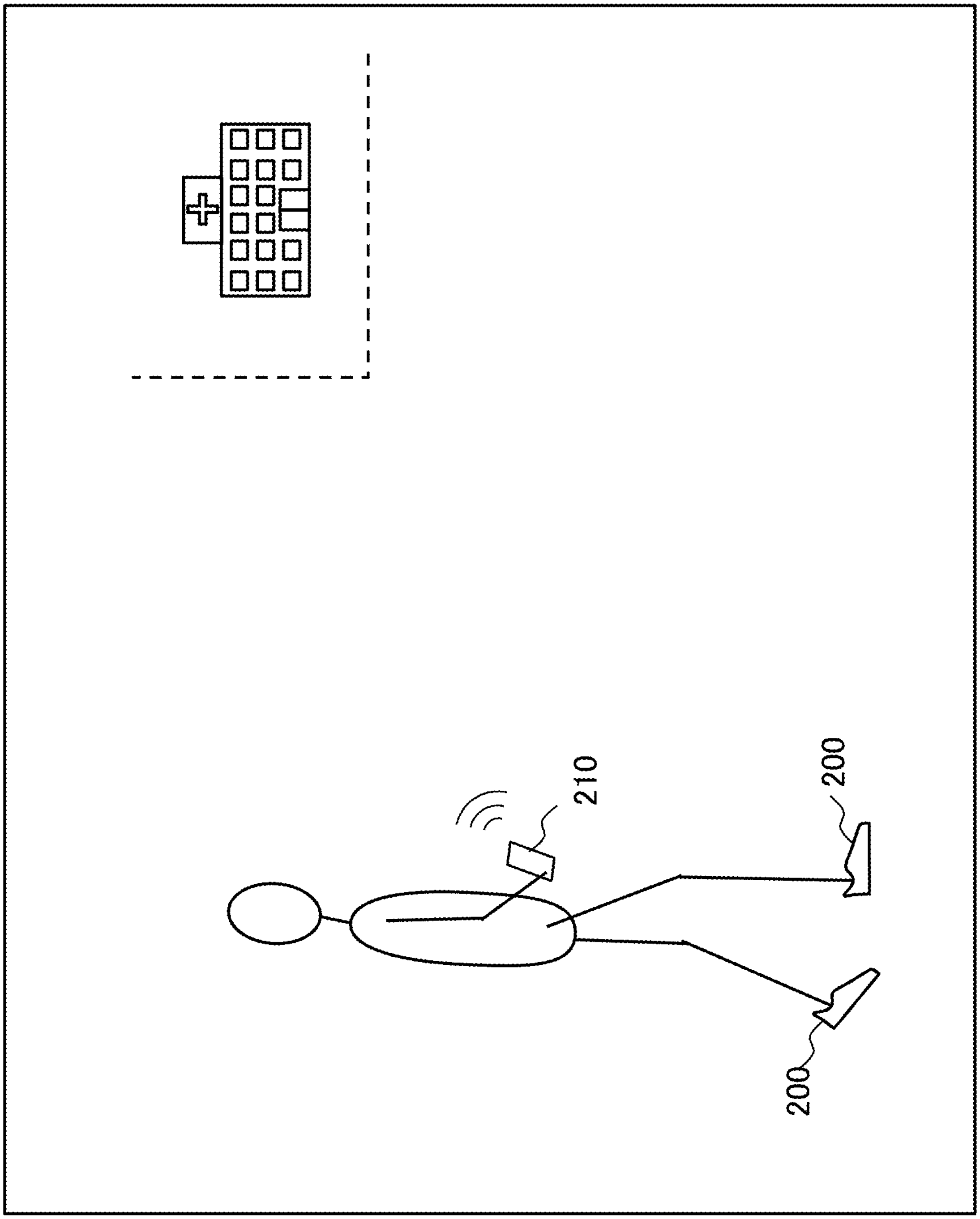

FIG. 41 illustrates an example in which information corresponding to the physical condition of the pedestrian wearing the shoe 200 on which the data acquisition device (not illustrated) is installed is transmitted from the mobile terminal 210 to a health management system installed in a medical institution or the like. For example, a medical worker or the like who handles the health management system transmits, to the mobile terminal 210 via the health management system, information advising a pedestrian to receive an examination in accordance with the progress state of muscle weakness or the deterioration state of bone density or basal metabolism of the pedestrian. For example, a pedestrian who has viewed information recommending an examination can go to a hospital for an examination according to the information.

As described above, the detection system of the present example embodiment includes the data acquisition device and the detection device. The data acquisition device measures the spatial acceleration and the spatial angular velocity, generates sensor data based on the measured spatial acceleration and spatial angular velocity, and transmits the generated sensor data to the detection device. The detection device includes an extraction unit, a detection unit, a calculation unit, and an estimation unit. The extraction unit generates time-series data associated with walking using sensor data based on a physical quantity related to movement of a foot measured by a sensor installed in one foot portion of a pedestrian, and extracts a gait waveform from the generated time-series data. The detection unit detects a gait event of both feet of the pedestrian from the gait waveform extracted by the extraction unit. The calculation unit specifies an occurrence time of a gait event detected from the gait waveform of the pedestrian, and calculates a time factor related to the gait on the basis of the specified occurrence time of the gait event. The estimation unit estimates the physical condition of the pedestrian based on the calculated time factor.

In the present example embodiment, the time factor related to the gait is specified based on the occurrence time of the gait event detected from the gait waveform of the pedestrian, and the specified time factor is analyzed. Human physical condition may affect asymmetry in walking. Therefore, according to the present example embodiment, the physical information of the pedestrian can be estimated by analyzing the time factor related to the gait of the pedestrian.

For example, the calculation unit calculates a time factor related to the ratio between the double-leg support period and the single-leg support period on the basis of the specified occurrence time of the gait event. The estimation unit estimates the muscle weakness state of the pedestrian based on the calculated time factor.

For example, the calculation unit calculates a time factor related to the ratio between the right-foot stance period and the left-foot stance period on the basis of the specified occurrence time of the gait event. The estimation unit estimates the bone density of the pedestrian based on the calculated time factor.

For example, the calculation unit calculates a time factor related to a ratio between the stride time of the right foot and the stride time of the left foot based on the specified occurrence time of the gait event. The estimation unit estimates the basal metabolism of the pedestrian based on the calculated time factor.

In this aspect, the asymmetry of walking is analyzed by analyzing the time factor of walking of the pedestrian. For example, the asymmetry of walking reflects physical conditions such as muscle weakness situation, bone density, and basal metabolism. Therefore, according to this aspect, the physical condition such as the muscle weakness situation, bone density, and basal metabolism of the pedestrian can be estimated by analyzing the time factor of walking of the pedestrian.

Third Example Embodiment

Next, a detection device according to a third example embodiment will be described with reference to the drawings. The detection device of the present example embodiment has a configuration in which the detection device of each example embodiment is simplified.

Figure 42:
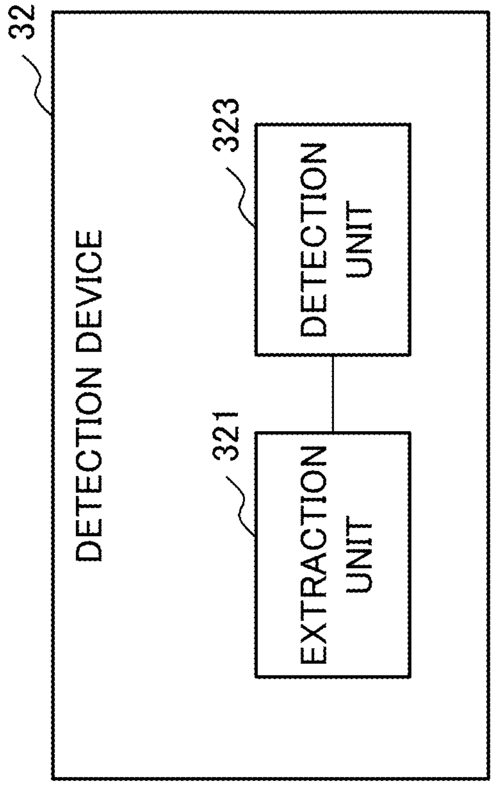
FIG. 42 is a block diagram illustrating an example of a configuration of a detection device according to a third example embodiment.

FIG. 42 is a block diagram illustrating an example of a configuration of a detection device 32 of the present example embodiment. The detection device 32 includes an extraction unit 321 and a detection unit 323. The extraction unit 321 generates time-series data associated with walking using sensor data based on a physical quantity related to the movement of the foot measured by a sensor installed in one foot portion of the pedestrian. The extraction unit 321 extracts a gait waveform from the generated time-series data. The detection unit 323 detects a gait event of both feet of the pedestrian from the gait waveform extracted by the extraction unit 321.

In the present example embodiment, a gait waveform is extracted from time-series data generated using sensor data based on a physical quantity related to movement of a foot measured by a sensor installed in one foot portion of a pedestrian. Then, in the present example embodiment, a gait event of both feet is detected from the extracted gait waveform. As a result, according to the present example embodiment, it is possible to detect a detailed gait event of both feet on the basis of the physical quantity related to the movement of the foot measured by the sensor attached to one foot.

(Hardware)

Here, a hardware configuration for executing processing of the detection device and the like according to the example embodiment will be described using an information processing device 90 of FIG. 43 as an example. Note that the information processing device 90 in FIG. 43 is a configuration example for executing processing of the detection device or the like of each example embodiment, and does not limit the scope of the present invention.

Figure 43:
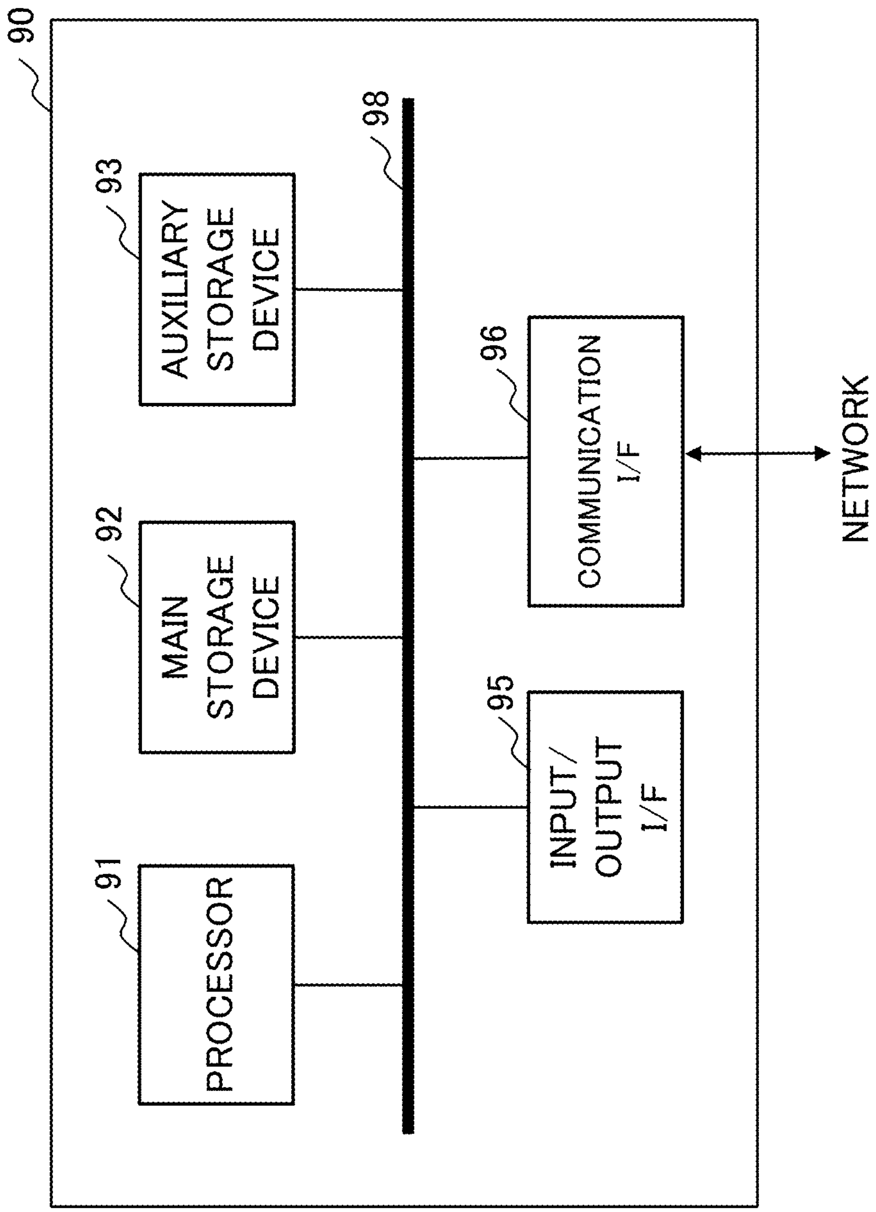
FIG. 43 is a block diagram for describing an example of a hardware configuration for implementing the detection device according to each example embodiment.

As illustrated in FIG. 43, the information processing device 90 includes a processor 91, a main storage device 92, an auxiliary storage device 93, an input/output interface 95, and a communication interface 96. In FIG. 43, the interface is abbreviated as an interface (I/F). The processor 91, the main storage device 92, the auxiliary storage device 93, the input/output interface 95, and the communication interface 96 are data-communicably connected to each other via a bus 98. In addition, the processor 91, the main storage device 92, the auxiliary storage device 93, and the input/output interface 95 are connected to a network such as the Internet or an intranet via the communication interface 96.

The processor 91 develops the program stored in the auxiliary storage device 93 or the like in the main storage device 92 and executes the developed program. In the present example embodiment, a software program installed in the information processing device 90 may be used. The processor 91 executes processing by the detection device according to the present example embodiment.

The main storage device 92 has an area in which a program is developed. The main storage device 92 may be a volatile memory such as a dynamic random access memory (DRAM). In addition, a nonvolatile memory such as a magnetoresistive random access memory (MRAM) may be configured and added as the main storage device 92.

The auxiliary storage device 93 stores various types of data. The auxiliary storage device 93 includes a local disk such as a hard disk or a flash memory. Note that various types of data may be stored in the main storage device 92, and the auxiliary storage device 93 may be omitted.

The input/output interface 95 is an interface for connecting the information processing device 90 and a peripheral device. The communication interface 96 is an interface for connecting to an external system or device through a network such as the Internet or an intranet based on a standard or a specification. The input/output interface 95 and the communication interface 96 may be shared as an interface connected to an external device.

An input device such as a keyboard, a mouse, or a touch panel may be connected to the information processing device 90 as necessary. These input devices are used to input information and settings. When the touch panel is used as the input device, the display screen of the display device may also serve as the interface of the input device. Data communication between the processor 91 and the input device may be mediated by the input/output interface 95.

The information processing device 90 may be provided with a display device for displaying information. In a case where a display device is provided, the information processing device 90 preferably includes a display control device (not illustrated) for controlling display of the display device. The display device may be connected to the information processing device 90 via the input/output interface 95.

The above is an example of a hardware configuration for enabling the detection device according to each example embodiment of the present invention. Note that the hardware configuration of FIG. 43 is an example of a hardware configuration for executing arithmetic processing of the detection device according to each example embodiment, and does not limit the scope of the present invention. In addition, a program for causing a computer to execute processing related to the detection device according to each example embodiment is also included in the scope of the present invention.

Further, a non-transitory recording medium (also referred to as a program recording medium) in which the program according to each example embodiment is recorded is also included in the scope of the present invention. For example, the recording medium can be implemented by an optical recording medium such as a compact disc (CD) or a digital versatile disc (DVD). Furthermore, the recording medium may be implemented by a semiconductor recording medium such as a universal serial bus (USB) memory or a secure digital (SD) card, a magnetic recording medium such as a flexible disk, or another recording medium.

The components of the detection device of each example embodiment can be arbitrarily combined. In addition, the components of the detection device of each example embodiment may be implemented by software or may be implemented by a circuit.

Although the present invention has been described with reference to the example embodiments, the present invention is not limited to the above example embodiments. Various modifications that can be understood by those of ordinary skill in the art can be made to the configuration and details of the present invention within the scope of the present invention.

Some or all of the above example embodiments may be described as the following supplementary notes, but are not limited to the following.

(Supplementary Note 1)

A detection device including:

an extraction unit configured to generate time-series data associated with walking using sensor data based on a physical quantity related to movement of a foot measured by a sensor installed in one foot portion of a pedestrian, and extract a gait waveform from the generated time-series data; and a detection unit configured to detect a gait event of both feet of the pedestrian from the gait waveform extracted by the extraction unit.

(Supplementary Note 2)

The detection device according to supplementary note 1, wherein the extraction unit is configured to:

generate time-series data of an acceleration in a traveling direction of the pedestrian; and extract a gait waveform of the acceleration in the traveling direction for one gait cycle from the generated time-series data of the acceleration in the traveling direction, and the detection unit is configured to:

detect a timing at which a trough is detected between two peaks included in a maximum peak as a timing of a toe-off in the extracted gait waveform of the acceleration in the traveling direction for one gait cycle; and detect a timing of a midpoint between a timing at which a minimum peak is detected and a timing at which a maximum peak appearing after the minimum peak is detected as a timing of a heel-strike.

(Supplementary Note 3)

The detection device according to supplementary note 2, wherein the extraction unit is configured to:

generate time-series data of a roll angular velocity of the pedestrian; and extract, from the generated time-series data of the roll angular velocity, a gait waveform of the roll angular velocity for one gait cycle starting from a start timing of a terminal stance stage, and the detection unit is configured to:

divide the extracted gait waveform of the roll angular velocity for one gait cycle into a first gait waveform, a second gait waveform, and a third gait waveform at the timing of the toe-off and the timing of the heel-strike;

detect a timing of an opposite heel-strike from the first gait waveform of the roll angular velocity; and detect a timing of an opposite toe-off is detected from the third gait waveform of the roll angular velocity.

(Supplementary Note 4)

The detection device according to supplementary note 3, wherein the detection unit is configured to:

detect a point at which the roll angular velocity becomes maximum from the first gait waveform of the roll angular velocity; and detect a timing of an acceleration inflection point at which a length of a perpendicular line drawn to the first gait waveform of the roll angular velocity from a line segment connecting a start point of the first gait waveform of the roll angular velocity and a point at which the roll angular velocity becomes maximum in the first gait waveform of the roll angular velocity as the timing of the opposite heel-strike.

(Supplementary Note 5)

The detection device according to supplementary note 3 or 4, wherein the detection unit is configured to:

detect a point at which the roll angular velocity becomes maximum from the third gait waveform of the roll angular velocity; and detect a timing of a deceleration inflection point at which a length of a perpendicular line drawn to the third gait waveform of the roll angular velocity from a line segment connecting a start point of the third gait waveform of the roll angular velocity and a point at which the roll angular velocity becomes maximum in the third gait waveform of the roll angular velocity as the timing of the opposite toe-off.

(Supplementary Note 6)

The detection device according to supplementary note 5, wherein the extraction unit is configured to:

generate time-series data of an acceleration in a gravity direction of the pedestrian; and extract, from the generated time-series data of the acceleration in the gravity direction, a gait waveform of the acceleration in the gravity direction for one gait cycle starting from a start timing of a terminal stance stage, and the detection unit is configured to:

divide the extracted gait waveform of the acceleration in the gravity direction for one gait cycle into a first gait waveform, a second gait waveform, and a third gait waveform at the timing of the toe-off and the timing of the heel-strike; and detect a timing at which the second gait waveform of the acceleration in the gravity direction becomes maximum as a timing of a tibia-vertical.

(Supplementary Note 7)

The detection device according to supplementary note 6, wherein the detection unit is configured to:

cut out a fourth gait waveform between the timing of the toe-off and the timing of the tibia-vertical from the gait waveform of the acceleration in the traveling direction for one gait cycle; and detect a timing at which a peak on a side close to the timing of the tibia-vertical included in the fourth gait waveform of the acceleration in the traveling direction becomes maximum as a timing of a foot-adjacent.

(Supplementary Note 8)

The detection device according to any one of supplementary notes 5 to 7, wherein the extraction unit is configured to:

extract, from the time-series data of the roll angular velocity, a gait waveform of the roll angular velocity for two gait cycles starting from a start timing of the terminal stance stage; and the detection unit is configured to:

detect a timing of an acceleration inflection point at which a length of a perpendicular line drawn to the gait waveform of the roll angular velocity from a line segment connecting a point of the opposite toe-off in the first gait cycle and a point of the opposite toe-off in the second gait cycle following the first gait cycle becomes maximum in the extracted gait waveform of the roll angular velocity for two gait cycles as a timing of a heel-rise.

(Supplementary Note 9)

The detection device according to any one of supplementary notes 1 to 8, further including:

a calculation unit configured to specify an occurrence time of the gait event detected from the gait waveform of the pedestrian and calculate a time factor related to a gait based on the specified occurrence time of the gait event; and an estimation unit configured to estimate a physical condition of the pedestrian based on the calculated time factor.

(Supplementary Note 10)

The detection device according to supplementary note 9, wherein the calculation unit is configured to:

calculate the time factor related to a ratio between a double-leg support period and a single-leg support period based on the specified occurrence time of the gait event, and the estimation unit is configured to:

estimate a muscle weakness state of the pedestrian based on the calculated time factor.

(Supplementary Note 11)

The detection device according to supplementary note 9 or 10, wherein the calculation unit is configured to:

calculate the time factor related to a ratio between a right-foot stance period and a left-foot stance period based on the specified occurrence time of the gait event, and the estimation unit is configured to:

estimate a bone density of the pedestrian based on the calculated time factor.

(Supplementary Note 12)

The detection device according to any one of supplementary notes 9 to 11, wherein the calculation unit is configured to:

calculate the time factor related to a ratio of a stride time of the right foot and a stride time of the left foot based on the specified occurrence time of the gait event, and the estimation unit is configured to:

estimate a basal metabolism of the pedestrian based on the calculated time factor.

(Supplementary Note 13)

A detection system including:

the detection device according to any one of supplementary notes 1 to 12; and a data acquisition device configured to measure a spatial acceleration and a spatial angular velocity, generate the sensor data based on the measured spatial acceleration and spatial angular velocity, and transmit the generated sensor data to the detection device.

(Supplementary Note 14)

A detection method for causing a computer to execute:

generating time-series data associated with walking using sensor data based on a physical quantity related to movement of a foot measured by a sensor installed in one foot portion of a pedestrian;

extracting a gait waveform from the generated time-series data; and detecting a gait event of both feet of the pedestrian from the extracted gait waveform.

(Supplementary Note 15)

A program for causing a computer to execute:

processing of generating time-series data associated with walking using sensor data based on a physical quantity related to a movement of a foot measured by a sensor installed in one foot portion of a pedestrian;

processing of extracting a gait waveform from the generated time-series data; and processing of detecting a gait event of both feet of the pedestrian from the extracted gait waveform.

REFERENCE SIGNS LIST

1, 2 Detection system
11, 21 Data acquisition device
12, 22, 32 Detection device
111 Acceleration sensor
112 Angular velocity sensor
113 Control unit
115 Data transmission unit
121, 221, 321 Extraction unit
123, 223, 323 Detection unit
225 Calculation unit
227 Estimation unit

What is claimed is:

1. A detection device comprising:

one or more memories storing instructions; and one or more processors configured to execute the instructions to:

receive, via wireless communication, sensor data from a data acquisition device installed in footwear worn on one foot of a pedestrian, the data acquisition device including an acceleration sensor and an angular velocity sensor;

convert the received sensor data from a local coordinate system of the data acquisition device into a world coordinate system set with respect to the ground, to generate time-series data associated with walking of the pedestrian;

generate, from the time-series data, at least one time-series of a spatial angle of the one foot by integrating at least one of a spatial acceleration and a spatial angular velocity included in the sensor data;

detect, based on the time-series of the spatial angle, a first timing at which the time-series becomes a minimum, a second timing at which the time-series becomes a maximum, a third timing at which the time-series becomes a next minimum and a fourth timing at which the time-series becomes a next maximum;

calculate a start time and an end time of a gait cycle based on a midpoint between the first timing and the second timing, and a midpoint between the third timing and the fourth timing, and cut out a gait waveform corresponding to the gait cycle from the time-series data;

detect a gait event of both feet of the pedestrian from the cut-out gait waveform;

specify an occurrence time of the gait event;

calculate a time factor related to gait based on the specified occurrence time of the gait event;

estimate a physical condition of the pedestrian by inputting a predictor vector including the time factor to a learned model generated by machine learning; and transmit, via a communication network, to a display device, information relating to the estimated physical condition, the information including a recommendation for assisting decision making regarding whether to seek medical consultation, for display on a screen of the display device, wherein the detection of the gait event of both feet is performed using the sensor data measured by the data acquisition device installed in the footwear on the one foot.

2. The detection device according to claim 1, wherein the one or more processors are configured to execute the instructions to:

generate time-series data of an acceleration in a traveling direction of the pedestrian;

extract the gait waveform of the acceleration in the traveling direction for one gait cycle from the generated time-series data of the acceleration in the traveling direction;

detect a timing at which a trough is detected between two peaks included in a maximum peak as a timing of a toe-off in the extracted gait waveform of the acceleration in the traveling direction for one gait cycle; and detect a timing of a midpoint between a timing at which a minimum peak is detected and a timing at which a maximum peak appearing after the minimum peak is detected as a timing of a heel-strike.

3. The detection device according to claim 2 wherein the one or more processors are configured to execute the instructions to:

generate time-series data of a roll angular velocity of the pedestrian;

extract, from the generated time-series data of the roll angular velocity, a gait waveform of the roll angular velocity for one gait cycle starting from a start timing of a terminal stance stage;

divide the extracted gait waveform of the roll angular velocity for one gait cycle into a first gait waveform, a second gait waveform, and a third gait waveform at the timing of the toe-off and the timing of the heel-strike;

detect a timing of an opposite heel-strike from the first gait waveform of the roll angular velocity; and detect a timing of an opposite toe-off from the third gait waveform of the roll angular velocity.

4. The detection device according to claim 3 wherein the one or more processors are configured to execute the instructions to:

detect a point at which the roll angular velocity becomes maximum from the first gait waveform of the roll angular velocity; and detect a timing of an acceleration inflection point at which a length of a perpendicular line drawn to the first gait waveform of the roll angular velocity from a line segment connecting a start point of the first gait waveform of the roll angular velocity and a point at which the roll angular velocity becomes maximum in the first gait waveform of the roll angular velocity as the timing of the opposite heel-strike.

5. The detection device according to claim 3, wherein the one or more processors are configured to execute the instructions to:

detect a point at which the roll angular velocity becomes maximum from the third gait waveform of the roll angular velocity; and detect a timing of a deceleration inflection point at which a length of a perpendicular line drawn to the third gait waveform of the roll angular velocity from a line segment connecting a start point of the third gait waveform of the roll angular velocity and a point at which the roll angular velocity becomes maximum in the third gait waveform of the roll angular velocity as the timing of the opposite toe-off.

6. The detection device according to claim 5 wherein the one or more processors are configured to execute the instructions to:

generate time-series data of an acceleration in a gravity direction of the pedestrian;

extract, from the generated time-series data of the acceleration in the gravity direction, a gait waveform of the acceleration in the gravity direction for one gait cycle starting from a start timing of a terminal stance stage;

divide the extracted gait waveform of the acceleration in the gravity direction for one gait cycle into a fourth gait waveform, a fifth gait waveform, and a sixth gait waveform at the timing of the toe-off and the timing of the heel-strike; and detect a timing at which the second gait waveform of the acceleration in the gravity direction becomes maximum as a timing of a tibia-vertical.

7. The detection device according to claim 6 wherein the one or more processors are configured to execute the instructions to:

cut out a seventh gait waveform between the timing of the toe-off and the timing of the tibia-vertical from the gait waveform of the acceleration in the traveling direction for one gait cycle; and detect a timing at which a peak on a side close to the timing of the tibia-vertical included in the seventh gait waveform of the acceleration in the traveling direction becomes maximum as a timing of a foot-adjacent.

8. The detection device according to claim 5, wherein the one or more processors are configured to execute the instructions to:

extract, from the time-series data of the roll angular velocity, a gait waveform of the roll angular velocity for two gait cycles starting from a start timing of the terminal stance stage;

detect a timing of an acceleration inflection point at which a length of a perpendicular line drawn to the gait waveform of the roll angular velocity from a line segment connecting a point of the opposite toe-off in a first gait cycle and a point of the opposite toe-off in a second gait cycle following the first gait cycle becomes maximum in the extracted gait waveform of the roll angular velocity for two gait cycles as a timing of a heel-rise.

9. The detection device according to claim 1, wherein the one or more processors are configured to execute the instructions to:

calculate the time factor related to a ratio between a double-leg support period and a single-leg support period based on the specified occurrence time of the gait event, and estimate a muscle weakness state of the pedestrian based on the calculated time factor.

10. The detection device according to claim 1, wherein the one or more processors are configured to execute the instructions to:

calculate the time factor related to a ratio between a right-foot stance period and a left-foot stance period based on the specified occurrence time of the gait event; and estimate a bone density of the pedestrian based on the calculated time factor.

11. The detection device according to claim 1, wherein the one or more processors are configured to execute the instructions to:

calculate the time factor related to a ratio of a stride time of the right foot and a stride time of the left foot based on the specified occurrence time of the gait event; and estimate a basal metabolism of the pedestrian based on the calculated time factor.

12. A detection method for causing a computer to execute:

receiving, via wireless communication, sensor data from a data acquisition device installed in footwear worn on one foot of a pedestrian, the data acquisition device including an acceleration sensor and an angular velocity sensor;

converting the received sensor data from a local coordinate system of the data acquisition device into a world coordinate system set with respect to the ground, to generate time-series data associated with walking of the pedestrian;

generating, from the time-series data, at least one time-series of a spatial angle of the one foot by integrating at least one of a spatial acceleration and a spatial angular velocity included in the sensor data;

detecting, based on the time-series of the spatial angle, a first timing at which the time-series becomes a minimum, a second timing at which the time-series becomes a maximum, a third timing at which the time-series becomes a next minimum and a fourth timing at which the time-series becomes a next maximum;

calculating a start time and an end time of a gait cycle based on a midpoint between the first timing and the second timing, and a midpoint between the third timing and the fourth timing, and cutting out a gait waveform corresponding to the gait cycle from the time-series data;

detecting a gait event of both feet of the pedestrian from the cut-out gait waveform;

specifying an occurrence time of the gait event;

calculating a time factor related to gait based on the specified occurrence time of the gait event;

estimating a physical condition of the pedestrian by inputting a predictor vector including the time factor to a learned model generated by machine learning; and transmitting, via a communication network, to a display device, information relating to the estimated physical condition, the information including a recommendation for assisting decision making regarding whether to seek medical consultation, for display on a screen of the display device, wherein the detection of the gait event of both feet is performed using the sensor data measured by the data acquisition device installed in the footwear on the one foot.

13. A non-transitory program recording medium recorded with a program for causing a computer to execute:

processing of receiving, via wireless communication, sensor data from a data acquisition device installed in footwear worn on one foot of a pedestrian, the data acquisition device including an acceleration sensor and an angular velocity sensor;

processing of converting the received sensor data from a local coordinate system of the data acquisition device into a world coordinate system set with respect to the ground, to generate time-series data associated with walking of the pedestrian;

processing of generating, from the time-series data, at least one time-series of a spatial angle of the one foot by integrating at least one of a spatial acceleration and a spatial angular velocity included in the sensor data;

processing of detecting, based on the time-series of the spatial angle, a first timing at which the time-series becomes a minimum, a second timing at which the time-series becomes a maximum, a third timing at which the time-series becomes a next minimum and a fourth timing at which the time-series becomes a next maximum;

processing of calculating a start time and an end time of a gait cycle based on a midpoint between the first timing and the second timing, and a midpoint between the third timing and the fourth timing, and cutting out a gait waveform corresponding to the gait cycle from the time-series data;

processing of detecting a gait event of both feet of the pedestrian from the cut-out gait waveform;

processing of specifying an occurrence time of the gait event;

processing of calculating a time factor related to gait based on the specified occurrence time of the gait event;

processing of estimating a physical condition of the pedestrian by inputting a predictor vector including the time factor to a learned model generated by machine learning; and processing of transmitting, via a communication network, to a display device, information relating to the estimated physical condition, the information including a recommendation for assisting decision making regarding whether to seek medical consultation, for display on a screen of the display device, wherein the processing of detecting the gait event of both feet is performed using the sensor data measured by the data acquisition device installed in the footwear on the one foot.

* * * * *